(12) United States Patent  (10) Patent No.: US 7,482,341 B2
Amrein et al.  (45) Date of Patent: Jan. 27, 2009

(54) PYRIDINES

(75) Inventors: Kurt Amrein, Itingen (CH); Daniel Hunziker, Moehlin (CH); Bernd Kuhn, Liestal (CH); Alexander Mayweg, Loerrach (DE); Werner Neidhart, Hagenthal le Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 301 days.

(21) Appl. No.: 11/238,598

(22) Filed: Sep. 29, 2005

(65) Prior Publication Data

US 2006/0074237 A1 Apr. 6, 2006

(30) Foreign Application Priority Data

Oct. 4, 2004 (EP) .................................. 04104856

(51) Int. Cl.
*C07D 401/02* (2006.01)
*A61K 31/44* (2006.01)

(52) U.S. Cl. ....................... 514/230.8; 544/60; 544/124; 546/146; 546/153; 546/193; 546/304; 514/309; 514/312; 514/318; 514/352

(58) Field of Classification Search ........................ None
See application file for complete search history.

(56) References Cited

FOREIGN PATENT DOCUMENTS

| WO | WO 2004/076413 A2 | 9/2004 |
| WO | WO 2005/040135 A1 | 5/2005 |
| WO | WO 2005/060963 A1 | 7/2005 |

OTHER PUBLICATIONS

Raiziss et al, Journal of the American Chemical Society, 1941, vol. 63, pp. 2739-2740.*
Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997; 94(26):14924-9.
Masuzaki H. et al., J Clin Invest. Jul. 2003;112(1):83-90.
Sandeep TC. et al., Proc Natl Acad Sci U S A. Apr. 27, 2004;101(17):6734-9.
Kazuyuki, et al., Chemical Abstracts, XP002355154, 2005.
Database Beilstein, XP002355155 & Acheson, et al., J. Chem. Res. Miniprint, p. 3901 (1979).

* cited by examiner

*Primary Examiner*—Zinna N Davis
(74) *Attorney, Agent, or Firm*—George W. Johnston; Dennis P. Tramaloni; Samuel H. Megerditchian

(57) ABSTRACT

Compounds of formula

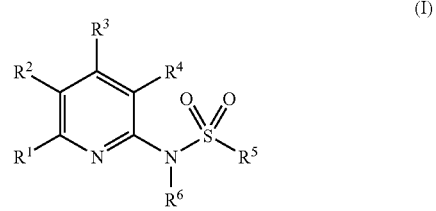

as well as pharmaceutically acceptable salts and esters thereof, wherein $R^1$ to $R^6$ have the significance given in claim 1 can be used in the form of pharmaceutical compositions.

16 Claims, No Drawings

PYRIDINES

FIELD OF THE INVENTION

The present invention is directed to novel pyridine derivatives useful as 11b-HSD1 inhibitors (T2D).

In a preferred embodiment, the invention is directed to compounds of formula (I):

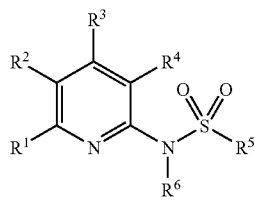

and pharmaceutically acceptable salts and esters thereof.

All documents cited or relied upon below are expressly incorporated herein by reference.

BACKGROUND OF THE INVENTION

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active form. 11beta-hydroxysteroid dehydrogenases (11beta-HSD's) catalyze the interconversion of the principal active 11-hydroxy-glucocorticoid and their inactive 11-keto metabolites.

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese men were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in humans might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci U S A. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July;112(1): 83-90; Rauz S. et al., QJM. 2003 July;96(7):481-90) to improve cognition (Sandeep T C. et al., Proc Natl Acad Sci U S A. 2004 Apr. 27;101(17):6734-9) or to improve Alzheimer associated deficits. Taken together 11beta-HSD1 inhibition might be a safe and efficacious approach to treat symptoms of diabetes, obesity and other diseases.

SUMMARY OF THE INVENTION

In one embodiment of the present invention, provided is a compound of the formula (I):

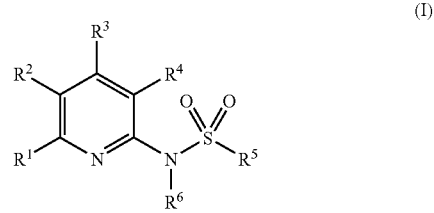

wherein:

$R^1$ is hydrogen, alkyl, cycloalkyl, hydroxy, hydroxyalkyl, alkoxy, alkoxyalkyl, aminoalkyl, aryl, heterocyclyl, alkylsulfonyl, alkylsulfanyl, alkylcarbonylalkyl, alkylcarbonyloxyalkyl, aminocarbonylalkyl, heterocyclylcarbonylalkyl, heterocyclylalkoxyalkyl, alkoxycarbonylalkyl, alkoxyalkylaminocarbonylalkyl, cycloalkylalkoxyalkyl, arylalkyloxyalkyl, aryloxyalkyl, haloalkyl, haloalkoxy or haloalkoxyalkyl;

$R^2$ is hydrogen, alkyl, cycloalkylalkoxyalkyl, alkoxyalkyl, arylalkoxyalkyl, haloalkoxyalkyl, piperidyl, pyrrolidyl, morpholinyl, thiomorpholinyl arylalkyl, arylalkoxy, aryloxy, heterocyclylalkoxy or heterocyclylalkyl;

$R^3$ is hydrogen or alkyl;

$R^4$ is hydrogen, alkyl or halogen;

$R^5$ is phenyl, naphtyl, thiophenyl, pyridyl, quinolyl, piperidyl, morpholyl, thiomorpholyl or 1,2,3,4-tetrahydroisoquinolinyl optionally substituted with one or more substituents independently selected from alkyl, cycloalkyl, halogen, hydroxy, hydroxyalkyl, alkoxy, alkoxyalkyl, hydroxyalkoxy, alkoxyalkoxy, cyano, nitro, trifluoromethyl, trifluoromethoxy, trifluoromethylcarbonyl, aryl, arylalkyl, aryloxy, alkoxycarbonylalkoxy and alkylsulfonyl;

$R^6$ is hydrogen or alkyl;

and pharmaceutically acceptable salts and esters thereof;

with the proviso that N-(6-(1,1-dimethylethyl)-2-pyridinyl)-4-methyl-benzenesulfonamide is excluded, and with the proviso that when $R^1$ is hydrogen or methyl, then $R^2$ is not hydrogen or methyl.

In another embodiment of the present invention, provided is a process for the preparation of a compound according to formula (I), comprising the steps of: reaction of a compound according to formula (II):

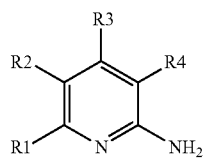

II in the presence of a compound according to formula

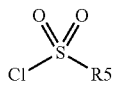

in order to obtain a compound of the formula

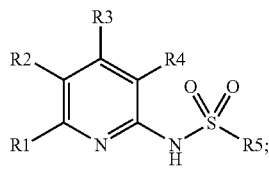

Ia and optionally further reaction in the presence of a compound of the formula $R^6$—X in order to obtain a compound of the formula

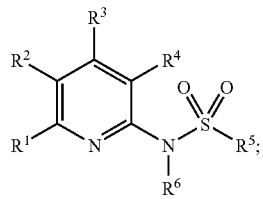

(I)

wherein $R^1$ to $R^6$ are defined as for formula (I).

In a further embodiment of the present invention, provided is a pharmaceutical composition, comprising a therapeutically effective amount of a compound according to formula (I), or pharmaceutically acceptable salts and esters thereof, and a therapeutically inert carrier.

In a yet another embodiment of the present invention, provided is a method for the treatment and prophylaxis of diabetes, obesity, eating disorders, dyslipidemiae and hypertension, comprising the step of administering a therapeutically effective amount of a compound according to formula (I), or pharmaceutically acceptable salts and esters thereof, to a patient in need thereof.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cydoheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-SO$_2$—, amino-SO$_2$—, cycloalkyl and the like. Preferred is phenyl or naphthyl, particularly phenyl optionally substituted with one to three, preferably one or two substituents independently selected from alkyl, halogen, alkoxy, trifluoromethoxy, nitro and trifluoromethyl. Particularly preferred is phenyl.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e.=N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g.1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred examples are thiophenyl, quinolyl, piperidyl, morpholyl, thiomorpholyl, oxazolyl, pyridinyl, pyrimidinyl, pyrazolyl, imidazolyl, pyrrolidinyl and thiazolyl. Particularly preferred examples are piperidyl, morpholyl, thiomorpholyl, pyridinyl and pyrrolidinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "haloalkyl", alone or in combination, signifies an alkyl group as defined before, wherein one or more, preferably one to five hydrogen atoms are replaced by halogen, preferably fluoro. Examples of such haloalkyl groups are difluoromethyl, trifluoromethyl and pentafluoroethyl. Preferred is trifluoromethyl.

The term "haloalkoxy", alone or in combination, signifies an alkoxy group as defined before, wherein one or more, preferably one to five hydrogen atoms are replaced by halogen, preferably fluoro. Examples of such haloalkoxy groups are difluoromethoxy, trifluoromethoxy, monofluoroethoxy and pentafluoroethoxy. Preferred is trifluoromethoxy and monofluoroethoxy.

The term "hydroxyalkyl", alone or in combination, signifies an allkyl group as defined before, wherein one or more hydrogen atoms, preferably one hydrogen atom is replaced by a hydroxy group. Examples of hydroxyalkyl are hydroxymethyl and hydroxyethyl.

The term "carbonyl", alone or in combination, signifies the —C(O)— group.

The term "oxy", alone or in combination, signifies the —O— group.

The term "nitro", alone or in combination signifies the —NO$_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Preferred are the compounds of formula I, wherein $R^5$ is phenyl, naphtyl, thiophenyl, pyridyl, quinolyl, piperidyl, morpholyl, thiomorpholyl or 1,2,3,4-tetrahydro-isoquinolinyl optionally substituted with one or more substituents, preferably one to three substituents, independently selected from alkyl, cycloalkyl, halogen, hydroxy, hydroxyalkyl, alkoxy, alkoxyalkyl, hydroxyalkoxy, alkoxyalkoxy, cyano, nitro, trifluoromethyl, trifluoromethoxy, trifluoromethylcarbonyl, aryl, arylalkyl, aryloxy, alkoxycarbonylalkoxy and alkyl-$SO_2$—.

Particularly preferred are those compounds of formula I, wherein $R^5$ is phenyl, naphtyl, thiophenyl, pyridyl, quinolyl, piperidyl, morpholyl, thiomorpholyl or 1,2,3,4-tetrahydro-isoquinolinyl optionally substituted with one or two substituents independently selected from alkyl, cycloalkyl, halogen, hydroxy, hydroxyalkyl, alkoxy, alkoxyalkyl, hydroxyalkoxy, alkoxyalkoxy, cyano, nitro, trifluoromethyl, trifluoromethoxy, trifluoromethylcarbonyl, aryl, arylalkyl, aryloxy, alkoxycarbonylalkoxy and alkyl-$SO_2$—.

Further preferred are compounds according to formula I, wherein $R^5$ is phenyl, naphtyl, piperidyl or 1,2,3,4-tetrahydro-isoquinolinyl optionally substituted with one to three substituents independently selected from alkyl, halogen, alkoxy, nitro, trifluoromethyl, trifluoromethoxy, trifluoromethylcarbonyl, aryl, aryloxy and alkyl-$SO_2$—.

Particularly preferred are compounds of formula I, wherein $R^5$ is phenyl or naphtyl optionally substituted with one to three substituents independently selected from alkyl, halogen, trifluoromethyl, trifluoromethoxy and aryl.

Also preferred are compounds according to formula I, wherein $R^6$ is hydrogen.

Preferred are compounds of formula I, wherein $R^1$ is hydrogen, alkyl, cycloalkyl, hydroxy, hydroxyalkyl, alkoxy, alkoxyalkyl, aminoalkyl, aryl, heterocyclyl, alkylsulfonyl, alkylsulfanyl, alkylcarbonylalkyl, alkylcarbonyloxyalkyl, aminocarbonylalkyl, heterocyclylcarbonylalkyl, heterocyclylalkoxyalkyl such as e.g. pyridylmethoxymethyl, alkoxycarbonylalkyl, alkoxyalkylaminocarbonylalkyl, cydoalkylalkoxyalkyl, arylalkyloxyalkyl, aryloxyalkyl, haloalkyl, haloalkoxy or haloalkoxyalkyl.

Further preferred are compounds of formula I, wherein $R^1$ is alkyl, cycloalkyl, hydroxyalkyl, alkoxyalkyl, aryl, alkoxyalkylaminocarbonylalkyl, cycloalkylalkoxyalkyl, arylalkyloxyalkyl or trifluoroalkoxyalkyl.

Another preferred embodiment of the present invention are compounds of formula I, wherein $R^1$ is hydrogen.

Preferred are the compounds of formula I, wherein $R^2$ is hydrogen, alkyl, cycloalkylalkoxyalkyl, alkoxyalkyl, arylalkoxyalkyl, haloalkoxyalkyl such as e.g. fluoro-ethoxymethyl or trifluoro-ethoxymethyl, piperidyl, pyrrolidyl, morpholinyl, thiomorpholinyl arylalkyl, arylalkoxy, aryloxy, heterocyclylalkoxy or heterocyclylalkyl;

Further preferred are compounds of formula I, wherein $R^2$ is hydrogen, cycloalkylalkoxyalkyl, alkoxyalkyl, piperidyl, pyrrolidyl, morpholinyl, thiomorpholinyl, arylalkyl or arloxy.

Also preferred are compounds according to formula I, wherein $R^3$ is hydrogen.

Further preferred are compounds according to formula I, wherein $R^4$ is hydrogen or halogen.

Particularly preferred are those compounds of formula I, wherein $R^4$ is hydrogen.

Examples of preferred compounds of formula (I) are:
3-Chloro-N-(6-ethyl-pyridin-2-yl)-2-methyl-benzenesulfonamide;
Biphenyl-4-sulfonic acid (6-ethyl-pyridin-2-yl)-amide;
Biphenyl-4-sulfonic acid (6-propyl-pyridin-2-yl)-amide;
3-Chloro-2-methyl-N-(6-propyl-pyridin-2-yl)-benzenesulfonamide;
Naphthalene-2-sulfonic acid (6-propyl-pyridin-2-yl)-amide;
3,4-Dichloro-N-(6-propyl-pyridin-2-yl)-benzenesulfonamide;
2,5-Difluoro-N-(6-propyl-pyridin-2-yl)-benzenesulfonamide;
2,4-Dichloro-6-methyl-N-(6-propyl-pyridin-2-yl)-benzenesulfonamide;
5-Chloro-naphthalene-2-sulfonic acid (6-propyl-pyridin-2-yl)-amide;
3,4-Dimethoxy-N-(6-propyl-pyridin-2-yl)-benzenesulfonamide;
4,5-Dichloro-2-fluoro-N-(6-propyl-pyridin-2-yl)-benzenesulfonamide;
2,4-Dichloro-5-methyl-N-(6-propyl-pyridin-2-yl)-benzenesulfonamide;
Piperidine-1-sulfonic acid (6-propyl-pyridin-2-yl)-amide;
3-Chloro-N-(6-isopropyl-pyridin-2-yl)-4-methyl-benzenesulfonamide;
2,5-Difluoro-N-(6-isopropyl-pyridin-2-yl)-benzenesulfonamide;
N-(6-Isopropyl-pyridin-2-yl)-4-(4-trifluoromethyl-phenoxy)-benzenesulfonamide;
2,4-Dichloro-N-(6-isopropyl-pyridin-2-yl)-5-methyl-benzenesulfonamide;
N-(6-Isopropyl-pyridin-2-yl)-4-methanesulfonyl-benzenesulfonamide;
N-(6-Isopropyl-pyridin-2-yl)-4-trifluoromethoxy-benzenesulfonamide;
2-(2,2,2-Trifluoro-acetyl)-1,2,3,4-tetrahydro-isoquinoline-7-sulfonic acid (6-isopropyl-pyridin-2-yl)-amide;
N-(6-Isopropyl-pyridin-2-yl)-3-(4-trifluoromethyl-phenoxy)-benzenesulfonamide;
Naphthalene-2-sulfonic acid (6-isopropyl-pyridin-2-yl)-amide;
N-(6-Isopropyl-pyridin-2-yl)-3-trifluoromethyl-benzenesulfonamide;
N-[6-(2-Chloro-phenyl)-pyridin-2-yl]-5-fluoro-2-methyl-benzenesulfonamide;
3-Chloro-N-[6-(2-chloro-phenyl)-pyridin-2-yl]-2-methyl-benzenesulfonamide;
Biphenyl-4-sulfonic acid [6-(2-chloro-phenyl)-pyridin-2-yl]-amide;
3-Chloro-N-[6-(2,4-difluoro-phenyl)-pyridin-2-yl]-2-methyl-benzenesulfonamide;
3-Chloro-N-[6-(3-fluoro-phenyl)-pyridin-2-yl]-2-methyl-benzenesulfonamide;
3-Chloro-N-[6-(2,3-difluoro-phenyl)-pyridin-2-yl]-2-methyl-benzenesulfonamide;
3-Chloro-N-[6-(2,5-dichloro-phenyl)-pyridin-2-yl]-2-methyl-benzenesulfonamide;

N-[6-(2,5-Dichloro-phenyl)-pyridin-2-yl]-5-fluoro-2-methyl-benzenesulfonamide;
3-Chloro-N-[6-(3-chloro-phenyl)-pyridin-2-yl]-2-methyl-benzenesulfonamide;
N-[6-(3-Chloro-phenyl)-pyridin-2-yl]-5-fluoro-2-methyl-benzenesulfonamide;
3-Chloro-N-[6-(2-fluoro-phenyl)-pyridin-2-yl]-2-methyl-benzenesulfonamide;
5-Fluoro-N-[6-(2-fluoro-phenyl)-pyridin-2-yl]-2-methyl-benzenesulfonamide;
3-Chloro-2-methyl-N-[6-(2-trifluoromethyl-phenyl)-pyridin-2-yl]-benzenesulfonamide;
5-Fluoro-2-methyl-N-[6-(2-trifluoromethyl-phenyl)-pyridin-2-yl]-benzenesulfonamide;
N-[6-(2-Chloro-phenyl)-pyridin-2-yl]-2,5-difluoro-benzenesulfonamide;
N-[6-(2-Chloro-phenyl)-pyridin-2-yl]-2-trifluoromethyl-benzenesulfonamide;
3-Chloro-N-[6-(2-methoxy-phenyl)-pyridin-2-yl]-2-methyl-benzenesulfonamide;
3-Chloro-N-[6-(4-fluoro-2-methyl-phenyl)-pyridin-2-yl]-2-methyl-benzenesulfonamide;
5-Fluoro-N-[6-(4-fluoro-2-methyl-phenyl)-pyridin-2-yl]-2-methyl-benzenesulfonamide;
N-[2,3']Bipyridinyl-6-yl-3-chloro-2-methyl-benzenesulfonamide;
2,5-Difluoro-N-[6-(4-fluoro-2-methyl-phenyl)-pyridin-2-yl]-benzenesulfonamide;
2,4-Dichloro-N-[6-(4-fluoro-2-methyl-phenyl)-pyridin-2-yl]-6-methyl-benzenesulfonamide;
3,4-Dichloro-N-[6-(4-fluoro-2-methyl-phenyl)-pyridin-2-yl]-benzenesulfonamide;
3-Chloro-N-(6-methoxy-pyridin-2-yl)-2-methyl-benzenesulfonamide;
Biphenyl-4-sulfonic acid (6-methoxy-pyridin-2-yl)-amide;
5-Fluoro-N-(6-methoxy-pyridin-2-yl)-2-methyl-benzenesulfonamide;
Naphthalene-2-sulfonic acid (6-methoxy-pyridin-2-yl)-amide;
3-Chloro-N-(6-ethoxy-pyridin-2-yl)-2-methyl-benzenesulfonamide;
Biphenyl-4-sulfonic acid (6-ethoxy-pyridin-2-yl)-amide;
Naphthalene-2-sulfonic acid (6-ethoxy-pyridin-2-yl)-amide;
3-Chloro-N-(6-ethylsulfanyl-pyridin-2-yl)-2-methyl-benzenesulfonamide;
Biphenyl-4-sulfonic acid (6-ethylsulfanyl-pyridin-2-yl)-amide;
Naphthalene-2-sulfonic acid (6-ethylsulfanyl-pyridin-2-yl)-amide;
Naphthalene-2-sulfonic-acid (6-ethanesulfonyl-pyridin-2-yl)-amide;
3-Chloro-2-methyl-N-[6-(2-oxo-pentyl)-pyridin-2-yl]-benzenesulfonamide;
2-[6-(Biphenyl-4-sulfonylamino)-pyridin-2-yl]-N,N-diethyl-acetamide;
Biphenyl-4-sulfonic acid [6-(2-morpholin-4-yl-2-oxo-ethyl)-pyridin-2-yl]-amide;
[6-(3-Chloro-2-methyl-benzenesulfonylamino)-pyridin-2-yl]-acetic acid methyl ester;
[6-(5-Fluoro-2-methyl-benzenesulfonylamino)-pyridin-2-yl]-acetic acid methyl ester;
N,N-Diethyl-2-[6-(4'-fluoro-biphenyl-4-sulfonylamino)-pyridin-2-yl]-acetamide;
4-Fluoro-biphenyl-4-sulfonic acid [6-(2-morpholin-4-yl-2-oxo-ethyl)-pyridin-2-yl]-amide;
2-[6-(4-Fluoro-biphenyl-4-sulfonylamino)-pyridin-2-yl]-N-(2-methoxy-ethyl)-acetamide;
2-[6-(3-Chloro-2-methyl-benzenesulfonylamino)-pyridin-2-yl]-N,N-diethyl-acetamide;
2-[6-(3,4-Dichloro-benzenesulfonylamino)-pyridin-2-yl]-N,N-diethyl-acetamide
2-[6-(3-Chloro-2-methyl-benzenesulfonylamino)-3-methyl-pyridin-2-yl]-N,N-diethyl-acetamide;
2-[6-(3,4-Dichloro-benzenesulfonylamino)-3-methyl-pyridin-2-yl]-N,N-diethyl-acetamide;
3-Chloro-N-(6-hydroxymethyl-pyridin-2-yl)-2-methyl-benzenesulfonamide;
3-Chloro-N-(6-methoxymethyl-pyridin-2-yl)-2-methyl-benzenesulfonamide;
2,5-Difluoro-N-(6-methoxymethyl-pyridin-2-yl)-benzenesulfonamide;
3-Chloro-N-(6-methoxymethyl-pyridin-2-yl)-4-methyl-benzenesulfonamide;
N-(6-Cyclopropylmethoxymethyl-pyridin-2-yl)-2,5-difluoro-benzenesulfonamide;
5-Fluoro-N-(6-methoxymethyl-pyridin-2-yl)-2-methyl-benzenesulfonamide;
2,5-Difluoro-N-(6-hydroxymethyl-pyridin-2-yl)-benzenesulfonamide;
Acetic acid 6-(2,5-difluoro-benzenesulfonylamino)-pyridin-2-ylmethyl ester;
Naphthalene-2-sulfonic acid (6-hydroxymethyl-pyridin-2-yl)-amide;
3-Chloro-N-(6-cyclopropylmethoxymethyl-pyridin-2-yl)-4-methyl-benzenesulfonamide;
N-(6-Cyclopropylmethoxymethyl-pyridin-2-yl)-5-fluoro-2-methyl-benzenesulfonamide;
3-Chloro-N-[6-(4-fluoro-benzyloxymethyl)-pyridin-2-yl]-4-methyl-benzenesulfonamide;
3-Chloro-N-[6-(4-fluoro-benzyloxymethyl)-pyridin-2-yl]-2-methyl-benzenesulfonamide;
2,5-Difluoro-N-[6-(4-fluoro-benzyloxymethyl)-pyridin-2-yl]-benzenesulfonamide;
5-Fluoro-N-[6-(4-fluoro-benzyloxymethyl)-pyridin-2-yl]-2-methyl-benzenesulfonamide;
Piperidine-1-sulfonic acid (6-methoxymethyl-pyridin-2-yl)-amide;
Piperidine-1-sulfonic acid (6-cyclopropylmethoxymethyl-pyridin-2-yl)-amide
3-Chloro-4-methyl-N-[6-(4-trifluoromethyl-phenoxymethyl)-pyridin-2-yl]-benzenesulfonamide;
3-Chloro-2-methyl-N-[6-(4-trifluoromethyl-phenoxymethyl)-pyridin-2-yl]-benenesulfonamide;
2,5-Difluoro-N-[6-(4-trifluoromethyl-phenoxymethyl)-pyridin-2-yl]-benzenesulfonamide;
5-Fluoro-2-methyl-N-[6-(4-trifluoromethyl-phenoxymethyl)-pyridin-2-yl]-benzenesulfonamide;
3-Chloro-N-(6-cyclopropylmethoxymethyl-pyridin-2-yl)-2-methyl-benzenesulfonamide;
3,4-Dichloro-N-(6-cyclopropylmethoxymethyl-pyridin-2-yl)-benzenesulfonamide;
4-Fluoro-N-[6-(4-fluoro-benzyloxymethyl)-pyridin-2-yl]-benzenesulfonamide;
N-[6-(4-Fluoro-benzyloxymethyl)-pyridin-2-yl]-3-trifluoromethyl-benzenesulfonamide;
3-Chloro-N-(5-cyclopropylmethoxymethyl-pyridin-2-yl)-2-methyl-benzenesulfonamide;
N-(5-Cyclopropyl-methoxymethyl-pyridin-2-yl)-2,5-difluoro-benzenesulfonamide
4-Chloro-N-(5-cyclopropylmethoxymethyl-pyridin-2-yl)-3-methyl-benzenesulfonamide;
N-(5-Cyclopropylmethoxymethyl-pyridin-2-yl)-5-fluoro-2-methyl-benzenesulfonamide;

Piperidine-1-sulfonic acid (5-cyclopropyl-methoxymethyl-pyridin-2-yl)-amide;

3-Chloro-N-(5-cyclopropylmethoxymethyl-6-methyl-pyridin-2-yl)-2-methyl-benzenesulfonamide;

N-(5-Cyclopropylmethoxymethyl-6-methyl-pyridin-2-yl)-2,5-difluoro-benzenesulfonamide;

N-(5-Cyclopropylmethoxymethyl-6-methyl-pyridin-2-yl)-5-fluoro-2-methyl-benzenesulfonamide;

N-(5-Methoxymethyl-6-methyl-pyridin-2-yl)-3-trifluoromethyl-benzenesulfonamide;

3-Chloro-N-(5-methoxymethyl-6-methyl-pyridin-2-yl)-2-methyl-benzenesulfonamide;

N-[5-(4-Fluoro-benzyloxymethyl)-6-methyl-pyridin-2-yl]-3-trifluoromethylbenzenesulfonamide;

3-Chloro-N-[5-(4-fluoro-benzyloxymethyl)-6-methyl-pyridin-2-yl]-2-methylbenzenesulfonamide;

N-(5-Ethoxymethyl-6-methyl-pyridin-2-yl)-3-trifluoromethylbenzenesulfonamide;

3-Chloro-2-methyl-N-{6-[(methyl-propyl-amino)-methyl]-pyridin2-yl}-benzenesulfonamide;

5-Fluoro-2-methyl-N-{6-[(methyl-propyl-amino)-methyl]-pyridin-2-yl}-benzenesulfonamide;

3-Chloro-N-(5-ethoxymethyl-6-methyl-pyridin-2-yl)-2-methyl-benzenesulfonamide;

3-Chloro-N-(6-cyclopropyl-pyridin-2-yl)-2-methyl-benzenesulfonamide;

Naphthalene-1-sulfonic acid (6-cyclopropyl-pyridin-2-yl)-amide;

4-Chloro-N-(6-cyclopropyl-pyridin-2-yl)-2,5-dimethyl-benzenesulfonamide;

4-Chloro-N-(6-cyclopropyl-pyridin-2-yl)-3-methyl-benzenesulfonamide;

N-(6-Gyclopropyl-pyridin-2-yl)-3-trifluoromethyl-benzenesulfonamide;

2,4-Dichloro-N-(6-cyclopropyl-pyridin-2-yl)-5-methylbenzenesulfonamide;

Naphthalene-2-sulfonic acid (6-cyclopropyl-pyridin2-yl)-amide;

N-(5-Cyclopropylmethoxymethyl-pyridin-2-yl)-3-trifluoromethyl-benzenesulfonamide;

N-(5-Ethoxymethyl-6-methyl-pyridin-2-yl)-3,5-bis-trifluoromethyl-benzenesulfonamide;

4-Chloro-N-(5-ethoxymethyl-6-methyl-pyridin-2-yl)-3-trifluoromethyl-benzenesulfonamide;

4-Chloro-N-[6-(4-fluoro-benzyloxymethyl)-pyridin-2-yl]-3-trifluoromethyl-benzenesulfonamide;

4-Chloro-N-[6-(4-fluoro-benzyloxymethyl)-pyridin-2-yl]-2,5-dimethyl-benzenesulfonamide;

3-Trifluoromethyl-N-[6-(4-trifluoromethyl-phenoxymethyl)-pyridin-2-yl]-benzenesulfonamide;

N-[5-(2-Fluoro-ethoxymethyl)-6-methyl-pyridin-2-yl]-3-trifluoromethyl-benzenesulfonamide;

3-Chloro-N-(5-cyclopropylmethoxymethyl-pyridin-2-yl)-benzenesulfonamide;

2,4-Dichloro-N-(5-cyclopropylmethoxymethyl-pyridin-2-yl)-6-methyl-benzenesulfonamide;

N-(5-Cyclopropylmethoxymethyl-pyridin-2-yl)-4-fluoro-3-trifluoromethyl-benzenesulfonamide;

3-Chloro-N-(5-cyclopropylmethoxymethyl-6-methyl-pyridin-2-yl)-benzenesulfonamide;

2,4-Dichloro-N-(5-cyclopropylmethoxymethyl-6-methyl-pyridin-2-yl)-6-methyl-benzenesulfonamide;

N-(5-Cyclopropylmethoxymethyl-6-methyl-pyridin-2-yl)-3-trifluoromethyl-benzenesulfonamide;

2,4-Difluoro-N-[6-(3-fluoro-benzyloxymethyl)-pyridin-2-yl]-benzenesulfonamide;

3-Chloro-N-[6-(3-fluoro-benzyloxymethyl)-pyridin-2-yl]-benzenesulfonamide;

2,4-Dichloro-N-[6-(3-fluoro-benzyloxymethyl)-pyridin-2-yl]-6-methyl-benzenesulfonamide;

2,4-Difluoro-N-[6-(4-fluoro-benzyloxymethyl)-pyridin-2-yl]-benzenesulfonamide;

3-Chloro-N-[6-(4-fluoro-benzyloxymethyl)-pyridin-2-yl]-benzenesulfonamide;

2,4-Dichloro-N-[6-(4-fluoro-benzyloxymethyl)-pyridin-2-yl]-6-methyl-benzenesulfonamide;

N-(5-Cyclopropylmethoxymethyl-6-methyl-pyridin-2-yl)-4-fluoro-3-trifluoromethyl-benzenesulfonamide;

4-Fluoro-N-[6-(3-fluoro-benzyloxymethyl)-pyridin-2-yl]-3-trifluoromethyl-benzenesulfonamide;

4-Fluoro-N-[6-(4-fluoro-benzyloxymethyl)-pyridin-2-yl]-3-trifluoromethyl-benzenesulfonamide;

N-[6-(4-Fluoro-benzyloxymethyl)-pyridin-2-yl]-3-trifluoromethoxy-benzenesulfonamide;

N-(6-Methoxymethyl-pyridin-2-yl)-3-trifluoromethyl-benzenesulfonamide;

2,4-Dichloro-N-(6-methoxymethyl-pyridin-2-yl)-6-methyl-benzenesulfonamide;

3-Chloro-N-(6-methoxethyl-pyridin-2-yl)-benzenesulfonamide;

3-Trifluoromethyl-N-[6-(3,3,3-trifluoro-propoxymethyl)-pyridin-2-yl]-benzenesulfonamide;

2,4-Dichloro-6-methyl-N-[6-(3,3,3-trifluoro-propoxymethyl)-pyridin-2-yl]-benzenesulfonamide;

N-[6-(2,2,2-Trifluoro-ethoxymethyl)-pyridin-2-yl]-3-trifluoromethyl-benzenesulfonamide;

2,4-Dichloro-6-methyl-N-[6-(2,2,2-trifluoro-ethoxymethyl)-pyridin-2-yl]-benzenesulfonamide;

3-Chloro-N-[6-(2-cyclopropyl-ethoxymethyl)-pyridin-2-yl]-benzenesulfonamide;

N-[6-(2-Cyclopropyl-ethoxymethyl)-pyridin-2-yl]-3-trifluoromethyl-benzenesulfonamide;

N-[6-(2-Cyclopropyl-ethoxymethyl)-pyridin-2-yl]-4-fluoro-3-trifluoromethyl-benzenesulfonamide;

2,4-Dichloro-N-[6-(2-cyclopropyl-ethoxymethyl)-pyridin-2-yl]-6-methyl-benzenesulfonamide;

2,4-Dichloro-5-methyl-N-[6-(2,2,2-trifluoro-ethoxymethyl)-pyridin-2-yl]-benzenesulfonamide;

2-Chloro-N-[6-(2,2,2-trifluoro-ethoxymethyl)-pyridin-2-yl]-5-trifluoromethyl-benzenesulfonamide;

2,4-Dichloro-N-[6-(3-chloro-benzyloxymethyl)-pyridin-2-yl]-6-methyl-benzenesulfonamide;

N-[6-(3-Chloro-benzyloxymethyl)-pyridin-2-yl]-4-fluoro-3-trifluoromethyl-benzenesulfonamide;

N-[6-(4-Chloro-benzyloxymethyl)-pyridin-2-yl]-4-fluoro-3-trifluoromethyl-benzenesulfonamide;

2,4-Dichloro-N-[6-(4-chloro-benzyloxymethyl)-pyridin-2-yl]-6-methyl-benzenesulfonamide;

N-[5-(2,2,2-Trifluoro-ethoxymethyl)-pyridin-2-yl]-3-trifluoromethyl-benzenesulfonamide;

2,4-Dichloro-5-methyl-N-[5-(2,2,2-trifluoro-ethoxymethyl)-pyridin-2-yl]-benzenesulfonamide;

3-Chloro-2-methyl-N-(3,4,5,6-tetrahydro-2H-[1,3']bipyridinyl-6'-yl)-benzenesulfonamide;

3-Chloro-2-methyl-N-(5-pyrrolidin-1-yl-pyridin-2-yl)-benzenesulfonamide;

3-Chloro-2-methyl-N-(5-morpholin-4-yl-pyridin-2-yl)-benzenesulfonamide;

N-(5-Benzyl-pyridin-2-yl)-3-chloro-2-methyl-benzenesulfonamide;

3-Chloro-2-methyl-N-(5-phenethyl-pyridin-2-yl)-benzenesulfonamide;

3-Chloro-2-methyl-N-(6-methyl-5-phenethyl-pyridin-2-yl)-benzenesulfonamide;
3-Chloro-2-methyl-N-(5-thiomorpholin-4-yl-pyridin-2-yl)-benzenesulfonamide;
2,4-Dichloro-N-{5-[2-(4-chloro-phenyl)-ethyl]-pyridin-2-yl}-6-methyl-benzenesulfonamide;
3-Chloro-N-{5-[2-(4-methoxy-phenyl)-ethyl]-pyridin-2-yl}-2-methyl-benzenesulfonamide;
3-Chloro-N-{5-[2-(3-fluoro-phenyl)-ethyl]-pyridin-2-yl}-2-methyl-benzenesulfonamide;
3-Chloro-2-methyl-N-{5-[2-(2-trifluoromethyl-phenyl)-ethyl]-pyridin-2-yl}-benzenesulfonamide
3-Chloro-N-{5-[2-(4-fluoro-phenyl)-ethyl]-pyridin-2-yl}-2-methyl-benzenesulfonamide;
3-Chloro-2-methyl-N-(5-phenoxy-pyridin-2-yl)-benzenesulfonamide;
3-Chloro-N-[5-(2-chloro-phenoxy)-pyridin-2-yl]-2-methyl-benzenesulfonamide;
3-Chloro-N-[5-(4-fluoro-phenoxy)-pyridin-2-yl]-2-methyl-benzenesulfonamide;
2,4-Dichloro-6-methyl-N-(5-phenoxy-pyridin-2-yl)-benzenesulfonamide;
2,4-Dichloro-N-[5-(2-chloro-phenoxy)-pyridin-2-yl]-6-methyl-benzenesulfonamide;
2,4-Dichloro-N-[5-(4-fluoro-phenoxy)-pyridin-2-yl]-6-methyl-benzenesulfonamide;
3-Chloro-2-methyl-N-[5-(2-quinolin-2-yl-ethyl)-pyridin-2-yl]-benzenesulfonamide;
2,4-Dichloro-6-methyl-N-[5-(2-quinolin-2-yl-ethyl)-pyridin-2-yl]-benzenesulfonamide; and
3-Chloro-2-methyl-N-[5-(2-pyridin-2-yl-ethyl)-pyridin-2-yl]-benzenesulfonamide.

Examples of particularly preferred compounds of formula (I) are:
3-Chloro-N-(6-ethyl-pyridin-2-yl)-2-methyl-benzenesulfonamide;
Biphenyl-4-sulfonic acid (6-propyl-pyridin-2-yl)-amide;
3-Chloro-2-methyl-N-(6-propyl-pyridin-2-yl)-benzenesulfonamide;
2,4-Dichloro-6-methyl-N-(6-propyl-pyridin-2-yl)-benzenesulfonamide;
5-Chloro-naphthalene-2-sulfonic acid (6-propyl-pyridin-2-yl)-amide;
3-Chloro-N-(6-isopropyl-pyridin-2-yl)-4-methyl-benzenesulfonamide;
N-(6-Isopropyl-pyridin-2-yl)-3-trifluoromethyl-benzenesulfonamide;
3-Chloro-2-methyl-N-[6-(2-trifluoromethyl-phenyl)-pyridin-2-yl]-benzenesulfonamide;
2,5-Difluoro-N-[6-(4-fluoro-2-methyl-phenyl)-pyridin-2-yl]-benzenesulfonamide;
2,4-Dichloro-N-[6-(4-fluoro-2-methyl-phenyl)-pyridin-2-yl]-6-methyl-benzenesulfonamide;
2-[6-(3-Chloro-2-methyl-benzenesulfonylamino)-pyridin-2-yl]-N,N-diethyl-acetamide;
3-Chloro-N-(6-hydroxymethyl-pyridin-2-yl)-2-methyl-benzenesulfonamide;
3-Chloro-N-(6-methoxymethyl-pyridin-2-yl)-2-methyl-benzenesulfonamide;
3-Chloro-N-(6-cyclopropylmethoxymethyl-pyridin-2-yl)-2-methyl-benzenesulfonamide;
3,4-Dichloro-N-(6-cyclopropylmethoxymethyl-pyridin-2-yl)-benzenesulfonamide;
4-Fluoro-N-[6-(4-fluoro-benzyloxymethyl)-pyridin-2-yl]-benzenesulfonamide;
N-[6-(4-Fluoro-benzyloxymethyl)-pyridin-2-yl]-3-trifluoromethyl-benzenesulfonamide;
3-Chloro-N-(5-cyclopropylmethoxymethyl-pyridin-2-yl)-2-methyl-benzenesulfonamide;
3-Chloro-N-(5-cyclopropylmethoxymethyl-6-methyl-pyridin-2-yl)-2-methyl-benzenesulfonamide;
3-Chloro-N-(5-methoxymethyl-6-methyl-pyridin-2-yl)-2-methyl-benzenesulfonamide;
N-(5-Ethoxymethyl-6-methyl-pyridin-2-yl)-3-trifluoromethylbenzenesulfonamide;
3-Chloro-N-(6-cyclopropyl-pyridin-2-yl)-2-methyl-benzenesulfonamide;
Naphthalene-1-sulfonic acid (6-cyclopropyl-pyridin-2-yl)-amide;
4-Chloro-N-(6-cyclopropyl-pyridin-2-yl)-2,5-dimethyl-benzenesulfonamide;
N-(6-Cyclopropyl-pyridin-2-yl)-3-trifluoromethyl-benzenesulfonamide;
N-(5-Cyclopropylmethoxymethyl-pyridin-2-yl)-3-trifluoromethyl-benzenesulfonamide;
4-Chloro-N-(5-ethoxymethyl-6-methyl-pyridin-2-yl)-3-trifluoromethyl-benzenesulfonamide;
2,4-Dichloro-N-(5-cyclopropylmethoxymethyl-pyridin-2-yl)-6-methyl-benzenesulfonamide;
N-(5-Cyclopropylmethoxymethyl-pyridin-2-yl)-4-fluoro-3-trifluoromethyl-benzenesulfonamide;
2,4-Dichloro-N-(5-cyclopropylmethoxymethyl-6-methyl-pyridin-2-yl)-6-methyl-benzenesulfonamide;
N-(5-Cyclopropylmethoxymethyl-6-methyl-pyridin-2-yl)-3-trifluoromethyl-benzenesulfonamide;
2,4-Dichloro-N-[6-(4-fluoro-benzyloxymethyl)-pyridin-2-yl]-6-methyl-benzenesulfonamide;
4-Fluoro-N-[6-(4-fluoro-benzyloxymethyl)-pyridin-2-yl]-3-trifluoromethyl-benzenesulfonamide;
N-[6-(4-Fluoro-benzyloxymethyl)-pyridin-2-yl]-3-trifluoromethoxy-benzenesulfonamide;
N-(6-Methoxymethyl-pyridin-2-yl)-3-trifluoromethyl-benzenesulfonamide;
3-Trifluoromethyl-N-[6-(3,3,3-trifluoro-propoxymethyl)-pyridin-2-yl]-benzenesulfonamide;
2,4-Dichloro-6-methyl-N-[6-(3,3,3-trifluoro-propoxymethyl)-pyridin-2-yl]-benzenesulfonamide;
2,4-Dichloro-6-methyl-N-[6-(2,2,2-trifluoro-ethoxymethyl)-pyridin-2-yl]-benzenesulfonamide;
2,4-Dichloro-N-[6-(2-cyclopropyl-ethoxymethyl)-pyridin-2-yl]-6-methyl-benzenesulfonamide;
2,4-Dichloro-N-[6-(3-chloro-benzyloxymethyl)-pyridin-2-yl]-6-methyl-benzenesulfonamide;
N-[6-(4-Chloro-benzyloxymethyl)-pyridin-2-yl]-4-fluoro-3-trifluoromethyl-benzenesulfonamide;
2,4-Dichloro-N-[6-(4-chloro-benzyloxymethyl)-pyridin-2-yl]-6-methyl-benzenesulfonamide;
3-Chloro-2-methyl-N-(3,4,5,6-tetrahydro-2H-[1,3']bipyridinyl-6'-yl)-benzenesulfonamide;
3-Chloro-2-methyl-N-(5-pyrrolidin-1-yl-pyridin-2-yl)-benzenesulfonamide;
3-Chloro-2-methyl-N-(5-morpholin-4-yl-pyridin-2-yl)-benzenesulfonamide;
N-(5-Benzyl-pyridin-2-yl)-3-chloro-2-methyl-benzenesulfonamide;
3-Chloro-2-methyl-N-(6-methyl-5-phenethyl-pyridin-2-yl)-benzenesulfonamide;
3-Chloro-2-methyl-N-(5-thiomorpholin-4-yl-pyridin-2-yl)-benzenesulfonamide;
2,4-Dichloro-N-{5-[2-(4-chloro-phenyl)-ethyl]-pyridin-2-yl}-6-methyl-benzenesulfonamide;
3-Chloro-N-{5-[2-(3-fluoro-phenyl)-ethyl]-pyridin-2-yl}-2-methyl-benzenesulfonamide;

3-Chloro-N-{5-[2-(4-fluoro-phenyl)-ethyl]-pyridin-2-yl}-2-methyl-benzenesulfonamide;
3-Chloro-2-methyl-N-(5-phenoxy-pyridin-2-yl)-benzenesulfonamide;
3-Chloro-N-[5-(2-chloro-phenoxy)-pyridin-2-yl]-2-methyl-benzenesulfonamide;
3-Chloro-N-[5-(4-fluoro-phenoxy)-pyridin-2-yl]-2-methyl-benzenesulfonamide;
2,4-Dichloro-6-methyl-N-(5-phenoxy-pyridin-2-yl)-benzenesulfonamide;
2,4-Dichloro-N-[5-(2-chloro-phenoxy)-pyridin-2-yl]-6-methyl-benzenesulfonamide; and
2,4-Dichloro-N-[5-(4-fluoro-phenoxy)-pyridin-2-yl]-6-methyl-benzenesulfonamide.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

In general, compounds of type I are readily accessible by sulfonylation of appropriately substituted 2-amino-pyridines of formula II with sulfonyl chlorides under various conditions that are known to persons skilled in the art. Examples of such conditions are—as indicated in Scheme 1 below—e.g. pyridine at elevated temperatures or THF under reflux conditions in the presence of a base such as potassium carbonate, sodium carbonate, sodium hydride, triethyl amine or the like.

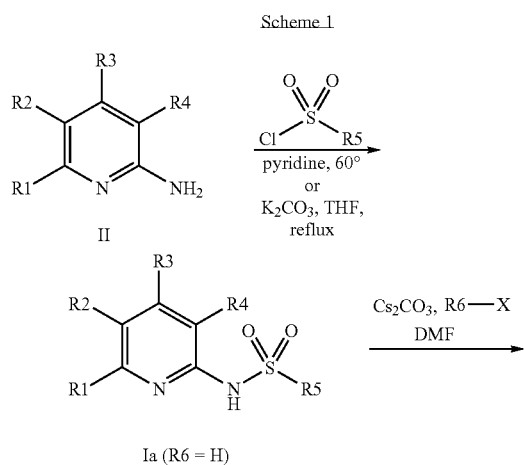

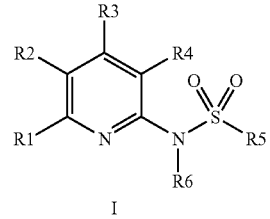

X means Cl, Br or I

Optionally, compounds of formula Ia with $R^6$ is H obtained in this way can be further substituted at the sulfonamide nitrogen by treatment with a base such as sodium hydride, cesium carbonate, potassium carbonate or the like in a solvent such as DMF or THF or similar followed by alkylation of the resulting anion with an alkyl halide such as methyl iodide, ethyl bromide, benzyl bromide or the like in order to introduce the desired $R^6$ substituent.

Appropriately substituted 2-amino-pyridines of formula II are either commercially available, are known in the literature or can be made in analogy to literature procedures from known starting materials. General approaches that have been used for the synthesis of various aminopyridines of general formula II in the course of this invention are outlined below.

2-Aminopyridines of formula IIb with $R^1$ is alkyl, cycloalkyl, aryl or heterocyclyl can be made according to scheme 2 from compounds of formula III via metal-catalysed (Pd or Ni) cross-coupling reaction with corresponding organometallic reagent such as heterocyclyl-, alkyl-, cycloalkyl or aryl-boron, -zinc or -tin reagents using Suzuki-, Stille- or Negishi-type coupling reactions (for literature: Suzuki, Chem. Rev., 1995, 95, 2475; Stille, Angew. Chem. IEE, 1986, 25, 508; Negishi, Acc. Chem. Res., 1982, 15, 340). The corresponding organometallic reagents used are either commercially available, known in the literature or were prepared according to standard procedures known in the art. Compounds of formula IIc with R1=aminocarbonylmethyl can be prepared according to scheme 2 from compounds IV, selective lithiation with for example lithium diisopropylamide (LDA) in THF, addition of $CO_2$ (dry ice) to give compounds of formula V. Subsequent coupling with appropriate amines in the presence of a coupling reagent such as benzotriazol-1-yloxytris(dimethylamino)phosphonium hexafluorophosphate (BOP) in acetonitrile gives compounds of formula VI, which are then de-protected with trifluoro-acetic acid in a solvent such as methylene chloride to give compounds of formula IIc.

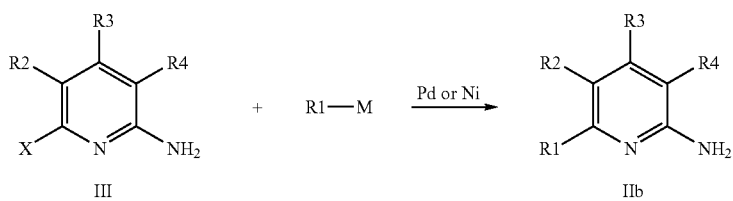

R1: alkyl, cycloalkyl, aryl, heterocyclyl

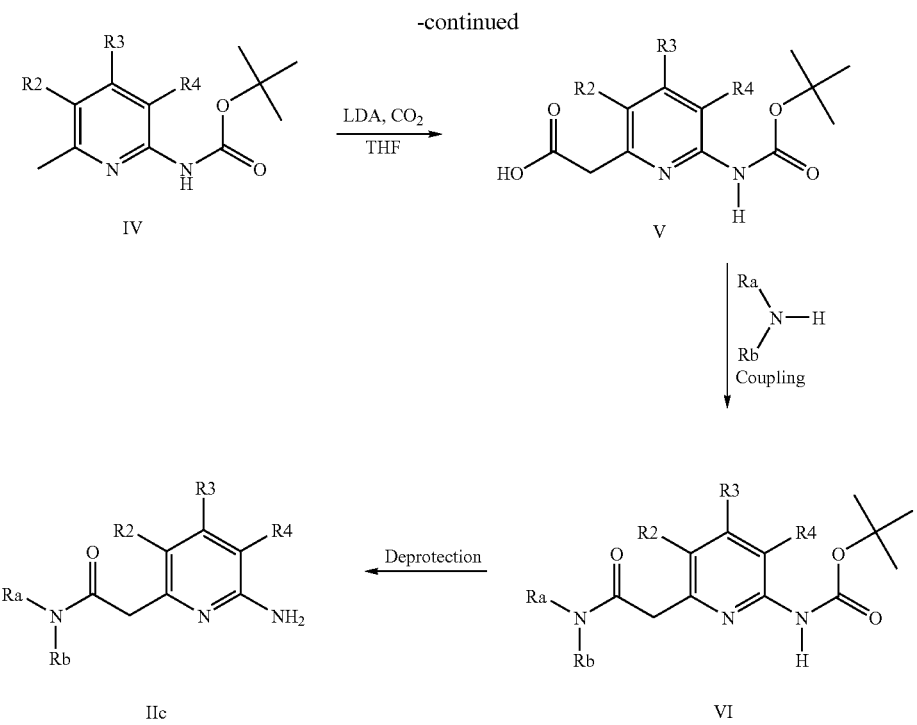

X = I, Br, Cl
M = B(OH)$_2$, SnR$_3$, ZnBr or Zn—R1
(Ra)(Rb)N- means amino as defined before Compounds of formula IId with R1=alkoxycarbonylmethyl can be prepared according to scheme 3 from protected 2-amino-6-methyl pyridines of formula VII by selective lithiation with for example with LDA, subsequent addition of CO$_2$ followed by standard esterification reactions, for example with an alcohol as solvent in the presence of thionyl chloride or with an alcohol in a suitable solvent in the presence of acid, or by applying a coupling reagent as discussed above, under simultaneous removal of the trimethylsilyl protecting groups when acidic reaction conditions are applied, to give compounds of formula IId.

Compounds of formula IIe with R1 is alkylcarbonylmethyl can be obtained from VII via lithiation with N-butyllithium (BuLi), subsequent reaction with an appropriate alkyl nitrile and an acidic work-up to yield IIe. Alternatively, compounds of formula IIc-d can be prepared from compounds of formula VIII, obtained from Ib via lithiation with LDA and CO$_2$ addition, by standard esterification or amide formation reactions known in the art. Next higher homologues of above described amines of formula II, such as aminocarbonyl ethyl as R1 and the like, can be prepared from intermediates described in schemes 2,3 via homologation reactions known in the art, e.g. via Arndt-Eistert synthesis starting with compounds of formula V to give analogues with aminocarbonyl ethyl as R1.

Scheme 3

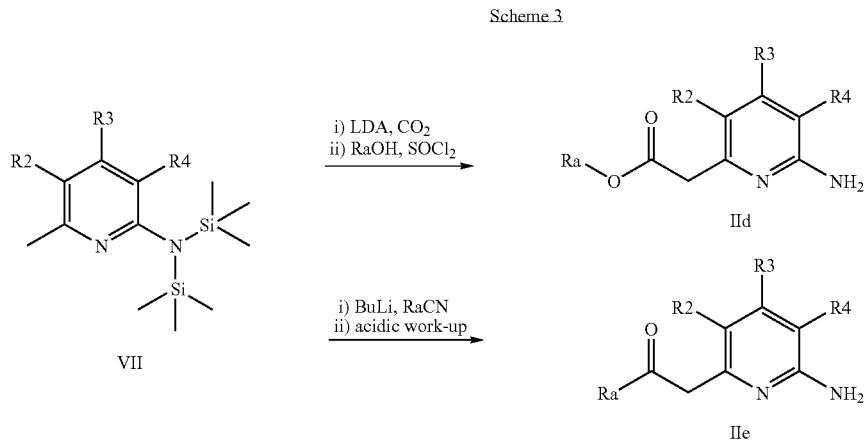

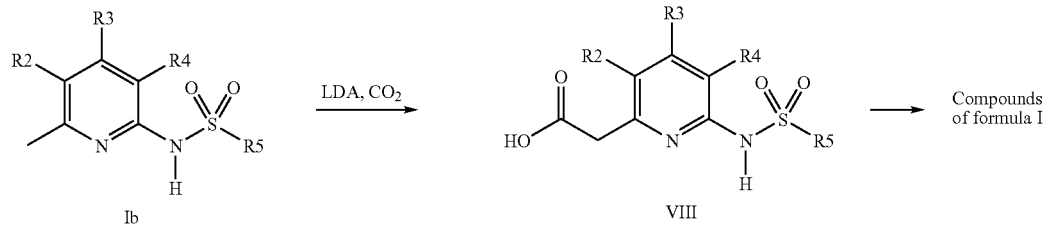

Ra = alkyl

Compounds of formula IIf with R1 is alkoxymethyl, heterocyclylalkoxymethyl, cycloalkylalkoxyalkyl, arylalkoxymethyl, aryloymethyl, haloalkoxymethyl and the like can be prepared according to scheme 4 starting from compounds of formula IX. Accordingly, de-protonation of IX with NaH in THF and subsequent reaction with an alkyl, arylalkyl or heterocyclylalkyl halide and the like gives rise to compound of formula X. Upon hydrolysis with a base such as aqueous 3N NaOH at elevated temperature compounds of formula IIf are obtained. The aryloxymethyl analogues are prepared from X via Mitsunobu reaction.

Alternatively, intermediates of formula X can be obtained from XI via reaction with an appropriate alcohol ROH in the presence of a base such as NaH and in THF as solvent. Compounds of formula XI are obtained form IX via reaction with thionyl chloride. Compounds of formula IIg with R1=aminomethyl and the like can be prepared from XI upon reaction with an appropriate amine in acetone as solvent, in the presence of $KHCO_3$ as base and with catalytic amounts of potassium iodide, to give XII that can subsequently be deprotected to give IIg.

Intermediates of scheme 4 can also be converted to the next higher homologues as mentioned above and as known to persons skilled in the art.

Scheme 4

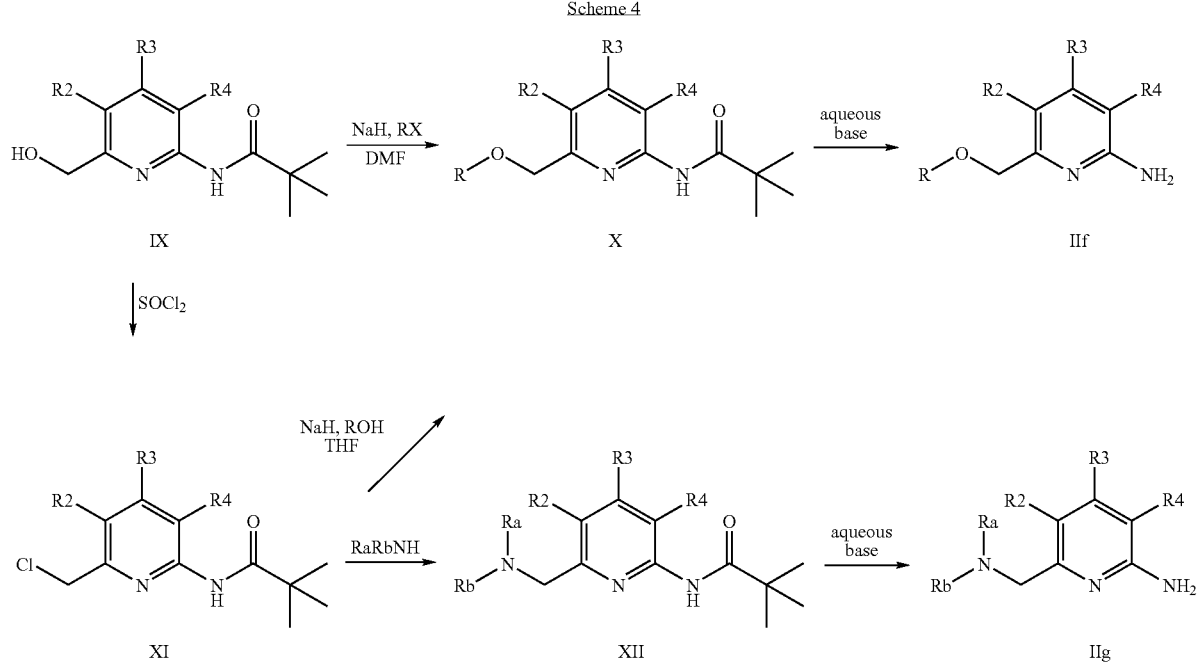

R means e.g. alkyl, haloalkyl, heterocyclylalkyl or arylalkyl
(Ra)(Rb)N- means amino as defined before Compounds of formula IIh with R2 is cycloalkyloxymethyl, alkoxymethyl, arylalkoxymethyl, haloalkoxymethyl can be prepared according to scheme 5 from compounds of formula XIII via halogen lithium exchange with BuLi, reaction with DMF to give XIV, followed by NaBH$_4$ reduction to yield XV. Functionalization reactions are then carried out in analogy to the reaction sequences discussed above, either via reacting XV with appropriate alkyl halogenids in the presence of NaH to give compounds of formula XVI, or from XVII via reaction with ROH and with NaH. XVII can be obtained from XV via treatment with thionyl chloride. Again, all intermediates can be used as already discussed above to make the next higher homologues.

Scheme 6

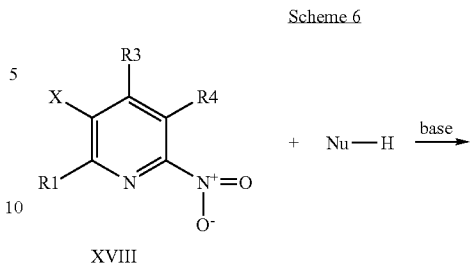

Scheme 5

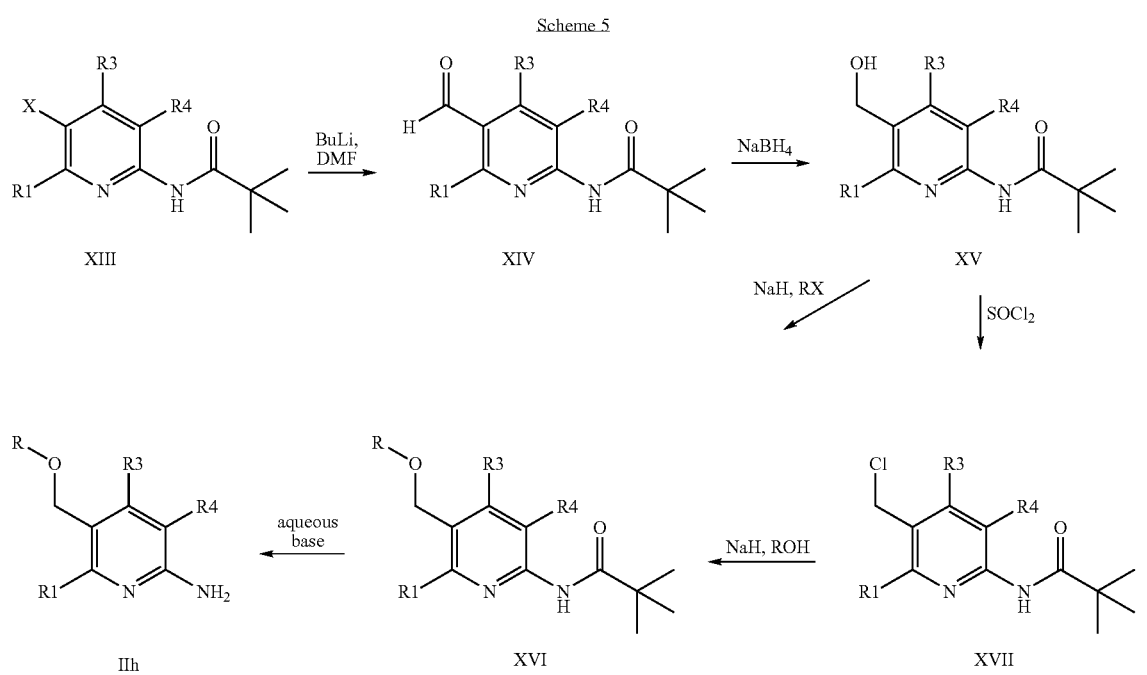

R means e.g. alkyl, haloalkyl, cycloalkylalkyl or arylalkyl
X means Cl, Br or I

2-Aminopyridines of type IIi in which R2 is represented by a nudeophile Nu that is defined as outlined in Scheme 6—e.g. a phenol or an amine—can be made in the following way: An appropriately substituted 5-halo-2-nitropyridine of formula XVIII is treated with an appropriate nuclephile—e.g. a phenol or an amine or the like—in the presence of a base such as sodium hydride, potassium carbonate or the like in a suitable solvent such as DMF, DMSO, THF or similar at temperatures ranging from 0° C. to 200° C. to give nitropyridine XIX. The nitro group present in compound XIX can be reduced using standard reduction conditions such as catalytic hydrogenation in the presence of a suitable catalyst such as Pd, Pt or the like or alternative conditions such as Sn(II)Cl$_2$ in the presence of an acid such as HCl, HBr or the like to give the desired 2-aminopyridines IIi that can be treated in subsequent reaction steps as outlined in Scheme 1 to give sulfonamides of formula Ia and/or I.

-continued

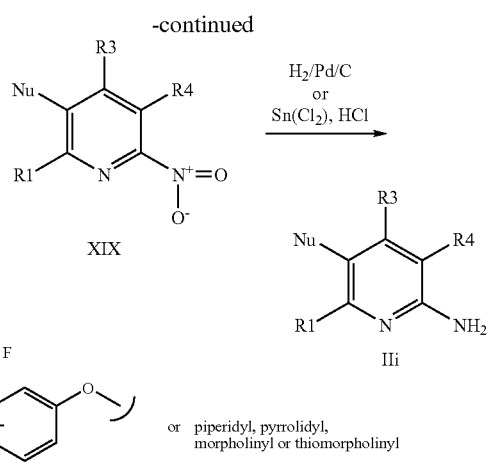

X = I, Br, Cl, F

Nu = R'—[phenol] or piperidyl, pyrrolidyl, morpholinyl or thiomorpholinyl

R' means e.g. halogen, alkyl, amino or haloalkyl

2-Aminopyridines of type IIj in which R2 is represented by a (hetero)aryl-ethyl side chain as shown in Scheme 7 are made in the following way: An appropriately substituted 2-amino-5-halo-pyridine of formula XX is subjected to a Heck-type reaction in the presence of an appropriately substituted styrene or vinyl-(hetero)aromate under conditions that are known in the literature (see e.g. Heck et al., J. Am. Chem. Soc. 1968, 90, 5518) to furnish intermediate XXI. The double bond that is present in this material can optionally be reduced using conditions such as catalytic hydrogenation with various catalysts such as Pd, Pt or the like to give the desired 2-aminopyridines IIj that can be used in subsequent reaction steps as outlined in Scheme 1 to give compounds of formula Ia and/or I.

Scheme 7

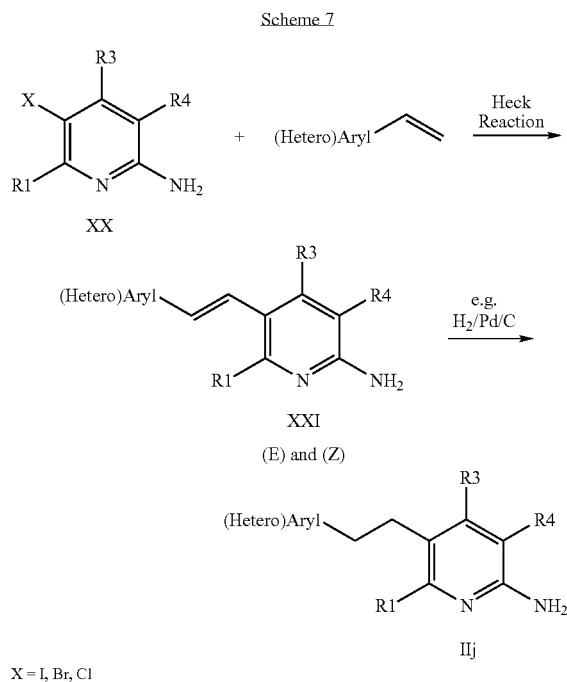

X = I, Br, Cl

Preferred is the process for the preparation of a compound according to formula I comprising reaction of a compound according to formula

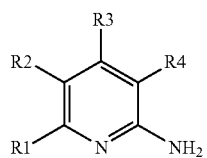

II in the presence of a compound according to formula

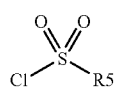

in order to obtain a compound of the formula

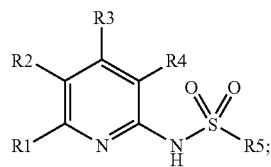

Ia and optionally further reaction in the presence of a compound of the formula R$^6$—X in order to obtain a compound of the formula

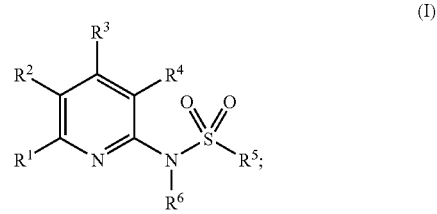

(I)

wherein R$^1$ to R$^6$ are defined as before and X is Cl, Br or I. Particularly preferred is the above reaction a) in the presence of pyridine or THF and particularly in the presence of a base such as e.g. potassium carbonate, sodium carbonate, sodium hydride or triethyl amine. Particularly preferred is the above reaction b) in the presence of sodium hydride, cesium carbonate, potassium carbonate particularly in DMF or THF. Preferred examples of compounds according to formula R$^6$—X are methyl iodide and ethyl bromide.

Preferred intermediates are:
6-Isopropyl-pyridin-2-ylamine;
6-(2-Chloro-phenyl)-pyridin-2-ylamine;
6-(2,4-Difluoro-phenyl)-pyridin-2-ylamine;
6-(3-Fluoro-phenyl)-pyridin-2-ylamine;
6-(2,3-Difluoro-phenyl)-pyridin-2-ylamine;
6-(2,5-Dichloro-phenyl)-pyridin-2-ylamine;
6-(3-Chloro-phenyl)-pyridin-2-ylamine;
6-(2-Fluoro-phenyl)-pyridin-2-ylamine;
6-(2-Trifluoromethyl-phenyl)-pyridin-2-ylamine;
6-(2-Methoxy-phenyl)-pyridin-2-ylamine;
6-(4-Fluoro-2-methyl-phenyl)-pyridin-2-ylamine;
[2,3']Bipyridinyl-6-ylamine;
6-Ethylsulfanyl-pyridin-2-ylamine;
1-(6-Amino-pyridin-2-yl)-pentan-2-one;
(6-Amino-pyridin-2-yl)-acetic acid methyl ester;
2-(6-Amino-pyridin-2-yl)-N,N-diethyl-acetamide;
2-(6-Amino-3-methyl-pyridin-2-yl)-N,N-diethyl-acetamide;
6-Cyclopropylmethoxymethyl-pyridin-2-ylamine;
6-(4-Fluoro-benzyloxymethyl)-pyridin-2-ylamine;
6-(4-Trifluoromethyl-phenoxymethyl)-pyridin-2-ylamine;
5-Cyclopropylmethoxymethyl-pyridin-2-ylamine;
5-Cyclopropylmethoxymethyl-6-methyl-pyridin-2-ylamine;
5-Methoxymethyl-6-methyl-pyridin-2-ylamine;
5-(4-Fluoro-benzyloxymethyl)-6-methyl-pyridin-2-ylamine;
5-Ethoxymethyl-6-methyl-pyridin-2-ylamine;
6-[(Methyl-propyl-amino)-methyl]-pyridin-2-ylamine;
6-Cyclopropyl-pyridin-2-ylamine;
5-(2-Fluoro-ethoxymethyl)-6-methyl-pyridin-2-ylamine;
6-(3-Fluoro-benzyloxymethyl)-pyridin-2-ylamine;

6-(3,3,3-Trifluoro-propoxymethyl)-pyridin-2-ylamine;
6-(2,2,2-Trifluoro-ethoxymethyl)-pyridin-2-ylamine;
6-(2-Cyclopropyl-ethoxymethyl)-pyridin-2-ylamine;
6-(3-Chloro-benzyloxymethyl)-pyridin-2-ylamine;
6-(4-Chloro-benzyloxymethyl)-pyridin-2-ylamine;
5-(2,2,2-Trifluoro-ethoxymethyl)-pyridin-2-ylamine;
3,4,5,6-Tetrahydro-2H-[1,3']bipyridinyl-6'-ylamine;
6-Methyl-5-phenethyl-pyridin-2-ylamine and
5-Phenoxy-pyridin-2-ylamine.

The compounds of formula I described above for use as therapeutically active substance are an embodiment of the invention.

Also, an embodiment of the present invention are compounds as described above for the preparation of medicaments for the prophylaxis and therapy of illnesses which are caused by disorders associated with the enzyme 11beta-hydroxysteroid dehydrogenase1 (11bHSD1).

Likewise, an embodiment of the invention are pharmaceutical compositions comprising a compound of the formula I as described above and a therapeutically inert carrier.

A further preferred embodiment of the present invention is the use of a compound of the formula I as described above for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

The invention is useful as a method for the treatment and prophylaxis of diabetes, obesity, eating disorders, dyslipidemiae and hypertension, which method comprises administering an effective amount of a compound of formula I as described above.

Particularly preferred is a method for the treatment and prophylaxis of diabetes Type II, which method comprises administering an effective amount of a compound according to formula I as described above.

Compounds as described above have $IC_{50}$ values below 1000 nM; preferred compounds have $IC_{50}$ values below 100 nM. More preferred compounds have $IC_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragees and hard gelatin capsules. Lactose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case.

In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character. Examples 1 to 5, 8, 11 to 14, 16 and 17 are included for preparation purpose and are not covered by claim 1.

EXAMPLES

Example 1

Naphthalene-2-sulfonic acid
(6-methyl-pyridin-2-yl)-amide

6-Methyl-pyridin-2-ylamine (1 g) and 2-naphthalenesulfonyl chloride (2.3 g) were dissolved in pyridine (5 mL) and the resulting mixture was allowed to stir at RT for 12 hours. After concentration in vacuo the residue was taken up in EtOAc, the solution washed with 1 N aqueous HCl, saturated brine then dried over sodium sulphate and concentrated in vacuo. The residue was purified by flash chromatography (heptane/EtOAc 5:1) to give the desired product naphthalene-2-sulfonic acid (6-methyl-pyridin-2-yl)-amide as a white foam (2.18 g). MS (ESI$^-$): 297.2 ([M–H]$^-$).

Example 2

N-(6-Methyl-pyridin-2-yl)-4-nitro-benzenesulfonamide

This material was obtained in analogy to example 1 from 6-methyl-pyridin-2-ylamine with 4-nitro-benzenesulfonyl chloride as a yellow solid. MS (ESI$^-$): 292.0 ([M–H]$^-$).

Example 3

N-[4-(6-Methyl-pyridin-2-ylsulfamoyl)-phenyl]-acetamide

This material was obtained in analogy to example 1 from 6-methyl-pyridin-2-ylamine and 4-acetamido-benzenesulfonyl chloride as a white solid. MS (ESI$^-$): 304.0 ([M–H]$^-$).

Example 4

3-Chloro-2-methyl-N-(6-methyl-pyridin-2-yl)-benzenesulfonamide

This material was obtained in analogy to example 1 from 6-methyl-pyridin-2-ylamine (0.108 g) and 3-chloro-2methyl-benzenesulfonyl chloride (0.259 g) as an off-white crystalline solid (0.24 g). MS (ESI$^-$): 295.1 ([M–H]$^-$).

Example 5

Biphenyl-4-sulfonic acid (6-methyl-pyridin-2-yl)-amide

This material was obtained in analogy to example 1 from 6-methyl-pyridin-2-ylamine (0.108 g) and biphenyl-4-sulfonyl chloride (0.278 g) as an off-white crystalline solid (0.157 g). MS (ESI$^-$): 323.2 ([M–H]$^-$).

Example 6

3-Chloro-N-(6-ethyl-pyridin-2-yl)-2-methyl-benzenesulfonamide

This material was obtained in analogy to example 1 from 6-ethyl-pyridin-2-ylamine (0.25 g) and 3-chloro-2-methyl-benzenesulfonyl chloride (0.5 g) as a white solid (0.13 g). MS (ESI$^-$): 309.1 ([M–H]$^-$).

Example 7

Biphenyl-4-sulfonic acid (6-ethyl-pyridin-2-yl)-amide

This material was obtained in analogy to example 1 from 6-ethyl-pyridin-2-ylamine (0.25 g) and biphenyl-4-sulfonyl chloride (0.57 g) as a white foam (0.156 g). MS (ESI$^-$): 337.1 ([M–H]$^-$)

Example 8

5-Fluoro-2-methyl-N-(6-methyl-pyridin-2-yl)-benzenesulfonamide

This material was obtained in analogy to example 1 from 6-methyl-pyridin-2-ylamine (0.2 g) and biphenyl-4-sulfonyl chloride (0.42 g) as a yellow solid (0.132 g). MS (ESI$^-$): 278.9 ([M–H]$^-$).

Example 9

Biphenyl-4-sulfonic acid (6-propyl-pyridin-2-yl)-amide

This material was obtained in analogy to example 1 from 6-propyl-pyridin-2-ylamine (0.2 g) and biphenyl-4-sulfonyl chloride (0.408 g) as an off-white solid (0.132 g). MS (ESI$^-$): 351.2 ([M–H]$^-$).

Example 10

3-Chloro-2-methyl-N-(6-propyl-pyridin-2-yl)-benzenesulfonamide

This material was obtained in analogy to example 1 from 6-propyl-pyridin-2-ylamine (0.2 g) and 3-chloro-2methyl-benzenesulfonyl chloride (0.386 g) as a white solid (0.34 g). MS (ESI$^-$): 323.2 ([M–H]$^-$).

Example 11

3-Chloro-N-(4,6-dimethyl-pyridin-2-yl)-2-methyl-benzenesulfonamide

This material was obtained in analogy to example 1 from 4,6-dimethyl-pyridin-2-ylamine and 3-chloro-2methyl-benzenesulfonyl chloride as a light yellow solid. MS (ESI$^-$): 309.1 ([M–H]$^-$).

Example 12

Biphenyl-4-sulfonic acid (4,6-dimethyl-pyridin-2-yl)-amide

This material was obtained in analogy to example 1 from 4,6-dimethyl-pyridin-2-ylamine and biphenyl-4-sulfonyl chloride as a white amorphous solid. MS (ESI$^-$): 337.0 ([M–H]$^-$).

Example 13

N-(3-Bromo-6-methyl-pyridin-2-yl)-3-chloro-2-methyl-benzenesulfonamide

This material was obtained in analogy to example 1 from 3-bromo-6-methyl-pyridin-2-ylamine (0.2 g) and 3-chloro-2-methyl-benzenesulfonyl chloride (0.265 g) as an off-white solid (0.351 g). MS (ESI$^-$): 372.9 ([M–H]$^-$).

Example 14

Biphenyl-4-sulfonic acid (3-bromo-6-methyl-pyridin-2-yl)-amide

This material was obtained in analogy to example 1 from 3-bromo-6-methyl-pyridin-2-ylamine (0.2 g) and biphenyl-4-sulfonyl chloride (0.297 g) as a white foam (0.307 g). MS (ESI$^-$): 401.2 ([M–H]$^-$).

Example 15

Naphthalene-2-sulfonic acid (6-propyl-pyridin-2-yl)-amide

This material was obtained in analogy to example 1 from 6-propyl-pyridin-2-ylamine (0.2 g) and naphthalene-2-sulfonyl chloride (0.366 g) as a white foam (0.392 g). MS (ESI$^-$): 325.2 ([M–H]$^-$).

Example 16

4'-Chloro-biphenyl-4-sulfonic acid (6-methyl-pyridin-2-yl)-amide

This material was obtained in analogy to example 1 from 6-methyl-pyridin-2-ylamine (0.22 g) and 4'-chloro-biphenyl-4-sulfonyl chloride (0.622 g) as a white solid (0.074 g). MS (ESI$^-$): 357.2 ([M–H]$^-$).

Example 17

4'-Fluoro-biphenyl-4-sulfonic acid (6-methyl-pyridin-2-yl)-amide

This material was obtained in analogy to example 1 from 6-methyl-pyridin-2-ylamine (0.4 g) and 4'-fluoro-biphenyl-4-sulfonyl chloride (1 g) as a white foam (0.779 g). MS (ESI$^-$): 341.1 ([M–H]$^-$).

Example 18

3,4-Dichloro-N-(6-propyl-pyridin-2-yl)-benzenesulfonamide

This material was obtained in analogy to example 1 from 6-propyl-pyridin-2-ylamine (0.15 g) and 3,4-dichloro-benzenesulfonyl chloride (0.27 g) as a white solid (0.199 g). MS (ESI$^-$): 342.9 ([M–H]$^-$).

Example 19

2,5-Difluoro-N-(6-propyl-pyridin-2-yl)-benzenesulfonamide

This material was obtained in analogy to example 1 from 6-propyl-pyridin-2-ylamine (0.1 g) and 2,5-difluoro-benzenesulfonyl chloride (0.17 g) as a white solid (0.114 g). MS (ESI$^-$): 311.0 ([M–H]$^-$).

Example 20

2,4-Dichloro-6-methyl-N-(6-propyl-pyridin-2-yl)-benzenesulfonamide

This material was obtained in analogy to example 1 from 6-propyl-pyridin-2-ylamine (0.1 g) and 2,4-dichloro-6-methyl-benzenesulfonyl chloride (0.191 g) as a light brown oil. (0.039 g). MS (ESI$^-$): 357.1 ([M–H]$^-$).

Example 21

5-Chloro-naphthalene-2-sulfonic acid (6-propyl-pyridin-2-yl)-amide

This material was obtained in analogy to example 1 from 6-propyl-pyridin-2-ylamine (0.1 g) and 5-chloro-naphthalene-2-sulfonyl chloride (0.191 g) as white solid. (0.047 g). MS (ESI$^-$): 359.0 ([M–H]$^-$).

Example 22

3,4-Dimethoxy-(6-propyl-pyridin-2-yl)-benzenesulfonamide

This material was obtained in analogy to example 1 from 6-propyl-pyridin-2-ylamine (0.1 g) and 3,4-dimethoxy-benzenesulfonyl chloride (0.174 g) as a colorless oil. (0.043 g). MS (ESI$^-$): 335.2 ([M–H]$^-$).

Example 23

4,5-Dichloro-2-fluoro-N-(6-propyl-pyridin-2-yl)-benzenesulfonamide

This material was obtained in analogy to example 1 from 6-propyl-pyridin-2-ylamine (0.1 g) and 4,5-dichloro-2-fluoro-benzenesulfonyl chloride (0.213 g) as a colorless oil. (0.176 g). MS (ESI): 363.1 (MH$^+$).

Example 24

2,4-Dichloro-5-methyl-N-(6-propyl-pyridin-2-yl)-benzenesulfonamide

This material was obtained in analogy to example 1 from 6-propyl-pyridin-2-ylamine (0.1 g) and 2,4-dichloro-5-methyl-benzenesulfonyl chloride (0.194 g) as a light yellow amorphous solid. (0.194 g). MS (ESI$^-$): 357.1 ([M–H]$^-$).

Example 25

Piperidine-1-sulfonic acid (6-propyl-pyridin-2-yl)-amide

A solution of 6-propyl-pyridin-2-ylamine (0.2 g) and piperidine-1-sulfonyl chloride (0.296 g, Bull. Soc. Chim. Fr.; 1936, 2143) in pyridine (7 mL) was heated to reflux for 15 h. After concentration of the reaction mixture in vacuo the residue was taken up in EtOAc, which was then washed with 1N aqueous HCl, saturated brine, dried over sodium sulphate and concentrated in vacuo. The residue was applied to a silica gel column with EtOAc/toluene (9:1 to 1:1) as eluent. Combination of the purified fractions and concentration in vacuo gave the desired piperidine-1-sulfonic acid (6-propyl-pyridin-2-yl)-amide (0.133 g) as a colorless amorphous solid. MS (ESI$^-$): 282.0 ([M–H]$^-$).

Example 26

3-Chloro-N-(6-isopropyl-pyridin-2-yl)-4-methyl-benzenesulfonamide

Step A]: 6-Isopropyl-pyridin-2-ylamine

2-Amino-6-bromopyridine (2 g) was dissolved in dioxane (50 mL), and at 0° C. under an argon athmosphere 1,3-bis (diphenylphosphino)propane nickel (II) chloride (0.627 g) was added followed by diisopropyl zinc (23.12 mL of a 1M solution in toluene, via syringe over 30 minutes). The mixture was allowed to reflux for 15 h, poured into 2-propanol, which was then concentrated in vacuo. The residue was partitioned between AcOEt and saturated aqueous NH$_4$Cl solution, the layers were separated and the organic layer dried over Na$_2$SO$_4$, filtered and evaporated. The residue was purified by flash chromatography (methylene chloride/methanol 95:5) to give 6-isopropyl-pyridin-2-ylamine as light brown oil (0.48 g). MS (EI): 136.1 (M$^+$).

Step B] 3-Chloro-N-(6-isopropyl-pyridin-2-yl)-4-methyl-benzenesulfonamide

This compound was obtained in analogy to example 1 from 6-isopropyl-pyridin-2-ylamine (0.1 g), and 3-chloro-4-methyl-benzenesulfonyl chloride (0.182 g) as a white solid (30 mg). MS (ESI$^-$): 324.1 ([M–H]$^-$).

Example 27

2,5-Difluoro-N-(6-isopropyl-pyridin-2-yl)-benzenesulfonamide

This material was obtained in analogy to example 1 from 6-isopropyl-pyridin-2-ylamine (0.1 g) and 2,5-difluoro-benzenesulfonyl chloride (0.172 g) as a colorless foam. (20 mg). MS (ESI$^-$): 311.1 ([M–H]$^-$).

Example 28

N-(6-Isopropyl-pyridin-2-yl)-4-(4-trifluoromethyl-phenoxy)-benzenesulfonamide

This material was obtained in analogy to example 1 from 6-isopropyl-pyridin-2-ylamine (0.1 g) and 4-(4-trifluoromethyl-phenoxy)-benzenesulfonyl chloride (0.272 g) as an amorphous colorless solid (31 mg). MS (ESI$^-$): 435.1 ([M–H]$^-$).

Example 29

2,4-Dichloro-N-(6-isopropyl-pyridin-2-yl)-5-methyl-benzenesulfonamide

This material was obtained in analogy to example 1 from 6-isopropyl-pyridin-2-ylamine (0.1 g) and 2,4-dichloro-5-methyl-benzenesulfonyl chloride (0.194 g) as an amorphous light yellow solid (35 mg). MS (ESI$^-$): 357.2 ([M−H]$^-$).

Example 30

N-(6-isopropyl-pyridin-2-yl)-4-methanesulfonyl-benzenesulfonamide

This material was obtained in analogy to example 1 from 6-isopropyl-pyridin-2-ylamine (0.1 g) and 4-methylsulfonyl-benzenesulfonyl chloride (0.206 g) as a white foam (46.8 mg). MS (ESI$^-$): 353.1 ([M−H]$^-$).

Example 31

N-(6-Isopropyl-pyridin-2-yl)-4-trifluoromethoxy-benzenesulfonamide

This material was obtained in analogy to example 1 from 6-isopropyl-pyridin-2-ylamine (0.1 g) and 4-(trifluoromethoxy)-benzenesulfonyl chloride (0.21 g) as an amorphous colorless solid (40 mg). MS (ESI$^-$): 359.0 ([M−H]$^-$).

Example 32

2-(2,2,2-Trifluoro-acetyl)-1,2,3,4-tetrahydro-isoquinoline-7-sulfonic acid (6-isopropyl-pyridin-2-yl)-amide This material was obtained in analogy to example 1 from 6-isopropyl-pyridin-2-ylamine (0.08 g) and 2-(2,2,2-trifluoro-acetyl)-1,2,3,4-tetrahydro-isoquinoline-7-sulfonyl chloride (0.212 g) as a white foam (35.2 mg). MS (ESI$^-$): 426.2 ([M−H]$^-$).

Example 33

N-(6-Isopropyl-pyridin-2-yl)-3-(4-trifluoromethyl-phenoxy)-benzenesulfonamide This material was obtained in analogy to example 1 from 6-isopropyl-pyridin-2-ylamine (0.08 g) and 3-(4-trifluoromethyl-phenoxy)-benzenesulfonyl chloride (0.218 g) as an amorphous light yellow solid (37 mg). MS (ESI$^-$): 435.1 ([M−H]$^-$).

Example 34

Naphthalene-2-sulfonic acid (6-isopropyl-pyridin-2-yl)-amide

This material was obtained in analogy to example 1 from 6-isopropyl-pyridin-2-ylamine (0.07 g) and naphthalene-2-sulfonyl chloride (0.128 g) as an amorphous light yellow solid (51 mg). MS (ESI$^-$): 325.2 ([M−H]$^-$).

Example 35

N-(6-Isopropyl-pyridin-2-yl)-3-trifluoromethyl-benzenesulfonamide

This material was obtained in analogy to example 1 from 6-isopropyl-pyridin-2-ylamine (0.06 g) and 3-(trifluoromethyl)-benzenesulfonyl chloride (0.119 g) as an amorphous colorless solid (38.3 mg). MS (ESI$^-$): 343.0 ([M−H]$^-$).

Example 36

N-[6-(2-Chloro-phenyl)-pyridin-2-yl]-5-fluoro-2-methyl-benzenesulfonamide

Step A]: 6-(2-Chloro-phenyl)-pyridin-2-ylamine

2-Amino-6-bromopyridine (1 g) and 2-chlorophenylboronic acid (1.039 g) were dissolved in toluene/ethanol (30 mL/3 mL) and at RT under an argon atmosphere treated with 2N aqueous sodium carbonate solution (6.13 mL). The mixture was stirred for 30 minutes at RT then treated with tetrakis (triphenylphosphine) palladium(0), 0.267 g, and heated to reflux for 24 h. The mixture was then cooled to RT and partitioned between AcOEt and water, the layers were separated and the organic layer dried over Na$_2$SO$_4$, filtered and evaporated. The residue was purified by flash chromatography (heptane/AcOEt 4:1) to give 6-(2-chloro-phenyl)-pyridin-2-ylamine as white solid (0.632 g). MS (EI): 204 (M$^+$).

Step B]: N-[6-(2-Chloro-phenyl)-pyridin-2-yl]-5-fluoro-2-methyl-benzenesulfonamide This compound was obtained in analogy to example 1 from 6-(2-chloro-phenyl)-pyridin-2-ylamine (0.1 g), and 5-fluoro-2-methyl-benzenesulfonyl chloride (0.112 g) as a white solid (89.3 mg). MS (ESI$^-$): 375.2 ([M−H]$^-$).

Example 37

3-Chloro-N-[6-(2-chloro-phenyl)-pyridin-2-yl]-2-methyl-benzenesulfonamide

This material was obtained in analogy to example 1 from 6-(2-chloro-phenyl)-pyridin-2-ylamine (0.1 g) and 3-(chloro)-2-methyl-benzenesulfonyl chloride (0.12 g) as an off-white foam (129 mg). MS (ESI$^-$): 390.9 ([M−H]$^-$).

Example 38

Biphenyl-4-sulfonic acid [6-(2-chloro-phenyl)-pyridin-2-yl]-amide

This material was obtained in analogy to example 1 from 6-(2-chloro-phenyl)-pyridin-2-ylamine (0.1 g) and biphenyl-4-sulfonyl chloride (0.136 g) as an white foam (126 mg). MS (ESI$^-$): 419.0 ([M−H]$^-$).

Example 39

3-Chloro-N-[6-(2,4-difluoro-phenyl)-pyridin-2-yl]-2-methyl-benzenesulfonamide Step A]: 6-(2,4-Difluoro-phenyl)-pyridin-2-ylamine This material was obtained in analogy to example 36 step A] from 2-Amino-6-bromopyridine (1 g) and 2,4-difluorophenylboronic acid (1.05 g) as a yellow solid (1.26 g). MS (ESI): 207.2 (MH$^+$).

Step B]: 3-Chloro-N-[6-(2,4-difluoro-phenyl)-pyridin-2-yl]-2-methyl-benzenesulfonamide This material was obtained in analogy to example 1 from 6-(2,4-difluoro-phenyl)-pyridin-2-ylamine (0.1 g) and 3-chloro-2-methyl-benzenesulfonyl chloride (0.12 g) as a white solid (0.132 g). MS (ESI$^-$): 392.9 ([M–H]$^-$).

Example 40

3-Chloro-N-[6-(3-fluoro-phenyl)-pyridin-2-yl]-2-methyl-benzenesulfonamide

Step A]: 6-(3-Fluoro-phenyl)-pyridin-2-ylamine

This material was obtained in analogy to example 36 step A] from 2-Amino-6-bromopyridine (0.75 g) and 3-fluorophenylboronic acid (0.7 g) as a yellow oil (0.81 g). MS (ESI): 189.3 (MH$^+$).

Step B]: 3-Chloro-N-[6-(3-fluoro-phenyl)-pyridin-2-yl]-2-methyl-benzenesulfonamide This material was obtained in analogy to example 1 from 6-(3-fluoro-phenyl)-pyridin-2-ylamine (0.1 g), and 3-chloro-2-methyl-benzenesulfonyl chloride (0.132 g) as a white solid (0.144 g). MS (ESI$^-$): 375.1 ([M–H]$^-$).

Example 41

3-Chloro-N-[6-(2,3-difluoro-phenyl)-pyridin-2-yl]-2-methyl-benzenesulfonamide Step A]: 6-(2,3-Difluoro-phenyl)-pyridin-2-ylamine This material was obtained in analogy to example 36 step A] from 2-Amino-6-bromopyridine (0.75 g) and 2,3-difluorophenylboronic acid (0.787 g) as a yellow solid (0.84 g). MS (ESI): 207.2 (MH$^+$).

Step B]: 3-Chloro-N-[6-(2,3-difluoro-phenyl)-pyridin-2-yl]-2-methyl-benzenesulfonamide This material was obtained in analogy to example 1 from 6-(2,3-difluoro-phenyl)-pyridin-2-ylamine (0.1 g), and 3-chloro-2-methyl-benzenesulfonyl chloride (0.12 g) as a white solid (0.115 g). MS (ESI$^-$): 392.9 ([M–H]$^-$).

Example 42

3-Chloro-N-[6-(2,5-dichloro-phenyl)-pyridin-2-yl]-2-methyl-benzenesulfonamide Step A]: 6-(2,5-Dichloro-phenyl)-pyridin-2-ylamine This material was obtained in analogy to example 36 step A] from 2-Amino-6-bromopyridine (0.75 g) and 2,5-dichlorophenylboronic acid (0.951 g) as an off-white solid (0.87 g). MS (ESI): 239.1 (MH$^+$).

Step B]: 3-Chloro-N-[6-(2,5-dichloro-phenyl)-pyridin-2-yl]-2-methyl-benzenesulfonamide This material was obtained in analogy to example 1 from 6-(2,5-dichloro-phenyl)-pyridin-2-ylamine (0.1 g), and 3-chloro-2-methyl-benzenesulfonyl chloride (0.104 g) as a white solid (0.094 g). MS (ESI$^-$): 425.0 ([M–H]$^-$).

Example 43

N-[6-(2,5-Dichloro-phenyl)-pyridin-2-yl]-5-fluoro-2-methyl-benzenesulfonamide This material was obtained in analogy to example 1 from 6-(2,5-dichloro-phenyl)-pyridin-2-ylamine (0.1 g) and 5-fluoro-2-methyl-benzenesulfonyl chloride (0.096 g) as an white solid (142 mg). MS (ESI$^-$): 409.0 ([M–H]$^-$).

Example 44

3-Chloro-N-[6-(3-chloro-phenyl)-pyridin-2-yl]-2-methyl-benzenesulfonamide

Step A]: 6-(3-Chloro-phenyl)-pyridin-2-ylamine

This material was obtained in analogy to example 36 step A] from 2-Amino-6-bromopyridine (0.75 g) and 3-chlorophenylboronic acid (0.75 g) as an off-white solid (0.87 g). MS (ESI): 205.1 (MH$^+$).

Step B]: 3-Chloro-N-[6-(3-chloro-phenyl)-pyridin-2-yl]-2-methyl-benzenesulfonamide This material was obtained in analogy to example 1 from 6-(3-chloro-phenyl)-pyridin-2-ylamine (0.1 g), and 3-chloro-2-methyl-benzenesulfonyl chloride (0.12 g) as a white solid (0.132 g). MS (ESI$^-$): 391.0 ([M–HI]$^-$).

Example 45

N-[6-(3-Chloro-phenyl)-pyridin-2-yl]-5-fluoro-2-methyl-benzenesulfonamide

This material was obtained in analogy to example 1 from 6-(3-chloro-phenyl)-pyridin-2-ylamine (0.1 g) and 5-fluoro-2-methyl-benzenesulfonyl chloride (0.112 g) as a white solid (172 mg). MS (ESI$^-$): 375.2 ([M–H]$^-$).

Example 46

3-Chloro-N-[6-(2-fluoro-phenyl)-pyridin-2-yl]-2-methyl-benzenesulfonamide

Step A]: 6-(2-Fluoro-phenyl)-pyridin-2-ylamine

This material was obtained in analogy to example 36 step A] from 2-Amino-6-bromopyridine (0.75 g) and 2-fluorophenylboronic acid (0.7 g) as an off-white solid (0.789 g). MS (ESI): 189.2 (MH$^+$).

Step B]: 3-Chloro-N-[6-(2-fluoro-phenyl)-pyridin-2-yl]-2-methyl-benzenesulfonamide This material was obtained in analogy to example 1 from 6-(2-fluoro-phenyl)-pyridin-2-ylamine (0.1 g), and 3-chloro-2-methyl-benzenesulfonyl chloride (0.132 g) as a light-yellow solid (0.135 g). MS (ESI$^-$): 375.2 ([M–H]$^-$).

Example 47

5-Fluoro-N-[6-(2-fluoro-phenyl)-pyridin-2-yl]-2-methyl-benzenesulfonamide

This material was obtained in analogy to example 1 from 6-(2-fluoro-phenyl)-pyridin-2-ylamine (0.1 g) and 5-fluoro-2-methyl-benzenesulfonyl chloride (0.12 g) as an off-white solid (0.19 g). MS (ESI$^-$): 359.0 ([M–H]$^-$).

Example 48

3-Chloro-2-methyl-N-[6-(2-trifluoromethyl-phenyl)-pyridin-2-yl]-benzenesulfonamide Step A]: 6-(2-Trifluoromethyl-phenyl)-pyridin-2-ylamine This material was obtained in analogy to example 36 step A] from 2-Amino-6-bromopyridine (0.7 g) and 2-(trifluoromethyl)phenylboronic acid (0.884 g) as a yellow solid (0.35 g). MS (ESI): 239.2 (MH$^+$).

Step B]: 3-Chloro-2-methyl-N-[6-(2-trifluoromethyl-phenyl)-pyridin-2-yl]-benzenesulfonamide This material was obtained in analogy to example 1 from 6-(2-trifluoromethyl-phenyl)-pyridin-2-ylamine (0.1 g), and 3-chloro-2-methyl-benzenesulfonyl chloride (0.086 g) as a white solid (0.08 g). MS (ESI$^-$): 425.1 ([M−H]$^-$).

Example 49

5-Fluoro-2-methyl-N-[6-(2-trifluoromethyl-phenyl)-pyridin-2-yl]-benzenesulfonamide This material was obtained in analogy to example 1 from 6-(2-trifluoromethyl-phenyl)-pyridin-2-ylamine (0.1 g) and 5-fluoro-2-methyl-benzenesulfonyl chloride (0.088 g) as an amorphous light brown solid (0.139 g). MS (ESI$^-$): 409.1 ([M−H]$^-$).

Example 50

N-[6-(2-Chloro-phenyl)-pyridin-2-yl]-2,5-difluoro-benzenesulfonamide

This material was obtained in analogy to example 1 from 6-(2-chloro-phenyl)-pyridin-2-ylamine (0.08 g) and 2,5-difluoro-benzenesulfonyl chloride (0.09 g) as a white foam (0.127 g). MS (ESI$^-$): 379.0 ([M−H]$^-$).

Example 51

N-[6-(2-Chloro-phenyl)-pyridin-2-yl]-2-trifluoromethyl-benzenesulfonamide

This material was obtained in analogy to example 1 from 6-(2-chloro-phenyl)-pyridin-2-ylamine (0.08 g) and 2-(trifluoromethyl)-benzenesulfonyl chloride (0.105 g) as an amorphous light yellow solid (0.167 g). MS (ESI$^-$): 411.0 ([M−H]$^-$).

Example 52

3-Chloro-N-[6-(2-methoxy-phenyl)-pyridin-2-yl]-2-methyl-benzenesulfonamide

Step A]: 6-(2-Methoxy-phenyl)-pyridin-2-ylamine

This material was obtained in analogy to example 36 step A] from 2-Amino-6-bromopyridine (0.75 g) and 2-methoxyphenylboronic acid (0.758 g) as a crystalline yellow solid (0.76 g). MS (ESI): 201.1 (MH$^+$).

Step B]: 3-Chloro-N-[6-(2-methoxy-phenyl)-pyridin-2-yl]-2-methyl-benzenesulfonamide This material was obtained in analogy to example 1 from 6-(2-methoxy-phenyl)-pyridin-2-ylamine (0.1 g), and 3-chloro-2-methyl-benzenesulfonyl chloride (0.102 g) as a colorless oil (0.091 g). MS (ESI$^-$): 387.1 ([M−H]$^-$).

Example 53

3-Chloro-N-[6-(4-fluoro-2-methyl-phenyl)-pyridin-2-yl]-2-methyl-benzenesulfonamide Step A]: 6-(4-Fluoro-2-methyl-phenyl)-pyridin-2-ylamine This material was obtained in analogy to example 36 step A] from 2-Amino-6-bromopyridine (0.75 g) and 4-fluoro-2-methyl-phenylboronic acid (0.767 g) as a yellow solid (0.828 g). MS (ESI): 203.1 (MH$^+$).

Step B]: 3-Chloro-N-[6-(4-fluoro-2-methyl-phenyl)-pyridin-2-yl]-2-methyl-benzenesulfonamide This material was obtained in analogy to example 1 from 6-(4-fluoro-2-methyl-phenyl)-pyridin-2-ylamine (0.1 g), and 3-chloro-2-methyl-benzenesulfonyl chloride (0.101 g) as a white solid (0.097 g). MS (ESI$^-$): 389.0 ([M−H]$^-$).

Example 54

5-Fluoro-N-[6-(4-fluoro-2-methyl-phenyl)-pyridin-2-yl]-2-methyl-benzenesulfonamide This material was obtained in analogy to example 1 from 6-(4-fluoro-2-methyl-phenyl)-pyridin-2-ylamine (0.1 g) and 5-fluoro-2-methyl-benzenesulfonyl chloride (0.103 g) as an colorless oil (0.101 g). MS (ESI$^-$): 373.1 ([M−H]$^-$).

Example 55

N-[2,3']Bipyridinyl-6-yl-3-chloro-2-methyl-benzenesulfonamide

Step A]: [2,3']Bipyridinyl-6-ylamine

This material was obtained via a Stille type coupling from 2-Amino-6-bromopyridine (0.75 g), 3-tributylstannanyl-pyridine (4.787 g), tetrakis(triphenylphosphine) palladium(0), 0.55 g, in DMF (5 mL) as solvent, by heating the mixture under argon at 100° C. for 16 h, subsequent work-up as described in example 36 step A], and isolation of [2,3']bipyridinyl-6-ylamine by flash chromatography (heptane/AcOEt 1:4 then methylene chloride/methanol 95:5) as an amorphous yellow solid (0.179 g). MS (ESI): 172.1 (MH$^+$).

Step B]: N-[2,3']Bipyridinyl-6-yl-3-chloro-2-methyl-benzenesulfonamide

This material was obtained in analogy to example 1 from [2,3']Bipyridinyl-6-ylamine (0.07 g), and 3-chloro-2-methyl-benzenesulfonyl chloride (0.101 g) as a yellow solid (5.5 mg). MS (ESI$^-$): 358.0 ([M−H]$^-$).

Example 56

2,5-Difluoro-N-[6-(4-fluoro-2-methyl-phenyl)-pyridin-2-yl]-benzenesulfonamide

This material was obtained in analogy to example 1 from 6-(4-fluoro-2-methyl-phenyl)-pyridin-2-ylamine (0.1 g) and 2,5-difluoro-benzenesilfonyl chloride (0.105 g) as an orange solid (0.052 g). MS (ESI$^-$): 377.2 ([M−H]$^-$).

Example 57

2,4-Dichloro-N-[6-(4-fluoro-2-methyl-phenyl)-pyridin-2-yl]-6-methyl-benzenesulfonamide This material was obtained in analogy to example 1 from 6-(4-fluoro-2-methyl-phenyl)-pyridin-2-ylamine (0.1 g) and 2,4-dichloro-6-methyl-benzenesulfonyl chloride (0.128 g) as a white solid (0.118 g). MS (ESI$^-$): 422.9 ([M–H]$^-$).

Example 58

3,4-Dichloro-N-[6-(4-fluoro-2-methyl-phenyl)-pyridin-2-yl]-benzenesulfonamide

This material was obtained in analogy to example 1 from 6-(4-fluoro-2-methyl-phenyl)-pyridin-2-ylamine (0.1 g) and 3,4-dichloro-benzenesulfonyl chloride (0.121 g) as a white solid (0.182 g). MS (ESI$^-$): 409.0 ([M–H]$^-$).

Example 59

3-Chloro-N-(6-methoxy-pyridin-2-yl)-2-methyl-benzenesulfonamide

This material was obtained in analogy to example 1 from 6-methoxy-pyridin-2-ylamine (0.25 g, Bernstein, J. Amer. Chem Soc., 69, 1947, 1147) and 3-chloro-2-methyl-benzenesulfonyl chloride (0.495 g) as a purple crystalline solid (0.38 g). MS (ESI$^-$): 311.0 ([M–H]$^-$).

Example 60

Biphenyl-4-sulfonic acid (6-methoxy-pyridin-2-yl)-amide

This material was obtained in analogy to example 1 from 6-methoxy-pyridin-2-ylamine (0.25 g) and biphenyl-4-sulfonyl chloride (0.5 g) as a white solid (0.41 g). MS (ESI$^-$): 339.0 ([M–H]$^-$).

Example 61

5-Fluoro-N-(6-methoxy-pyridin-2-yl)-2-methyl-benzenesulfonamide

This material was obtained in analogy to example 1 from 6-methoxy-pyridin-2-ylamine (0.25 g) and 5-fluoro-2-methyl-benzenesulfonyl chloride (0.45 g) as a red crystalline solid (0.38 g). MS (ESI$^-$): 295.1 ([M–H]$^-$).

Example 62

Naphthalene-2-sulfonic acid (6-methoxy-pyridin-2-yl)-amide

This material was obtained in analogy to example 1 from 6-methoxy-pyridin-2-ylamine (0.25 g) and naphthalene-2-sulfonyl chloride (0.49 g) as a light red waxy solid (0.5 g). MS (ESI$^-$): 312.9 ([M–H]$^-$).

Example 63

3-Chloro-N-(6-ethoxy-pyridin-2-yl)-2-methyl-benzenesulfonamide

This material was obtained in analogy to example 1 from 6-ethoxy-pyridin-2-ylamine (0.4 g, Bijlsma, Recl. Trav. Chim. Pays-Bas, 75, 1956, 1187) and 3-chloro-2-methyl-benzenesulfonyl chloride (0.7 g) as a light brown crystalline solid (0.6 g). MS (ESI$^-$): 325.1 ([M–H]$^-$).

Example 64

Biphenyl-4-sulfonic acid (6-ethoxy-pyridin-2-yl)-amide

This material was obtained in analogy to example 1 from 6-ethoxy-pyridin-2-ylamine (0.4 g) and biphenyl-4-sulfonyl chloride (0.74 g) as a light brown viscous oil (1 g). MS (ESI$^-$): 353.1 ([M–H]$^-$).

Example 65

Naphthalene-2-sulfonic acid (6-ethoxy-pyridin-2-yl)-amide

This material was obtained in analogy to example 1 from 6-ethoxy-pyridin-2-ylamine (0.4 g) and naphthalene-2-sulfonyl chloride (0.7 g) as a light brown crystalline solid (0.7 g). MS (ESI$^-$): 327.2 ([M–H]$^-$).

Example 66

3-Chloro-N-(6-ethylsulfanyl-pyridin-2-yl)-2-methyl-benzenesulfonamide

Step A]: 6-Ethylsulfanyl-pyridin-2-ylamine

2-Amino-6-bromopyridine (0.88 g) and sodium ethanethiolate (0.46 g) were dissolved in DMF (10 mL) stirred at RT for 20 h and subsequently at 60° C. for further 20 h to complete the reaction according to HPLC analysis. The mixture was concentrated in vacuo, partitioned between AcOEt and water, the layers were separated and the organic layer dried over Na$_2$SO$_4$, filtered and evaporated to give to give 6-ethylsulfanyl-pyridin-2-ylamine as brown oil (1.6 g) that was used directly in the next reaction step.

Step B]: N-[6-(2-Chloro-phenyl)-pyridin-2-yl]-5-fluoro-2-methyl-benzenesulfonamide This compound was obtained in analogy to example 1 from 6-ethylsulfanyl-pyridin-2-ylamine (0.44 g), and 3-chloro-2-methyl-benzenesulfonyl chloride (0.7 g) as a light brown viscous oil (0.7 g). MS (ESI$^-$): 341.1 ([M–H]$^-$).

Example 67

Biphenyl-4-sulfonic acid (6-ethylsulfanyl-pyridin-2-yl)-amide

This material was obtained in analogy to example 1 from 6-ethylsulfanyl-pyridin-2-ylamine (0.44 g) and biphenyl-4-sulfonyl chloride (0.78 g) as a light brown viscous oil (0.53 g). MS (ESI$^-$): 369.0 ([M–H]$^-$).

Example 68

Naphthalene-2-sulfonic acid (6-ethylsulfanyl-pyridin-2-yl)-amide

This material was obtained in analogy to example 1 from 6-ethylsulfanyl-pyridin-2-ylamine (0.44 g) and naphthalene-2-sulfonyl chloride (0.7 g) as a light brown viscous oil (1 g). MS (ESI$^-$): 342.9 ([M–H]$^-$).

Example 69

Naphthalene-2-sulfonic acid (6-ethanesulfonyl-pyridin-2-yl)-amide

A solution of naphthalene-2-sulfonic acid (6-ethylsulfanyl-pyridin-2-yl)-amide (0.15 g, product of example 68) in $CH_2Cl_2$ (20 mL) was treated dropwise at RT with 3-chloroperoxybenzoic acid (0.15 g) in 5 mL $CH_2Cl_2$) and stirred for 2 h at RT. The reaction mixture was washed with diluted aqueous $Na_2CO_3$ and water, then dried over $Na_2SO_4$, filtered and evaporated. The residue was purified by flash chromatography (toluene/EtOAc 1:1) to give naphthalene-2-sulfonic acid (6-ethanesulfonyl-pyridin-2-yl)-amide as a white foam (60 mg). MS (ESI$^-$): 375.2 ([M–H]$^-$).

Example 70

3-Chloro-2-methyl-N-[6-(2-oxo-pentyl)-pyridin-2-yl]-benzenesulfonamide

Step A]: 1-($^6$-Amino-pyridin-2-yl)-pentan-2-one 1,1,1,3,3,3-Hexamethyl-2-(6-methyl-pyridin-2-yl)-disilazane (1 g, Engelhardt, J. Chem. Soc. Chem. Commun.,1990, 89) under an argon atmosphere in THF (20 mL) was cooled to −20° C. and treated dropwise at −20° C. with 4.95 mL of a 1.6 M solution of N-butyllithium in hexane over a period of 1 h. The solution was stirred 1 h at −20° C., N-butyronitrile (0.301 g) was added and the mixture was allowed to warm to RT. It was then treated with 1.25 N HCL in methanol (6.34 ml) and stirred for 30 minutes at RT. The mixture was poured into water (pH 1) and extracted with AcOEt that was discarded, the water layer was brought to pH 8 with solid $KHCO_3$ and extracted twice with AcOEt. The layers were separated, the organic layer dried over $Na_2SO_4$, filtered and evaporated to give 1-(6-Amino-pyridin-2-yl)-pentan-2-one as viscous yellow oil (0.34 g) that was used without further purification in the next step. MS (EI): 179.2 (M$^+$).

Step B]: 3-Chloro-2-methyl-N-[6-(2-oxo-pentyl)-pyridin-2-yl]-benzenesulfonamide 1-(6-Amino-pyridin-2-yl)-pentan-2-one (0.15 g) in $CH_2Cl_2$ (5 mL) was treated at RT with 4-dimethylaminopyridine (0.103 g), 3-chloro-2-methyl-benzenesulfonyl chloride (0.208 g) and stirred at RT for 16 h. The mixture was partitioned between cold diluted aqueous HCl and AcOEt, the layers were separated, and the organic layer twice extracted with AcOEt. The combined organic layers were dried over $Na_2SO_4$, filtered and evaporated. From the residue was isolated by flash chromatography (heptane/EtOAc 1:1) the vinyl sulfonate 3-chloro-2-methyl-benzenesulfonic acid 1-[1-[6-(3-chloro-2-methyl-benzenesulfonylamino)-pyridin-2-yl]-meth-(Z)-ylidene]-butyl ester (23 mg) as an amorphous off-white solid (27 mg). MS (ESI$^-$): 552.8 ([M–H]$^-$).

This material was hydrolysed to the desired product as following: 20 mg of above material in methanol (3 mL) was treated with 0.035 mL 2N NaOH in methanol and heated to reflux for 1.5 h. The mixture was partitioned between water and AcOEt and the aqueous layer adjusted to pH 7. The layers were separated, the organic layer dried over $Na_2SO_4$, filtered and evaporated to give 3-chloro-2-methyl-N-[6-(2-oxo-pentyl)-pyridin-2-yl]-benzenesulfonamide (12 mg) as an amorphous light yellow solid. MS (ESI$^-$): 365.0 ([M–H]$^-$).

Example 71

2-[6-(Biphenyl-4-sulfonylamino)-pyridin-2-yl]-N,N-diethyl-acetamide

Step A]: [6-(Biphenyl-4-sulfonylamino)-pyridin-2-yl]-acetic acid

Biphenyl-4-sulfonic acid (6-methyl-pyridin-2-yl)-amide (0.5 g, product of example 5) under an argon atmosphere in THF (5 mL) was cooled to −20° C. and treated dropwise at −20° C. with 1.54 mL of a 2 M solution of lithium diisopropylamide in THF/heptane/ethylbenzene (Fluka). The solution was stirred 1 h at −20° C., cooled to −70° C. and then treated with an access of dry ice. The mixture was allowed to warm to RT (1 h), partitioned between diluted aqueous HCl and AcOEt. The layers were separated, the aqueous layer extracted twice with AcOEt, the combined organic layers dried over $Na_2SO_4$, filtered and evaporated to give [6-(biphenyl-4-sulfonylamino)-pyridin-2-yl]-acetic acid as light yellow gum (0.779 g) that was used without further purification in the next step.

Step B]: 2-[6-(Biphenyl-4-sulfonylamino)-pyridin-2-yl]-N,N-diethyl-acetamide

[6-(Biphenyl-4-sulfonylamino)-pyridin-2-yl]-acetic acid (0.35 g) in acetonitrile (5 mL) was treated at RT with N,N-ethyldiisopropylamine (0.16 mL), benzotriazol-1-yloxytris (dimethylamino)phosphonium hexafluorophosphate (BOP, 0.252 g) then diethylamine (0.05 mL), and the mixture was stirred at RT for 16 h. It was then partitioned between cold diluted aqueous HCl and AcOEt, the layers were separated, the organic layer dried over $Na_2SO_4$, filtered and evaporated. The residue was purified by flash chromatography (heptane/EtOAc 1:1) to give 2-[6-(biphenyl-4-sulfonylamino)-pyridin-2-yl]-N,N-diethyl-acetamide as a yellow solid (0.168 g). MS (ESI$^-$): 422.2 ([M–H]$^-$).

Example 72

Biphenyl-4-sulfonic acid [6-(2-morpholin-4-yl-2-oxo-ethyl)-pyridin-2-yl]-amide This material was obtained in analogy to example 71 Step B] from [6-(biphenyl-4-sulfonylamino)-pyridin-2-yl]-acetic acid (0.16 g), BOP (0.23 g), N,N-ethyldiisopropylamine (0.15 mL) and morpholine (0.042 g) as a light brown solid (67 mg). MS (ESI$^-$): 436.2 ([M–H]$^-$).

Example 73

[6-(3-Chloro-2-methyl-benzenesulfonylamino)-pyridin-2-yl]-acetic acid methyl ester Step A]: (6-Amino-pyridin-2-yl)-acetic acid methyl ester 1,1,1,3,3,3-Hexamethyl-2-(6-methyl-pyridin-2-yl)-disilazane (1.7 g) under an argon atmosphere in THF (20 mL) was cooled to −20° C. and treated dropwise at −20° C. with 6.73 mL of a 2 M solution of lithium diisopropylamide in THF/heptane/ethylbenzene (Fluka). The solution was stirred 1 h at −20° C., cooled to −70° C. and then treated with an access of dry ice. The mixture was allowed to warm to 0° C. and then quenched with trifluoro-acetic acid(0.57 ml) and concentrated in vacuo. The residue was taken up in MeOH and added dropwise to a solution of thionyl chloride (9.77 mL) in MeOH (30 ml) at 0° C. The reaction mixture was then heated to reflux for 24 h, cooled to RT and concentrated in vacuo. The residue was partitioned between aqueous diluted $NaHCO_3$ and AcOEt, the layers were separated, the organic layer dried over $Na_2SO_4$, filtered, evaporated and the residue purified by flash chromatography (heptane/AcOEt 1:1) to give (6-amino-pyridin-2-yl)-acetic acid methyl ester as a crystalline off-white solid (0.429 g). MS (EI): 166.0 ($M^+$).

Step B]: [6-(3-Chloro-2-methyl-benzenesulfonylamino)-pyridin-2-yl]-acetic acid methyl ester This material was obtained in analogy to example 1 from (6-amino-pyridin-2-yl)-acetic acid methyl ester (0.15 g) and 3-chloro-2-methyl-benzenesulfonyl chloride (0.223 g) as a light brown gum (14 mg). MS ($ESI^-$): 353.1 ($[M-H]^-$).

Example 74

[6-(5-Fluoro-2-methyl-benzenesulfonylamino)-pyridin-2-yl]-acetic acid methyl ester This material was obtained in analogy to example 1 from (6-amino-pyridin-2-yl)-acetic acid methyl ester (0.15 g) and 5-fluoro-2-methyl-benzeflesulfonyl chloride (0.207 g) as a light brown gum (20 mg). MS ($ESI^-$): 337.0 ($[M-H]^-$).

Example 75

N,N-Diethyl-2-[6-(4'-fluoro-biphenyl-4-sulfonylamino)-pyridin-2-yl]-acetamide

Step A]: [6-(4'-Fluoro-biphenyl-4-sulfonylamino)-pyridin-2-yl]-acetic acid

This material was obtained in analogy to example 71 step A] from 4'-fluoro-biphenyl-4-sulfonic acid (6-methyl-pyridin-2-yl)-amide (0.5 g, product of example 17), 1.46 mL of a 2 M lithium diisopropylamide solution in THF/heptane/ethylbenzene, and dry ice to give [6-(4'-fluoro-biphenyl-4-sulfonylamino)-pyridin-2-yl]-acetic acid as a gum (0.69 g) that was used without further purification in the next step.

Step B]: N,N-Diethyl-2-[6-(4'-fluoro-biphenyl-4-sulfonylamino)-pyridin-2-yl]-acetamide This material was obtained in analogy to example 71 step B] from [6-(4'-fluoro-biphenyl-4-sulfonylamino)-pyridin-2-yl]-acetic acid (0.2 g), BOP (0.137 g), N,N-ethyldiisopropylamine (0.09 mL), and diethylamine (0.03 mL) as an off-white foam (0.107 g). MS ($ESI^-$): 440.2 ($[M-H]^-$).

Example 76

4'-Fluoro-biphenyl-4-sulfonic acid [6-(2-morpholin-4-yl-2-oxo-ethyl)-pyridin-2-yl]-amide This material was obtained in analogy to example 71 step B] from [6-(4'-fluoro-biphenyl-4-sulfonylamino)-pyridin-2-yl]-acetic acid (0.2 g), BOP (0.137 g), N,N-ethyldiisopropylamine (0.067 mL), and morpholine (0.02 mL) as an off-white solid (0.114 g). MS ($ESI^-$): 454.2 ($[M-H]^-$).

Example 77

2-[6-(4'-Fluoro-biphenyl-4-sulfonylamino)-pyridin-2-yl]-N-(2-methoxy-ethyl)-acetamide This material was obtained in analogy to example 71 step B] from [6-(4'-fluoro-biphenyl-4-sulfonylamino)-pyridin-2-yl]-acetic acid (0.1 g), BOP (0.069 g), N,N-ethyldiisopropylamine (0.04 mL), and 2-methoxyethylamine (0.01 mL) as an amorphous light brown solid (0.0475 g). MS ($ESI^-$): 444.2 ($[M-H]^-$).

Example 78

2-[6-(3-Chloro-2-methyl-benzenesulfonylamino)-pyridin-2-yl]-N,N-diethyl-acetamide Step A]: (6-tert-Butoxycarbonylamino-pyridin-2-yl)-acetic acid (6-Methyl-pyridin-2-yl)-carbamic acid tert-butyl ester (1.04 g, Pitts, J. Med. Chem., 43, 2000, 27) under an argon atmosphere in THF (40 mL) was cooled to −20° C. and treated dropwise at −20° C. with 5.5 mL of a 2 M solution of lithium diisopropylamide in THF/heptane/ethylbenzene (Fluka). The solution was stirred 1 h at −20° C., cooled to −70° C. and then treated with an access of dry ice. The mixture was allowed to warm to 10° C. and partitioned between aqueous 1N HCl and AcOEt, the layers were separated, the organic layer dried over $Na_2SO_4$, filtered, evaporated and the residue was purified by flash chromatography (MeOH/$CH_2Cl_2$ 0-15%). The obtained material was triturated with ether, the crystalline solid obtained was filtered off by suction and dried in vacuo to give (6-tert-butoxycarbonylamino-pyridin-2-yl)-acetic acid as an off-white solid (0.3 g). MS ($ESI^-$): 251.1 ($[M-H]^-$).

Step B]: (6-Diethylcarbamoylmethyl-pyridin-2-yl)-carbamic acid tert-butyl ester

This material was obtained in analogy to example 71 step B] from (6-tert-butoxycarbonylamino-pyridin-2-yl)-acetic acid (0.298 g), BOP (0.575 g), N,N-ethyldiisopropylamine (0.42 mL), and diethylamine (0.14 mL) as a yellow gum (0.202 g). MS (ESI): 308.3 ($MH^+$).

Step C]: 2-(6-Amino-pyridin-2-yl)-N,N-diethyl-acetamide (6-Diethylcarbamoylmethyl-pyridin-2-yl)-carbamic acid tert-butyl ester (0.2 g) in $CH_2Cl_2$ (10 mL) was treated at RT with trifluoro-acetic acid (0.5 mL) and the solution was stirred for 1.5 h until the reaction was complete according to the analysis. The mixture was allowed to warm to 10° C. and partitioned between aqueous diluted $KHCO_3$ and AcOEt, the layers were separated, the organic layer dried over $Na_2SO_4$, filtered, evaporated to give 2-(6-amino-pyridin-2-yl)-N,N-diethyl-acetamide (148 mg) as a light yellow solid that was directly used in the next step.

Step D]: 2-[6-(3-Chloro-2-methyl-benzenesulfonylamino)-pyridin-2-yl]-N,N-diethyl-acetamide This material was obtained in analogy to example 1 from 2-(6-amino-pyridin-2-yl)-N,N-diethyl-acetamide (0.07 g) and 3-chloro-2-methyl-benzenesulfonyl chloride (0.084 g) as a light yellow foam (41 mg). MS ($ESI^-$): 394.0 ($[M-H]^-$).

Example 79

2-[6-(3,4-Dichloro-benzenesulfonylamino)-pyridin-2-yl]-N,N-diethyl-acetamide

This material was obtained in analogy to example 1 from 2-(6-amino-pyridin-2-yl)-N,N-diethyl-acetamide (0.07 g, product of example 78 step C]) and 3,4-dichloro-benzenesulfonyl chloride (0.091 g) as an amorphous yellow solid (41 mg). MS (ESI$^-$): 414.1 ([M–H]$^-$).

Example 80

2-[6-(3-Chloro-2-methyl-benzenesulfonylamino)-3-methyl-pyridin-2-yl]-N,N-diethyl-acetamide Step A]: (3-Bromo-6-tert-butoxycarbonylamino-pyridin-2-yl)-acetic acid This material was obtained in analogy to example 78 step A] from (5-bromo-6-methyl-pyridin-2-yl)-carbamic acid tert-butyl ester, 4.3 g—prepared from 6-methyl-pyridin-2-yl)-carbamic acid tert-butyl ester, example 78 step A] via bromination with NBS/AIBN, using a procedure described by Manabu, Chem. Lett. 1995, 614-2M lithium diisopropylamide solution (16.5 mL) and an access of dry ice as a crystalline solid (2.6 g) that was used directly without further purification in the next reaction step.

Step B]: (5-Bromo-6-diethylcarbamoylmethyl-pyridin-2-yl)-carbamic acid tert-butyl ester This material was obtained in analogy to example 78 step B] from (3-bromo-6-tert-butoxycarbonylamino-pyridin-2-yl)-acetic acid (0.662 g), BOP (0.974 g), N,N-ethyldiisopropylamine (0.78 mL), and diethylamine (0.23 mL) as a light brown solid (0.67 g). MS (ESI): 386.3. (MH$^+$).

Step C]: (6-Diethylcarbamoylmethyl-5-methyl-pyridin-2-yl)-carbamic acid tert-butyl ester (5-Bromo-6-diethylcarbamoylmethyl-pyridin-2-yl)-carbamic acid tert-butyl ester (0.116 g in dioxane (5 mL) was treated successively at RT with potassium carbonate (0.124 g), tetrakis(triphenylphosphine) palladium(0), 35 mg, and trimethylboroxine (38 mg) and then heated to reflux for 22 h. The mixture was cooled to RT, filtered and the filter cake washed with AcOEt. The filtrate was concentrated in vacuo, the residue purified by flash chromatography (heptane/AcOEt 1:1 to 1:4) to give (6-diethylcarbamoylmethyl-5-methyl-pyridin-2-yl)-carbamic acid tert-butyl ester (37 mg) as a colorless gum. MS (ESI): 322.4 (MH$^+$).

Step D]: 2-(6-Amino-3-methyl-pyridin-2-yl)-N,N-diethyl-acetamide

This material was obtained in analogy to example 78 step C] from (6-diethylcarbamoylmethyl-5-methyl-pyridin-2-yl)-carbamic acid tert-butyl ester (0.193 and trifluoro-acetic acid (0.69 mL) in CH$_2$Cl$_2$ (8 mL) as a yellow gum (0.148 g ). MS (ESI): 222.2 (MH$^+$).

Step E]: 2-[6-(3-Chloro-2-methyl-benzenesulfonylamino)-3-methyl-pyridin-2-yl]-N,N-diethyl-acetamide This material was obtained in analogy to example 1 from 2-(6-amino-3-methyl-pyridin-2-yl)-N,N-diethyl-acetamide (0.066 g) and 3-chloro-2-methyl-benzenesulfonyl chloride (0.074 g) as an off-white foam (33 mg). MS (ESI$^-$): 408.1 ([M–H]$^-$).

Example 81

2-[6-(3,4-Dichloro-benzenesulfonylamino)-3-methyl-pyridin-2-yl]-N,N-diethyl-acetamide This material was obtained in analogy to example 1 from 2-(6-amino-3-methyl-pyridin-2-yl)-N,N-diethyl-acetamide (0.066 g) and 3,4-dichloro-benzenesulfonyl chloride (0.081 g) as an off-white foam (55 mg). MS (ESI$^-$): 428.1 ([M–H]$^-$).

Example 82

3-Chloro-N-(6-hydroxymethyl-pyridin-2-yl)-2-methyl-benzenesulfonamide

This material was obtained in analogy to example 1 from (6-amino-pyridin-2-yl)-methanol (0.095 g, Asensio, Tetrahedron, 49, 1993, 703) and 3-chloro-2-methyl-benzenesulfonyl chloride (0.172 g) as an white solid (0.115 g). MS (ESI$^-$): 311.0 ([M–H]$^-$).

Example 83

3-Chloro-N-(6-methoxymethyl-pyridin-2-yl)-2-methyl-benzenesulfonamide

This material was obtained in analogy to example 1 from 6-methoxymethyl-pyridin-2-ylamine (0.096 g, Shawcross, J. Heterocycl. Chem., 30, 1993, 563) and 3-chloro-2-methyl-benzenesulfonyl chloride (0.172 g) as an off-white gum (0.158 g). MS (ESI$^-$): 325.1 ([M–H]$^-$)

Example 84

2,5-Difluoro-N-(6-methoxymethyl-pyridin-2-yl)-benzenesulfonamide

This material was obtained in analogy to example 1 from 6-methoxymethyl-pyridin-2-ylamine (0.096 g) and 2,4-difluoro-benzenesulfonyl chloride (0.162 g) as an off-white gum (0.156 g). MS (ESI$^-$): 312.9 ([M–H]$^-$)

Example 85

3-Chloro-N-(6-methoxymethyl-pyridin-2-yl)-4-methyl-benzenesulfonamide

This material was obtained in analogy to example 1 from 6-methoxymethyl-pyridin-2-ylamine (0.096 g) and 3-chloro-4-methyl-benzenesulfonyl chloride (0.172 g) as an off-white gum (0.169 g). MS (ESI$^-$): 325.1 ([M–H]$^-$)

Example 86

N-(6-Cyclopropylmethoxymethyl-pyridin-2-yl)-2,5-difluoro-benzenesulfonamide

Step A]: N-(6-Cyclopropylmethoxymethyl-pyridin-2-yl)-2,2-dimethyl-propionamide

N-(6-Hydroxymethyl-pyridin-2-yl)-2,2-dimethyl-propionamide (1.04 g, Papadopoulou,; J. Heterocycl. Chem., 32, 1995, 675) in DMF (25 mL) was treated with sodium hydride (0.64 g, 60% suspension in oil), the mixture was then stirred for 1 h at RT, bromomethyl cyclopropane (0.688 g) was added dropwise and stirring was continued for further 1.75 h. The reaction mixture was partitioned between 2 M aqueous KHCO$_3$ and AcOEt, the layers were separated, the aqueous layer extracted twice with AcOEt. The combined organic layers were washed with saturated aqueous NaCl and water, dried over Na$_2$SO$_4$, filtered and evaporated. The residue was purified by flash chromatography (heptane/AcOEt 100% to 50%) to N-(6-cyclopropylmethoxymethyl-pyridin-2-yl)-2,2-dimethyl-propionamide (0.884 g) as a yellow oil. MS (ESI): 263.2 (MH$^+$).

Step B]: 6-Cyclopropylmethoxymethyl-pyridin-2-ylamine

N-(6-cyclopropylmethoxymethyl-pyridin-2-yl)-2,2-dimethyl-propionamide (0.884 g) in ethanol (50 mL) was treated at RT with 3M aqueous NaOH (5.62 mL) and then heated at 100° C. for 20 h. The mixture was cooled to RT, partitioned between water and AcOEt. The layers were separated, the organic layer dried over magnesium sulphate, filtered and evaporated in vacuo to give 6-cyclopropylmethoxymethyl-pyridin-2-ylamine (0.566 g) as a light brown liquid. MS (ESI): 179.1 (MH$^+$).

Step C]: N-(6-Cyclopropylmethoxymethyl-pyridin-2-yl)-2,5-difluoro-benzenesulfonamide This material was obtained in analogy to example 1 from 6-cyclopropylmethoxymethyl-pyridin-2-ylamine (0.089g) and 2,5-difluoro-benzenesulfonyl chloride (0.122 g) as an light brown gum (0.175 g). MS (ESI$^-$): 353.1 ([M−H]$^-$)

Example 87

5-Fluoro-N-(6-methoxymethyl-pyridin-2-yl)-2-methyl-benzenesulfonamide

This material was obtained in analogy to example 1 from 6-methoxymethyl-pyridin-2-ylamine (0.096 g) and 5-fluoro-2-methyl-benzenesulfonyl chloride (0.159 g) as an light yellow gum (0.16 g). MS (ESI$^-$): 309.1 ([M−H]$^-$)

Example 88

2,5-Difluoro-N-(6-hydroxymethyl-pyridin-2-yl)-benzenesulfonamide

This material was obtained in analogy to example 1 from (6-amino-pyridin-2-yl)-methanol (0.1 g) and 2,5-difluoro-benzenesulfonyl chloride (0.17 g) as an light brown amorphous solid MS (ESI$^-$): 299.1 ([M−H]$^-$)

Example 89

Acetic acid 6-(2,5-difluoro-benzenesulfonylamino)-pyridin-2-ylmethyl ester

This material was obtained as a second product in the preparation of example 88 (during work-up with AcOEt in the presence of acid) as a red amorphous solid (17 mg). MS (ESI$^-$): 341.0 ([M−H]$^-$)

Example 90

Naphthalene-2-sulfonic acid (6-hydroxymethyl-pyridin-2-yl)-amide

This material was obtained in analogy to example 1 from (6-amino-pyridin-2-yl)-methanol (0.042 g) and naphthalene-2-sulfonyl chloride (0.084 g) as an off-white foam (32 mg g). MS (ESI$^-$): 312.9 ([M−H]$^-$)

Example 91

3-Chloro-N-(6-cyclopropylmethoxymethyl-pyridin-2-yl)-4-methyl-benzenesulfonamide This material was obtained in analogy to example 1 from 6-cyclopropylmethoxymethyl-pyridin-2-ylamine (0.089 g) and 3-chloro-4-methyl-benzenesulfonyl chloride (0.124 g) as a light-yellow gum (0.136 g). MS (ESI$^-$): 364.9 ([M−H]$^-$)

Example 92

N-(6-Cyclopropylmethoxymethyl-pyridin-2-yl)-5-fluoro-2-methyl-benzenesulfonamide This material was obtained in analogy to example 1 from 6-cyclopropylmethoxymethyl-pyridin-2-ylamine (0.089 g) and-5-fluoro-2-methyl-benzenesulfonyl chloride (0.15 g) as an off-white gum (0.14 g). MS (ESI$^-$): 349.2 ([M−H]$^-$)

Example 93

3-Chloro-N-[6-(4-fluoro-benzyloxymethyl)-pyridin-2-yl]-4-methyl-benzenesulfonamide Step A]: N-[6-(4-Fluoro-benzyloxymethyl)-pyridin-2-yl]-2,2-dimethyl-propionamide This material was prepared in analogy to example 86 step A] from N-(6-hydroxymethyl-pyridin-2-yl)-2,2-dimethyl-(0.625 g) and 4-fluorobenzyl bromide as a yellow oil (0.83 g). MS (ESI): 317.1 (MH$^+$).

Step B]: 6-(4-Fluoro-benzyloxymethyl)-pyridin-2-ylamine

This material was prepared in analogy to example 86 step B] from N-[6-(4-Fluoro-benzyloxymethyl)-pyridin-2-yl]-2,2-dimethyl-propionamide (0.825 g) and 3M aqueous NaOH (4.35 mL) as a yellow oil (0.596 g). MS (ESI): 233.1 (MH$^+$).

Step C]: 3-Chloro-N-[6-(4-fluoro-benzyloxymethyl)-pyridin-2-yl]-4-methyl-benzenesulfonamide This material was prepared in analogy to example 1 from 6-(4-fluoro-benzyloxymethyl)-pyridin-2-ylamine (0.058 g) and 3-chloro-4-methyl-benzenesulfonyl chloride (0.062 g) as a light yellow gum (0.09 g). MS (ESI$^-$): 419.0. ([M−H]$^-$)

Example 94

3-Chloro-N-[6-(4-fluoro-benzyloxymethyl)-pyridin-2-yl]-2-methyl-benzenesulfonamide This material was prepared in analogy to example 1 from 6-(4-fluoro-benzyloxymethyl)-pyridin-2-ylamine (0.058 g) and 3-chloro-2-methyl-benzenesulfonyl chloride (0.062 g) as a light yellow gum (0.087 g). MS (ESI$^-$): 419.0. ([M−H]$^-$)

Example 95

2,5-Difluoro-N-[6-(4-fluoro-benzyloxymethyl)-pyridin-2-yl]-benzenesulfonamide

This material was prepared in analogy to example 1 from 6-(4-fluoro-benzyloxymethyl)-pyridin-2-ylamine (0.058 g) and 2,5-difluoro-benzenesulfonyl chloride (0.058 g) as a light yellow gum (0.075 g). MS (ESI$^-$): 407.2 ([M−H]$^-$)

Example 96

5-Fluoro-N-[6-(4-fluoro-benzyloxymethyl)-pyridin-2-yl]-2-methyl-benzenesulfonamide This material was prepared in analogy to example 1 from 6-(4-fluoro-benzyloxymethyl)-pyridin-2-ylamine (0.058 g) and 5-fluoro-2-methyl-benzenesulfonyl chloride (0.057 g) as a light yellow gum (0.0476 g). MS (ESI$^-$): 403.2 ([M−H]$^-$)

Example 97

Piperidine-1-sulfonic acid (6-methoxymethyl-pyridin-2-yl)-amide

This material was obtained in analogy to example 1 from 6-methoxymethyl-pyridin-2-ylamine (0.096 g) and piperidine-1-sulfonyl chloride (0.153 g) as a light yellow gum (0.024 g). MS (ESI$^-$): 284.0 ([M−H]$^-$)

Example 98

Piperidine-1-sulfonic acid (6-cyclopropylmethoxymethyl-pyridin-2-yl)-amide

This material was obtained in analogy to example 1 from 6-cyclopropylmethoxymethyl-pyridin-2-ylamine (0.089 g) and piperidine-1-sulfonyl chloride (0.11 g) as a light yellow gum (0.054 g). MS (ESI$^-$): 324.2 ([M−H]$^-$)

Example 99

3-Chloro-4-methyl-N-[6-(4-trifluoromethyl-phenoxymethyl)-pyridin-2-yl]-benzenesulfonamide Step A]: 2,2-Dimethyl-N-[6-(4-trifluoromethyl-phenoxymethyl)-pyridin-2-yl]-propionamide N-(6-Hydroxymethyl-pyridin-2-yl)-2,2-dimethyl-propionamide (0.625 g), triphenylphophine (0.786 g) and 4-trifluoromethyl-phenol (0.486 g) in toluene was treated at RT under an argon atmosphere with diisopropyl azodicarboxylate (0.67 g). The mixture was stirred for 2 h, partitioned between ice water and AcOEt, the layers were separated, the aqueous layer twice extracted with AcOEt. The combined organic layers were washed with water and saturated aqueous NaCl, dried over MgSO$_4$, filtered and evaporated. The residue was purified by flash chromatography (heptane/AcOEt 100 to 85%) to give 2,2-dimethyl-N-[6-(4-trifluoromethyl-phenoxymethyl)-pyridin-2-yl]-propionamide (0.98 g) as a yellow oil. MS (ESI): 353.2 (MH$^+$).

Step B]: 6-(4-Trifluoromethyl-phenoxymethyl)-pyridin-2-ylamine

This material was prepared in analogy to example 86 step B] from 2,2-Dimethyl-N-[6-(4-trifluoromethyl-phenoxymethyl)-pyridin-2-yl]-propionamide (0.99 g) and 3M aqueous NaOH (4.68 mL) as an off-white crystalline solid (0.647 g). MS (ESI): 269.3 (MH$^+$).

Step C]: 3-Chloro-4-methyl-N-[6-(4-trifluoromethyl-phenoxymethyl)-pyridin-2-yl]-benzenesulfonamide This material was prepared in analogy to example 1 from 6-(4-trifluoromethyl-phenoxymethyl)-pyridin-2-ylamine (0.08 g) and 3-chloro-4-methyl-benzenesulfonyl chloride (0.074 g) as an off-white solid (0.105 g). MS (ESI$^-$): 455.2 ([M−H]$^-$).

Example 100

3-Chloro-2-methyl-N-[6-(4-trifluoromethyl-phenoxymethyl)-pyridin-2-yl]-benzenesulfonamide This material was prepared in analogy to example 1 from 6-(4-trifluoromethyl-phenoxymethyl)-pyridin-2-ylamine (0.08 g) and 3-chloro-2-methyl-benzenesulfonyl chloride (0.074 g) as an off-white solid (0.113 g). MS (ESI$^-$): 455.2 ([M−H]$^-$).

Example 101

2,5-Difluoro-N-[6-(4-trifluoromethyl-phenoxymethyl)-pyridin-2-yl]-benzenesulfonamide This material was prepared in analogy to example 1 from 6-(4-trifluoromethyl-phenoxymethyl)-pyridin-2-ylamine (0.08 g) and 2,5-difluoro-benzenesulfonyl chloride (0.07 g) as a light yellow solid (0.086 g). MS (ESI$^-$): 443.0 ([M−H]$^-$)

Example 102

5-Fluoro-2-methyl-N-[6-(4-trifluoromethyl-phenoxymethyl)-pyridin-2-yl]-benzenesulfonamide This material was prepared in analogy to example 1 from 6-(4-trifluoromethyl-phenoxymethyl)-pyridin-2-ylamine (0.08 g) and 5-fluoro-2-methyl-benzenesulfonyl chloride (0.07 g) as a light yellow solid (0.1 g). MS (ESI$^-$): 439.1 ([M−H]$^-$)

Example 103

3-Chloro-N-(6-cyclopropylmethoxymethyl-pyridin-2-yl)-2-methyl-benzenesulfonamide This material was obtained in analogy to example 1 from 6-cyclopropylmethoxymethyl-pyridin-2-ylamine (0.09 g) and 3-chloro-2-methyl-benzenesulfonyl chloride (0.13g) as an off-white gum (0.135 g). MS (ESI$^-$): 365.0 ([M−H]$^-$)

Example 104

3,4-Dichloro-N-(6-cyclopropylmethoxymethyl-pyridin-2-yl)-benzenesulfonamide

This material was obtained in analogy to example 1 from 6-cyclopropylmethoxymethyl-pyridin-2-ylamine (0.09 g) and 3,4-dichloro-benzenesulfonyl chloride (0.143g) as an off-white gum (0.143 g). MS (ESI$^-$): 385.0 ([M−H]$^-$)

Example 105

4-Fluoro-N-[6-(4-fluoro-benzyloxymethyl)-pyridin-2-yl]-benzenesulfonamide

This material was prepared in analogy to example 1 from 6-(4-fluoro-benzyloxymethyl)-pyridin-2-ylamine (0.058 g) and 4-fluoro-benzenesulfonyl chloride (0.054 g) as a light yellow gum (0.08 g). MS (ESI$^-$): 389.1 ([M−H]$^-$)

Example 106

N-[6-(4-Fluoro-benzyloxymethyl)-pyridin-2-yl]-3-trifluoromethyl-benzenesulfonamide This material was prepared in analogy to example 1 from 6-(4-fluoro-benzyloxymethyl)-pyridin-2-ylamine (0.058 g) and 3-(trifluoromethyl)-benzenesulfonyl chloride (0.067 g) as a light yellow gum (0.08g). MS (ESI$^-$): 439.1 ([M–H]$^-$)

Example 107

3-Chloro-N-(5-cyclopropylmethoxymethyl-pyridin-2-yl)-2-methyl-benzenesulfonamide Step A]: N-(5-Formyl-pyridin-2-yl)-2,2-dimethyl-propionamide A solution of N-(5-Bromo-pyridin-2-yl)-2,2-dimethyl-propionamide (8.7 g, Kelly, Tetrahedron Lett., 32, 1991, 4263) in THF (200 mL) was cooled to –70° C. under an argon atmosphere and treated dropwise over 30 minutes with n-butyllithium (45.78 mL, 1.6 M in hexane, Acros). The mixture was stirred 1 h at –70° C. and then treated dropwise (over 10 minutes, at –70° C.) with a mixture of N,N-dimethylformamide (5.25 mL) in THF (5 mL), and stirring was continued for further 30 minutes. The reaction mixture was then poured into 2M aqueous KHCO$_3$ (1.2 L), tert-butyl methyl ether (1.2 L) was added, and after stirring for 20 minutes, the layers were separated, the organic layer extracted twice with tert-butyl methyl ether (total volume 0.3 L). The combined organic layers were dried over sodium sulphate, filtered and evaporated in vacuo to give N-(5-formyl-pyridin-2-yl)-2,2-dimethyl-propionamide (7 g) as an yellow oil that was used directly in the next step.

Step B]: N-(5-Hydroxymethyl-pyridin-2-yl)-2,2-dimethyl-propionamide

N-(5-formyl-pyridin-2-yl)-2,2-dimethyl-propionamide (6.96 g) under an argon atmosphere in MeOH (120 mL) was cooled to 0° C. and then treated portion wise with sodium borohydride (1.289 g). The cooling bath was removed, stirring was continued for 30 minutes and the reaction mixture was partitioned between half-saturated aqueous NH$_4$Cl and AcOEt. The layers were separated, the organic layer dried over sodium sulphate, filtered and concentrated in vacuo. The residue was purified by flash chromatography (heptane/AcOEt 1:1 to 1:2) to give N-(5-hydroxymethyl-pyridin-2-yl)-2,2-dimethyl-propionamide (3.4 g) as a crystalline white solid. MS (ESI): 209.2 (MH$^+$).

Step C]: N-(5-Cyclopropylmethoxymethyl-pyridin-2-yl)-2,2-dimethyl-propionamide

This material was prepared in analogy to example 86 step A] from N-(5-hydroxymethyl-pyridin-2-yl)-2,2-dimethyl-propionamide (1.04 g) and bromomethyl cyclopropane (0.813 g) as a light yellow oil (0.87 g). MS (ESI): 263.1. (MH$^+$).

Step D]: 5-Cyclopropylmethoxymethyl-pyridin-2-ylamine

This material was prepared in analogy to example 86 step B] from N-(5-cyclopropylmethoxymethyl-pyridin-2-yl)-2,2-dimethyl-propionamide (0.87 g) and 3M aqueous NaOH (5.54 mL) as a yellow solid (0.527 g). MS (ESI): 179.1 (MH$^+$).

Step E]: 3-Chloro-N-(5-cyclopropylmethoxymethyl-pyridin-2-yl)-2-methyl-benzenesulfonamide This material was prepared in analogy to example 1 from 5-cyclopropylmethoxymethyl-pyridin-2-ylamine (0.089 g) and 3-chloro-2-methyl-benzenesulfonyl chloride (0.142 g) as a light yellow gum (0.152 g). MS (ESI$^-$): 365.0 ([M–H]$^-$)

Example 108

4N-(5-Cyclopropylmethoxymethyl-pyridin-2-yl)-2,5-difluoro-benzenesulfonamide

This material was prepared in analogy to example 1 from 5-cyclopropylmethoxymethyl-pyridin-2-ylamine (0.089 g) and 2,5-difluro-benzenesulfonyl chloride (0.117 g) as an off-white solid (0.119 g). MS (ESI$^-$): 353.1 ([M–H]$^-$)

Example 109

4-Chloro-N-(5-cyclopropylmethoxymethyl-pyridin-2-yl)-3-methyl-benzenesulfonamide This material was prepared in analogy to example 1 from 5-cyclopropylmethoxymethyl-pyridin-2-ylamine (0.089 g) and 3-chloro-4-methyl-benzenesulfonyl chloride (0.124 g) as an off-white solid (0.128 g). MS (ESI$^-$): 365.0 ([M–H]$^-$)

Example 110

4N-($^5$-Cyclopropylmethoxymethyl-pyridin-2-yl)-5-fluoro-2-methyl-benzenesulfonamide This material was prepared in analogy to example 1 from 5-cyclopropylmethoxymethyl-pyridin-2-ylamine (0.089 g) and 5-fluoro-2-methyl-benzenesulfonyl chloride (0.115 g) as an off-white solid (0.119 g). MS (ESI$^-$): 349.3 ([M–H]$^-$)

Example 111

Piperidine-1-sulfonic acid (5-cyclopropylmethoxymethyl-pyridin-2-yl)-amide

This material was prepared in analogy to example 1 from 5-cyclopropylmethoxymethyl-pyridin-2-ylamine (0.089 g) and piperidine-1-sulfonyl chloride (0.142 g) as a light yellow gum (0.027 g). MS (ESI$^-$): 324.2 ([M–H]$^-$)

Example 112

3-Chloro-N-(5-cyclopropylmethoxymethyl-6-methyl-pyridin-2-yl)-2-methyl-benzenesulfonamide Step A]: N-(5-Formyl-6-methyl-pyridin-2-yl)-2,2-dimethyl-propionamide This material was prepared in analogy to example 107 step A] from N-(5-bromo-6-methyl-pyridin-2-yl)-2,2-dimethyl-propionamide, 7.05 g—obtained via standard acylation of 5-bromo-6-methyl-pyridin-2-ylamine with 2,2-dimethyl-propionyl chloride in CH$_2$Cl$_2$, with triethylamine as base, as viscous brown oil, MS (ESI): 271.2 (MH$^+$)- butyllithium (34.94 mL, 1.6 M in hexane, Agros) and N,N-dimethylformamide (4 mL) as an amorphous light brown solid (5.7 g). MS (EI): 220.1 (M$^+$)

Step B]: N-(5-Hydroxymethyl-6-methyl-pyridin-2-yl)-2,2-dimethyl-propionamide

This material was prepared in analogy to example 107 step B] from N-(5-formyl-6-methyl-pyridin-2-yl)-2,2-dimethyl-propionamide (5.9 g) and sodium borohydride (1.037 g) as a light yellow solid (1.41 g). MS (ESI): 223.2 (MH$^+$).

Step C]: N-(5-Cyclopropylmethoxymethyl-6-methyl-pyridin-2-yl)-2,2-dimethyl-propionamide This material was prepared in analogy to example 86 step A] from N-(5-Hydroxymethyl-6-methyl-pyridin-2-yl)-2,2-dimethyl-propionamide (0.445 g) and bromomethyl cyclopropane (0.275 g) as a light yellow oil (0.357g). MS (ESI): 277.2 (MH$^+$).

Step D]: 5-Cyclopropylmethoxymethyl-6-methyl-pyridin-2-ylamine

This material was prepared in analogy to example 86 step B] from N-(5-cyclopropylmethoxymethyl-6-methyl-pyridin-2-yl)-2,2-dimethyl-propionamide (0.357 g) and 3M aqueous NaOH (2.68 mL) as a dark red oil (0.163 g). MS (EI): 192.2 (M$^+$).

Step E]: 3-Chloro-N-(5-cyclopropylmethoxymethyl-6-methyl-pyridin-2-yl)-2-methyl-benzenesulfonamide This material was prepared in analogy to example 1 from 5-cyclopropylmethoxymethyl-6-methyl-pyridin-2-ylamine (0.053 g) and 3-chloro-2-methyl-benzenesulfonyl chloride (0.058 g) as a light brown solid (0.046 g). MS (ESI$^-$): 379.1 ([M–H]$^-$)

Example 113

N-(5-Cyclopropylmethoxymethyl-6-methyl-pyridin-2-yl)-2,5-difluoro-benzenesulfonamide This material was prepared in analogy to example 1 from 5-cyclopropylmethoxymethyl-6-methyl-pyridin-2-ylamine (0.053 g) and 2,5-difluoro-benzenesulfonyl chloride (0.059 g) as a light yellow solid (0.063 g). MS (ESI$^-$): 367.0 ([M–H]$^-$)

Example 114

N-(5-Cyclopropylmethoxymethyl-6-methyl-pyridin-2-yl)-5-fluoro-2-methyl-benzenesulfonamide This material was prepared in analogy to example 1 from 5-cyclopropylmethoxymethyl-6-methyl-pyridin-2-ylamine (0.053 g) and 5-fluoro-2-methyl-benzenesulfonyl chloride (0.058 g) as a light yellow solid (0.063 g). MS (ESI$^-$): 363.3 ([M–H]$^-$)

Example 115

N-(5-Methoxymethyl-6-methyl-pyridin-2-yl)-3-trifluoromethyl-benzenesulfonamide

Step A]: N-(5-Methoxymethyl-6-methyl-pyridin-2-yl)-2,2-dimethyl-propionamide

This material was prepared in analogy to example 86 step A] from N-(5-hydroxymethyl-6-methyl-pyridin-2-yl)-2,2-dimethyl-propionamide (0.6 g, product of example 112 step B]) and iodomethane (0.421 g) as a white solid (0.4 g). MS (ESI): 237.2 (MH$^+$).

Step B]: 5-Methoxymethyl-6-methyl-pyridin-2-ylamine

This material was prepared in analogy to example 86 step B) from N-(5-methoxymethyl-6-methyl-pyridin-2-yl)-2,2-dimethyl-propionamide (0.4 g) and 3M aqueous NaOH (2.68 mL) as a crystalline orange solid (0.174 g). MS (EI): 152.2 (M$^+$).

Step C]: N-(5-Methoxymethyl-6-methyl-pyridin-2-yl)-3-trifluoromethyl-benzenesulfonamide This material was prepared in analogy to example 1 from 5-methoxymethyl-6-methyl-pyridin-2-ylamine (0.058 g) and 3-(trifluoromethyl)-benzenesulfonyl chloride (0.103 g) as a light yellow gum (0.1 g). MS (ESI$^-$): 359.0 ([M–H]$^-$)

Example 116

3-Chloro-N-(5-methoxymethyl-6-methyl-pyridin-2-yl)-2-methyl-benzenesulfonamide

This material was prepared in analogy to example 1 from 5-methoxymethyl-6-methyl-pyridin-2-ylamine (0.058 g) and 3-chloro-2-methyl-benzenesulfonyl chloride (0.094 g) as an off-white foam (0.093 g). MS (ESI$^-$): 339.0 ([M–H]$^-$)

Example 117

N-[5-(4-Fluoro-benzyloxymethyl)-6-methyl-pyridin-2-yl]-3-trifluoromethyl-benzenesulfonamide Step A]: N-[5-(4-Fluoro-benzyloxymethyl)-6-methyl-pyridin-2-yl]-2,2-dimethyl-propionamide This material was prepared in analogy to example 86 step A] from N-(5-hydroxymethyl-6-methyl-pyridin-2-yl)-2,2-dimethyl-propionamide (0.6 g, product of example 112 step B]) and 4-fluorobenzyl bromide (0.56 g) as an orange solid (0.8 g). MS (ESI): 231.3 (MH$^+$).

Step B]: 5-(4-Fluoro-benzyloxymethyl)-6-methyl-pyridin-2-ylamine

This material was prepared in analogy to example 86 step B] from N-[5-(4-Fluoro-benzyloxymethyl)-6-methyl-pyridin-2-yl]-2,2-dimethyl-propionamide (0.78 g) and 3M aqueous NaOH (3.93 mL) as an amorphous orange solid (0.58 g). MS (ESI): 247.2 (MH$^+$).

Step C]: N-[5-(4-Fluoro-benzyloxymethyl)-6-methyl-pyridin-2-yl]-3-trifluoromethyl-benzenesulfonamide This material was prepared in analogy to example 1 from 5-(4-fluoro-benzyloxymethyl)-6-methyl-pyridin-2-ylamine (0.08 g) and 3-(trifluoromethyl)-benzenesulfonyl chloride (0.087 g) as an amorphous orange solid (0.1 g). MS (ESI$^-$): 453.2 ([M–H]$^-$)

Example 118

3-Chloro-N-[5-(4-fluoro-benzyloxymethyl)-6-methyl-pyridin-2-yl]-2-methyl-benzenesulfonamide This material was prepared in analogy to example 1 from 5-(4-fluoro-benzyloxymethyl)-6-methyl-pyridin-2-ylamine (0.08 g) and 3-chloro-2-methyl-benzenesulfonyl chloride (0.08 g) as an amorphous light yellow solid (0.067 g). MS (ESI$^-$): 433.1 ([M–H]$^-$)

Example 119

N-(5-Ethoxymethyl-6-methyl-pyridin-2-yl)-3-trifluoromethyl-benzenesulfonamide

Step A]: N-(5-Ethoxymethyl-6-methyl-pyridin-2-yl)-2,2-dimethyl-propionamide

This material was prepared in analogy to example 86 step A] from N-(5-hydroxymethyl-6-methyl-pyridin-2-yl)-2,2-dimethyl-propionamide (0.445 g, product of example 112 step B]) and iodoethane (0.34 g) as a light yellow oil (0.32 g). MS (ESI): 251.2 (MH$^+$).

Step B]: 5-Ethoxymethyl-6-methyl-pyridin-2-ylamine

This material was prepared in analogy to example 86 step B] from N-(5-ethoxymethyl-6-methyl-pyridin-2-yl)-2,2-dimethyl-propionamide (0.32 g) and 3M aqueous NaOH (2.62 mL) as a yellow oil (0.28 g) that was used directly in the next step.

Step C]: N-(5-Ethoxymethyl-6-methyl-pyridin-2-yl)-3-trifluoromethyl-benzenesulfonamide This material was prepared in analogy to example 1 from 5-Ethoxymethyl-6-methyl-pyridin-2-ylamine (0.066 g) and 3-(trifluoromethyl)-benzenesulfonyl chloride (0.108 g) as a light yellow solid (0.115 g). MS (ESI$^-$): 373.1 ([M–H]$^-$)

Example 120

3-Chloro-2-methyl-N-{6-[(methyl-propyl-amino)-methyl]-pyridin-2-yl}-benzenesulfonamide Step A]: N-(6-chloromethyl-pyridin-2-yl)-2,2-dimethyl-propionamide N-(6-Hydroxymethyl-pyridin-2-yl)-2,2-dimethyl-propionamide (2.03 g) in CH$_2$Cl$_2$ (75 mL) was treated at RT with thionyl chloride (1.785 mL) and then heated to reflux for 1.5 h. The reaction mixture was cooled to RT and partitioned between water and AcOEt, the layers were separated, the organic layer dried over MgSO$_4$, filtered and evaporated to give N-(6-chloromethyl-pyridin-2-yl)-2,2-dimethyl-propionamide (0.66 g) as a brown liquid. MS (ESI): 227.2 (MH$^+$).

Step B): 2,2-Dimethyl-N-{6-[(methyl-propyl-amino)-methyl]-pyridin-2-yl}-propionamide N-(6-chloromethyl-pyridin-2-yl)-2,2-dimethyl-propionamide (0.66 g), methyl-propylamine (0.33 mL), KHCO$_3$ (0.32 g) and a catalytic amount of potassium iodide in acetone (10 mL) were heated to reflux for 6 h. The reaction mixture was cooled to RT and partitioned between water and AcOEt, the layers were separated, the organic layer dried over MgSO$_4$, filtered and evaporated to give 2,2-dimethyl-N-{6-[(methyl-propyl-amino)-methyl]-pyridin-2-yl}-propionamide (0.75 g) as a brown oil. MS (ESI): 264.3 (MH$^+$).

Step C): 6-[(Methyl-propyl-amino)-methyl]-pyridin-2-ylamine

This material was prepared in analogy to example 86 step B] from 2,2-dimethyl-N-{6-[(methyl-propyl-amino)-methyl]-pyridin-2-yl}-propionamide (0.755 g) and 3M aqueous NaOH (5.73 mL) as a brown liquid (0.53 g). MS (ESI): 180.2 (MH$^+$).

Step D]: 3-Chloro-2-methyl-N-{6-[(methyl-propyl-amino)-methyl]-pyridin-2-yl}-benzenesulfonamide This material was prepared in analogy to example 1 from 6-[(methyl-propyl-amino)-methyl]-pyridin-2-ylamine (0.072 g) and 3-chloro-2-methyl-benzenesulfonyl chloride (0.09 g); obtained as sodium salt, as a brown gum (0.06 g). MS (ESI$^-$): 366.1 ([M–H]$^-$)

Example 121

5-Fluoro-2-methyl-N-{6-[(methyl-propyl-amino)-methyl]-pyridin-2-yl}-benzenesulfonamide This material was prepared in analogy to example 1 from 6-[(methyl-propyl-amino)-methyl]-pyridin-2-ylamine (0.072 g) and 2-methyl-5-fluoro-benzenesulfonyl chloride (0.09 g), obtained as sodium salt, as a brown gum (0.058 g). MS (ESI$^-$): 350.3 ([M–H]$^-$)

Example 122

3-Chloro-N-(5-ethoxymethyl-6-methyl-pyridin-2-yl)-2-methyl-benzenesulfonamide

This material was prepared in analogy to example 1 from 5-ethoxymethyl-6-methyl-pyridin-2-ylamine (0.066 g) and 3-chloro-2-methyl-benzenesulfonyl chloride (0.099 g) as an off-white solid (0.08 g). MS (ESI$^-$): 351.3 ([M–H]$^-$)

Example 123

3-Chloro-N-(6-cyclopropyl-pyridin-2-yl)-2-methyl-benzenesulfonamide

Step A]: 6-Cyclopropyl-pyridin-2-ylamine

To a sealable vial under nitrogen was added 2-amino-6-bromo-pyridine (1.6 g), cyclopropyl boronic acid (1.03 g) (prepared according to Wallace et al. *Tetrahedron Lett.* 2002, 43, 6987-6990), potassium phosphate (6.87 g), tricyclohexylphosphine (0.260 g) followed by water (2 mL) and toluene (40 mL). Pd(OAc)$_2$ (0.104 g) was then added and the vial was sealed and heated at 100° C. over 16 hours. The reaction was then allowed to cool to ambient temperature and diluted with water and ethyl acetate. The phases were separated and the aqueous phase was extracted with more ethyl acetate (3×). The combined phases were washed with brine and dried over sodium sulfate. Filtration and evaporation of the volatiles afforded a crude residue which was purified via ISCO Combiflash chromatography using ethyl acetate/heptane as the eluent to give the desired 6-cyclopropyl-pyridin-2-ylamine as yellow solid (0.450 g).

Step B]: 3-Chloro-N-(6-cyclopropyl-pyridin-2-yl)-2-methyl-benzenesulfonamide

This material was obtained in analogy to example 1 from 6-cyclopropyl-pyridin-2-ylamine (0.08 g) and 3-chloro-2-methylbenzenesulfonylchoride (0.134 g) as a colorless amorphous solid. (0.075 g). MS (ESI$^+$): 323.1 ([M+H]$^+$).

Example 124

Naphthalene-1-sulfonic acid (6-cyclopropyl-pyridin-2-yl)-amide

This material was obtained in analogy to example 1 from 6-cyclopropyl-pyridin-2-ylamine (0.1 g) and naphthaline-1-sulfonylchloride (0.169 g) as a light yellow amorphous gum. (0.03 g). MS (ESI$^+$): 325.3 ([M+H]$^+$).

Example 125

4-Chloro-N-(6-cyclopropyl-pyridin-2-yl)-2,5-dimethyl-benzenesulfonamide

This material was obtained in analogy to example 1 from 6-cyclopropyl-pyridin-2-ylamine (0.1 g) and 4-chloro-2,5-dimethylbenzenesulfonylchloride (0.180 g) as an off-white amorphous solid (0.023 g). MS (ESI$^+$): 337.1 ([M+H]$^+$).

Example 126

4-Chloro-N-(6-cyclopropyl-pyridin-2-yl)-3-methyl-benzenesulfonamide

This material was obtained in analogy to example 1 from 6-cyclopropyl-pyridin-2-ylamine (0.1 g) and 3-chloro-4-methylbenzenesulfonylchloride (0.168 g) as waxy yellow solid (0.039 g). MS (ESI$^+$): 323.3 ([M+H]$^+$).

Example 127

N-(6-Cyclopropyl-pyridin-2-yl)-3-trifluoromethyl-benzenesulfonamide

This material was obtained in analogy to example 1 from 6-cyclopropyl-pyridin-2-ylamine (0.1 g) and 3-(trifluoromethyl)benzenesulfonylchloride (0.182 g) as a light yellow gum (0.060 g). MS (ESI$^+$): 343.1 ([M+H]$^+$).

Example 128

2,4-Dichloro-N-(6-cyclopropyl-pyridin-2-yl)-5-methyl-benzenesulfonamide

This material was obtained in analogy to example 1 from 6-cyclopropyl-pyridin-2-ylamine (0.1 g) and 2,4-dichloro-5-methylbenzenesulfonylchloride (0.193 g) as a light yellow gum(0.047 g). MS (ESI$^+$): 357.1 ([M+H]$^+$).

Example 129

Naphthalene-2-sulfonic acid (6-cyclopropyl-pyridin-2-yl)-amide

This material was obtained in analogy to example 1 from 6-cyclopropyl-pyridin-2-ylamine (0.1 g) and naphthaline-2-sulfonylchloride (0.169 g) as a light yellow gum (0.150 g). MS (ESI$^+$): 325.3 ([M+H]$^+$).

Example 130

N-(5-Cyclopropylmethoxymethyl-pyridin-2-yl)-3-trifluoromethyl-benzenesulfonamide This material was prepared in analogy to example 1 from 5-cyclopropylmethoxymethyl-pyridin-2-ylamine (0.051 g) and 3-(trifluromethyl)-benzenesulfonyl chloride (0.077 g) as a crystalline white solid (0.062 g). MS (ESI$^-$): 385.0 ([M−H]$^-$)

Example 131

N-(5-Ethoxymethyl-6-methyl-pyridin-2-yl)-3,5-bis-trifluoromethyl-benzenesulfonamide This material was prepared in analogy to example 1 from 5-ethoxymethyl-6-methyl-pyridin-2-ylamine (0.07 g) and 3,5-di(trifluoromethyl)-benzenesulfonyl chloride (0.145 g) as an off-white solid (0.032 g). MS (ESI$^-$): 441.1 ([M−H]$^-$)

Example 132

4-Chloro-N-(5-ethoxymethyl-6-methyl-pyridin-2-yl)-3-trifluoromethyl-benzenesulfonamide This material was prepared in analogy to example 1 from 5-ethoxymethyl-6-methyl-pyridin-2-ylamine (0.07 g) and 4-chloro-3-(trifluoromethyl)- benzenesulfonyl chloride (0.129 g) as a yellow gum (0.068 g). MS (ESI$^-$): 407.2 ([M−H]$^-$)

Example 133

4-Chloro-N-[6-(4-fluoro-benzyloxymethyl)-pyridin-2-yl]-3-trifluoromethyl-benzenesulfonamide This material was prepared in analogy to example 1 from 6-(4-fluoro-benzyloxymethyl)-pyridin-2-ylamine (0.058 g) and 4-chloro-3-(trifluoromethyl)-benzenesulfonyl chloride (0.077 g) as a light yellow gum (0.084 g). MS (ESI$^-$): 472.8 ([M−H]$^-$)

Example 134

4-Chloro-N-[6-(4-fluoro-benzyloxymethyl)-pyridin-2-yl]-2,5-dimethyl-benzenesulfonamide This material was prepared in analogy to example 1 from 6-(4-fluoro-benzyloxymethyl)-pyridin-2-ylamine (0.058 g) and 4-chloro-2,5-dimethyl-benzenesulfonyl chloride (0.066 g) as a light yellow gum (0.089 g). MS (ESI$^-$): 433.2. ([M−H]$^-$)

Example 135

3-Trifluoromethyl-N-[6-(4-trifluoromethyl-phenoxymethyl)-pyridin-2-yl]-benzenesulfonamide This material was prepared in analogy to example 1 from 6-(4-trifluoromethyl-phenoxymethyl)-pyridin-2-ylamine (0.08 g) and 3-(trifluoromethyl)-benzenesulfonyl chloride (0.081 g) as a light yellow gum (0.114 g). MS (ESI$^-$): 475.0 ([M−H]$^-$).

Example 136

N-[5-(2-Fluoro-ethoxymethyl)-6-methyl-pyridin-2-yl]-3-trifluoromethyl-benzenesulfonamide Step A]: N-[5-(2-Fluoro-ethoxymethyl)-6-methyl-pyridin-2-yl]-2,2-dimethyl-propionamide This material was prepared in analogy to example 86 step A] from N-(5-hydroxymethyl-6-methyl-pyridin-2-yl)-2,2-dimethyl-propionamide (0.556 g, product of example 112 step B]) and 1-bromo-2-fluoro-ethane (0.475 g) as a light yellow gum (0.115 g). MS (ESI): 269.3 (MH$^+$).

Step B]: 5-(2-Fluoro-ethoxymethyl)-6-methyl-pyridin-2-ylamine

This material was prepared in analogy to example 86 step B] from N-[5-(2-Fluoro-ethoxymethyl)-6-methyl-pyridin-2-yl]-2,2-dimethyl-propionamide (0.165 g) and 3M aqueous NaOH (1.23 mL) as an gum (0.174 g) that was used directly in the next step.

Step C]: N-[5-(2-Fluoro-ethoxymethyl)-6-methyl-pyridin-2-yl]-3-trifluoromethyl-benzenesulfonamide This material was prepared in analogy to example 1 from 5-(2-fluoro-ethoxymethyl)-6-methyl-pyridin-2-ylamine (0.05 g) and 3-(trifluoromethyl)-benzenesulfonyl chloride (0.073 g) as a light yellow gum (39 mg g). MS (ESI−): 391.2 ([M−H]−)

Example 137

3-Chloro-N-(5-cyclopropylmethoxymethyl-pyridin-2-yl)-benzenesulfonamide

This material was prepared in analogy to example 1 from 5-cyclopropylmethoxymethyl-pyridin-2-ylamine (0.06 g) and 3-chloro-benzenesulfonyl chloride (0.078 g) as an amorphous off-white solid (0.059 g). MS (ESI−): 351.1 ([M−H]−)

Example 138

2,4-Dichloro-N-(5-cyclopropylmethoxymethyl-pyridin-2-yl)-6-methyl-benzenesulfonamide This material was prepared in analogy to example 1 from 5-cyclopropylmethoxymethyl-pyridin-2-ylamine (0.06 g) and 2,4-dichloro-6-methyl-benzenesulfonyl chloride (0.096 g) as an off-white solid (0.069 g). MS (ESI−): 399.1 ([M−H]−)

Example 139

2,4-Dichloro-N-(5-cyclopropylmethoxymethyl-pyridin-2-yl)-6-methyl-benzenesulfonamide This material was prepared in analogy to example 1 from 5-cyclopropylmethoxymethyl-pyridin-2-ylamine (0.06 g) and 4-fluoro-3-(trifluoromethyl)-benzenesulfonyl chloride (0.097 g) as a crystalline white solid (0.066 g). MS (ESI−): 403.2 ([M−H]−)

Example 140

3-Chloro-N-(5-cyclopropylmethoxymethyl-6-methyl-pyridin-2-yl)-benzenesulfonamide This material was prepared in analogy to example 1 from 5-cyclopropylmethoxymethyl-6-methyl-pyridin-2-ylamine (0.06 g) and 3-chloro-6-methyl-benzenesulfonyl chloride (0.072 g) as a light yellow solid (0.07 g). MS (ESI−): 364.9 ([M−H] )

Example 141

2,4-Dichloro-N-(5-cyclopropylmethoxymethyl-6-methyl-pyridin-2-yl)-6-methyl-benzenesulfonamide This material was prepared in analogy to example 1 from 5-cyclopropylmethoxymethyl-6-methyl-pyridin-2-ylamine (0.06 g) and 2,4-dichloro-6-methyl-benzenesulfonyl chloride (0.089 g) as an amorphous light yellow solid (0.058 g). MS (ESI−): 413.1 ([M−H]−)

Example 142

2,4-Dichloro-N-(5-cyclopropylmethoxymethyl-6-methyl-pyridin-2-yl)-6-methyl-benzenesulfonamide This material was prepared in analogy to example 1 from 5-cyclopropylmethoxymethyl-6-methyl-pyridin-2-ylamine (0.06 g) and 3-(trifluoromethyl)-benzenesulfonyl chloride (0.084 g) as a light yellow solid. MS (ESI): 401.4 ([MH]+)

Example 143

2,4-Difluoro-N-[6-(3-fluoro-benzyloxymethyl)-pyridin-2-yl]-benzenesulfonamide

Step A]: N-[6-(3-fluoro-benzyloxymethyl)-pyridin-2-yl]-2,2-dimethyl-propionamide This material was prepared in analogy to example 86 step A] from N-(6-hydroxymethyl-pyridin-2-yl)-2,2-dimethyl-propionamide (0.73 g) and 3-fluorobenzyl bromide as a yellow solid(0.66 g). MS (ESI): 317.1 (MH+).

Step B]: 6-(3-Fluoro-benzyloxymethyl)-pyridin-2-ylamine

This material was prepared in analogy to example 86 step B] from N-[6-(3-fluoro-benzyloxymethyl)-pyridin-2-yl]-2,2-dimethyl-propionamide (0.663 g) and 3M aqueous NaOH (4.19 mL) as a brown liquid (0.596 g). MS (ESI): 233.2 (MH+).

Step C]: 2,4-Difluoro-N-[6-(3-fluoro-benzyloxymethyl)-pyridin-2-yl]-benzenesulfonamide This material was prepared in analogy to example 1 from 6-(3-fluoro-benzyloxymethyl)-pyridin-2-ylamine (0.06 g) and 2,4-difluoro-benzenesulfonyl chloride (0.06 g) as a yellow solid(0.07 g). MS (ESI−): 407.2 ([M−H]−).

Example 144

3-Chloro-N-[6-(3-fluoro-benzyloxymethyl)-pyridin-2-yl]-benzenesulfonamide

This material was prepared in analogy to example 1 from 6-(3-fluoro-benzyloxymethyl)-pyridin-2-ylamine (0.06 g) and 3-chloro-benzenesulfonyl chloride (0.06 g) as a yellow gum (0.07 g). MS (ESI−): 405.1 ([M−H]−).

Example 145

2,4-Dichloro-N-[6-(3-fluoro-benzyloxymethyl)-pyridin-2-yl]-6-methyl-benzenesulfonamide This material was prepared in analogy to example 1 from 6-(3-fluoro-benzyloxymethyl)-pyridin-2-ylamine (0.06 g) and 2,4-dichloro-6methyl-benzenesulfonyl chloride (0.074 g) as a yellow solid (0.12 g). MS (ESI−): 453.1 ([M−H]−).

Example 146

2,4-Difluoro-N-[6-(4-fluoro-benzyloxymethyl)-pyridin-2-yl]-benzenesulfonamide

This material was prepared in analogy to example 1 from 6-(4-fluoro-benzyloxymethyl)-pyridin-2-ylamine (0.07 g)

and 2,4-dichloro-6-methyl-benzenesulfonyl chloride (0.07 g) as a light yellow solid (0.104 g). MS (ESI⁻): 407.2 ([M–H]⁻).

Example 147

3-Chloro-N-[6-(4-fluoro-benzyloxymethyl)-pyridin-2-yl]-benzenesulfonamide

This material was prepared in analogy to example 1 from 6-(4-fluoro-benzyloxymethyl)-pyridin-2-ylamine (0.07 g) and 3-chloro-benzenesulfonyl chloride (0.07 g) as a light yellow gum (0.059 g). MS (ESI⁻): 405.2 ([M–H]⁻).

Example 148

2,4-Dichloro-N-[6-(4-fluoro-benzyloxymethyl)-pyridin-2-yl]-6-methyl-benzenesulfonamide This material was prepared in analogy to example 1 from 6-(4-fluoro-benzyloxymethyl)-pyridin-2-ylamine (0.07 g) and 2,4-dichloro-6-methyl-benzenesulfonyl chloride (0.086 g) as a light yellow solid (0.11 g). MS (ESI⁻): 453.1 ([M–H]⁻).

Example 149

N-(5-Cyclopropylmethoxymethyl-6-methyl-pyridin-2-yl)-5-fluoro-2-methyl-benzenesulfonamide This material was prepared in analogy to example 1 from 5-cyclopropylmethoxymethyl-6-methyl-pyridin-2-ylamine (0.06 g) and 4-fluoro-3-(trifluoromethyl)-benzenesulfonyl chloride (0.12 g) as a light yellow solid (0.12g). MS (ESI⁻): 417.0 ([M–H]⁻)

Example 150

4-Fluoro-N-[6-(3-fluoro-benzyloxymethyl)-pyridin-2-yl]-3-trifluoromethyl-benzenesulfonamide This material was prepared in analogy to example 1 from 6-(3-fluoro-benzyloxymethyl)-pyridin-2-ylamine (0.06 g) and 4-fluoro-3-(trifluoromethyl)-benzenesulfonyl chloride (0.075 g) as a light yellow solid (0.1 g). MS (ESI⁻): 457.2 ([M–H]⁻).

Example 151

4-Fluoro-N-[6-(4-fluoro-benzyloxymethyl)-pyridin-2-yl]-3-trifluoromethyl-benzenesulfonamide This material was prepared in analogy to example 1 from 6-(4-fluoro-benzyloxymethyl)-pyridin-2-ylamine (0.07 g) and 4-fluoro-3-(trifluoromethyl)-benzenesulfonyl chloride (0.087 g) as alight yellow gum (0.11 g). MS (ESI⁻): 457.2 ([M–H]⁻).

Example 152

N-[6-(4-Fluoro-benzyloxymethyl)-pyridin-2-yl]-3-trifluoromethoxy-benzenesulfonamide This material was prepared in analogy to example 1 from 6-(4-fluoro-benzyloxymethyl)-pyridin-2-ylamine (0.07 g) and 3-(trifluoromethoxy)-benzenesulfonyl chloride (0.086 g) as a light yellow gum (0.097 g). MS (ESI⁻): 455.2 ([M–H]⁻).

Example 153

N-(6-Methoxymethyl-pyridin-2-yl)-3-trifluoromethyl-benzenesulfonamide

This material was obtained in analogy to example 1 from 6-methoxymethyl-pyridin-2-ylamine (0.076 g) and 3-(trifluormethyl)-benzenesulfonyl chloride (0.148 g) as a light yellow gum (0.13 g). MS (ESI⁻): 345.1. ([M–H]⁻)

Example 154

2,4-Dichloro-N-(6-methoxymethyl-pyridin-2-yl)-6-methyl-benzenesulfonamide

This material was obtained in analogy to example 1 from 6-methoxymethyl-pyridin-2-ylamine (0.076 g) and 2,4-dichloro-6-methyl-benzenesulfonyl chloride (0.157 g) as an off-white solid (0.138 g). MS (ESI⁻): 358.9. ([M–H]⁻)

Example 155

3-Chloro-N-(6-methoxymethyl-pyridin-2-yl)-benzenesulfonamide

This material was obtained in analogy to example 1 from 6-methoxymethyl-pyridin-2-ylamine (0.076 g) and 3-chloro-benzenesulfonyl chloride (0.128 g) as light yellow gum (0.147 g). MS (ESI⁻): 311.0 ([M–H]⁻)

Example 156

3-Trifluoromethyl-N-[6-(3,3,3-trifluoro-propoxymethyl)-pyridin-2-yl]-benzenesulfonamide Step A]: 2,2-Dimethyl-N-[6-(3,3,3-trifluoro-propoxymethyl)-pyridin-2-yl]-propionamide 3,3,3-Trifluoro-propan-1-ol (0.214 g) in THF (8 mL) was treated under an argon atmosphere with sodium hydride (0.1 g, 60% suspension in oil) and stirred for 1 h at RT. N-(6-chloromethyl-pyridin-2-yl)-2,2-dimethyl-propionamide, 0.142 g, product of example 120 step A], was added and the mixture was heated at 85° C. for 2.5 h. The reaction mixture was cooled, partitioned between ice water and AcOEt, the layers were separated, the organic layer dried over Na₂SO₄, filtered and evaporated to give 2,2-dimethyl-N-[6-(3,3,3-trifluoro-propoxymethyl)-pyridin-2-yl]-propionamide (0.21 g) as a light brown oil. MS (ESI): 305.3 (MH⁺).

Step B]: 6-(3,3,3-Trifluoro-propoxymethyl)-pyridin-2-ylamine

This material was prepared in analogy to example 86 step B] from 2,2-dimethyl-N-[6-(3,3,3-trifluoro-propoxymethyl)-pyridin-2-yl]-propionamide (0.2 g) and 3M aqueous NaOH (1.31 mL) as a brown oil (0.159 g). MS (ESI): 221.2 (MH⁺).

StepC]: 3-Trifluoromethyl-N-[6-(3,3,3-trifluoro-propoxymethyl)-pyridin-2-yl]-benzenesulfonamide This material was prepared in analogy to example 1 from 6-(3,3,3-Trifluoro-propoxymethyl)-pyridin-2-ylamine (0.075 g) and 3-(trifluoromethyl)-benzenesulfonyl chloride (0.092 g) as a light yellow gum (0.048 g). MS (ESI⁻): 427.1 ([M–H]⁻).

Example 157

2,4-Dichloro-6-methyl-N-[6-(3,3,3-trifluoro-propoxymethyl)-pyridin-2-yl]-benzenesulfonamide This material was prepared in analogy to example 1 from 6-(3,3,3-Trifluoro-propoxymethyl)-pyridin-2-ylamine (0.075 g) and 2,4-dichloro-6-methyl-benzenesulfonyl chloride (0.097 g) as a light yellow gum (0.08 g). MS (ESI$^-$): 441.1 ([M−H]$^-$).

Example 158

N-[6-(2,2,2-Trifluoro-ethoxymethyl)-pyridin-2-yl]-3-trifluoromethyl-benzenesulfonamide Step A]: 2,2-Dimethyl-N-[6-(2,2,2-trifluoro-ethoxymethyl)-pyridin-2-yl]-propionamide This material was obtained in analogy to example 156 step A from N-(6-chloromethyl-pyridin-2-yl)-2,2-dimethyl-propionamide, 0.567 g, product of example 120 step A ], and 2,2,2-trifluoro-ethanol as a brown liquid (0.726 g) that was used directly in the next step.

Step B]: 6-(2,2,2-Trifluoro-ethoxymethyl)-pyridin-2-ylamine

This material was prepared in analogy to example 86 step B] from 2,2-Dimethyl-N-[6-(2,2,2-trifluoro-ethoxymethyl)-pyridin-2-yl]-propionamide (0.726 g) and 3M aqueous NaOH (5 mL) as a brown liquid (0.4 g). MS (EI): 206.1 (M$^+$).

Step C]: N-[6-(2,2,2-Trifluoro-ethoxymethyl)-pyridin-2-yl]-3-trifluoromethyl-benzenesulfonamide This material was prepared in analogy to example 1 from 6-(2,2,2-Trifluoro-ethoxymethyl)-pyridin-2-ylamine (0.08 g) and 3-(trifluoromethyl)-benzenesulfonyl chloride (0.104 g) as alight yellow gum (0.066 g). MS (ESI$^-$): 413.1 ([M−H]$^-$).

Example 159

2,4-Dichloro-6-methyl-N-[6-(2,2,2-trifluoro-ethoxymethyl)-pyridin-2-yl]-benzenesulfonamide This material was prepared in analogy to example 1 from 6-(2,2,2-Trifluoro-ethoxymethyl)-pyridin-2-ylamine (0.08 g) and 2,4-dichloro-6-methyl-benzenesulfonyl chloride (0.11 g) as a light yellow solid (0.1 g). MS (ESI$^-$): 427.1 ([M−H]$^-$).

Example 160

3-Chloro-N-[6-(2-cyclopropyl-ethoxymethyl)-pyridin-2-yl]-benzenesulfonamide

Step A]: N-[6-(2-Cyclopropyl-ethoxymethyl)-pyridin-2-yl]-2,2-dimethyl-propionamide This material was obtained in analogy to example 156 step A from N-(6-chloromethyl-pyridin-2-yl)-2,2-dimethyl-propionamide, 0.567 g, product of example 120 step A ], and 2-cyclopropyl-ethanol (0.51 g) as a light yellow oil (0.51 g). MS (ESI): 277.2 ([MH]$^+$).

Step B]: 6-(2-Cyclopropyl-ethoxymethyl)-pyridin-2-ylamine

This material was prepared in analogy to example 86 step B] from N-[6-(2-cyclopropyl-ethoxymethyl)-pyridin-2-yl]-2,2-dimethyl-propionamide (0.51 g) and 3M aqueous NaOH (3.7 mL) as a light yellow oil (0.39 g) that was used directly in the next step.

Step C]: 3-Chloro-N-[6-(2-cyclopropyl-ethoxymethyl)-pyridin-2-yl]-benzenesulfonamide This material was prepared in analogy to example 1 from 6-(2-cyclopropyl-ethoxymethyl)-pyridin-2-ylamine (0.08 g) and 3-chloro-benzenesulfonyl chloride (0.095 g) as a light yellow gum (0.096 g). MS (ESI$^-$): 365.0 ([M−H]$^-$).

Example 161

N-[6-(2-Cyclopropyl-ethoxymethyl)-pyridin-2-yl]-3-trifluoromethyl-benzenesulfonamide This material was prepared in analogy to example 1 from 6-(2-cyclopropyl-ethoxymethyl)-pyridin-2-ylamine (0.08 g) and 3-(trifluormethyl)-benzenesulfonyl chloride (0.11 g) as a light yellow gum (0.106 g). MS (ESI$^-$): 399.2 ([M−H]$^-$).

Example 162

N-[6-(2-Cyclopropyl-ethoxymethyl)-pyridin-2-yl]-4-fluoro-3-trifluoromethyl-benzenesulfonamide This material was prepared in analogy to example 1 from 6-(2-cyclopropyl-ethoxymethyl)-pyridin-2-ylamine (0.08 g) and 4-fluoro-3-(trifluormethyl)-benzenesulfonyl chloride (0.12 g) as a light yellow gum (0.08 g). MS (ESI$^-$): 417.0 ([M−H]$^-$).

Example 163

2,4-Dichloro-N-[6-(2-cyclopropyl-ethoxymethyl)-pyridin-2-yl]-6-methyl-benzenesulfonamide This material was prepared in analogy to example 1 from 6-(2-cyclopropyl-ethoxymethyl)-pyridin-2-ylamine (0.08 g) and 2,4-dichloro-6-methyl-benzenesulfonyl chloride (0.117 g) as a light yellow gum (0.088 g). MS (ESI$^-$): 413.1 ([M−H]$^-$).

Example 164

2,4-Dichloro-5-methyl-N-[6-(2,2,2-trifluoro-ethoxymethyl)-pyridin-2-yl]-benzenesulfonamide This material was prepared in analogy to example 1 from 6-(2,2,2-Trifluoro-ethoxymethyl)-pyridin-2-ylamine (0.08 g) and 2,4-dichloro-5-methyl-benzenesulfonyl chloride (0.11 g) as a light yellow gum (0.095 g). MS (ESI$^-$): 427.1 ([M−H]$^-$).

Example 165

2-Chloro-N-[6-(2,2,2-trifluoro-ethoxymethyl)-pyridin-2-yl]-5-trifluoromethyl-benzenesulfonamide This material was prepared in analogy to example 1 from 6-(2,2,2-Trifluoro-ethoxymethyl)-pyridin-2-ylamine (0.08 g) and 2-chloro-5-(trifluoromethyl)- benzenesulfonyl chloride (0.119 g) as alight yellow solid (0.123 g). MS (ESI$^-$): 447.0 ([M−H]$^-$).

Example 166

2,4-Dichloro-N-[6-(3-chloro-benzyloxymethyl)-pyridin-2-yl]-6-methyl-benzenesulfonamide Step A]: N-[6-(3-Chloro-benzyloxymethyl)-pyridin-2-yl]-2,2-dimethyl-propionamide This material was prepared in analogy to example 86 step A] from N-(6-hydroxymethyl-pyridin-2-yl)-2,2-dimethyl-propionamide (0.73 g) and 3-chlorobenzyl bromide as a yellow oil (0.75 g). MS (ESI): 332.2 (MH$^+$).

Step B]: 6-(3-Chloro-benzyloxymethyl)-pyridin-2-ylamine

This material was prepared in analogy to example 86 step B] from N-[6-(3-chloro-benzyloxymethyl)-pyridin-2-yl]-2,2-dimethyl-propionamide (0.75 g) and 3M aqueous NaOH (4.51 mL) as a brown liquid (0.56 g). MS (ESI): 249.1 (MH$^+$).

Step C]: 2,4-Dichloro-N-[6-(3-chloro-benzyloxymethyl)-pyridin-2-yl]-6-methyl-benzenesulfonamide This material was prepared in analogy to example 1 from 6-(3-chloro-benzyloxymethyl)-pyridin-2-ylamine (0.08 g) and 2,4-dichloro-6-methyl-benzenesulfonyl chloride (0.092g) as a light yellow gum (0.039 g). MS (ESI$^-$): 469.0 ([M–H]$^-$).

Example 167

N-[6-(3-Chloro-benzyloxymethyl)-pyridin-2-yl]-4-fluoro-3-trifluoromethyl-benzenesulfonamide This material was prepared in analogy to example 1 from 6-(3-chloro-benzyloxymethyl)-pyridin-2-ylamine (0.08 g) and 4-fluoro-3-(trifluoromethyl)-benzenesulfonyl chloride (0.092g) as a light yellow gum (0.088 g). MS (ESI$^-$): 472.8 ([M–H]$^-$).

Example 168

N-[6-(4-Chloro-benzyloxymethyl)-pyridin-2-yl]-4-fluoro-3-trifluoromethyl-benzenesulfonamide Step A]: N-[6-(4-Chloro-benzyloxymethyl)-pyridin-2-yl]-2,2-dimethyl-propionamide This material was prepared in analogy to example 86 step A] from N-(6-hydroxymethyl-pyridin-2-yl)-2,2-dimethyl-propionamide (0.73 g) and 4-chlorobenzyl bromide as a yellow oil (0.868 g). MS (ESI): 332.2 (MH$^+$).

Step B]: 6-(4-Chloro-benzyloxymethyl)-pyridin-2-ylamine

This material was prepared in analogy to example 86 step B] from N-[6-(4-chloro-benzyloxymethyl)-pyridin-2-yl]-2,2-dimethyl-propionamide (0.868 g) and 3M aqueous NaOH (5.22 mL) as a light yellow liquid (0.63 g). MS (ESI): 249.1 (MH$^+$).

Step C]: N-[6-(4-Chloro-benzyloxymethyl)-pyridin-2-yl]-4-fluoro-3-trifluoromethyl-benzenesulfonamide This material was prepared in analogy to example 1 from 6-(4-chloro-benzyloxymethyl)-pyridin-2-ylamine (0.08 g) and 4-fluoro-3-(trifluoromethyl)-benzenesulfonyl chloride (0.092g) as a light yellow gum (0.039 g). MS (ESI$^-$): 472.8 ([M–H]$^-$).

Example 169

2,4-Dichloro-N-[6-(4-chloro-benzyloxymethyl)-pyridin-2-yl]-6-methyl-benzenesulfonamide This material was prepared in analogy to example 1 from 6-(4-chloro-benzyloxymethyl)-pyridin-2-ylamine (0.08 g) and 2,4-dichloro-6-methyl-benzenesulfonyl chloride (0.092 g) as an off-white solid (0.082 g). MS (ESI$^-$): 469.0 ([M–H]$^-$).

Example 170

N-[5-(2,2,2-Trifluoro-ethoxymethyl)-pyridin-2-yl]-3-trifluoromethyl-benzenesulfonamide Step A]: N-(5-Chloromethyl-pyridin-2-yl)-2,2-dimethyl-propionamide This material was obtained in analogy to example 120 step A], from N-(5-hydroxymethyl-pyridin-2-yl)-2,2-dimethyl-propionamide, 1.25 g, product of example 107 step B], and thionyl chloride (0.65 mL) as a brown solid (0.87 g). MS (ESI): 227.2 (MH$^+$).

Step B]: 2,2-Dimethyl-N-[5-(2,2,2-trifluoro-ethoxymethyl)-pyridin-2-yl]-propionamide This material was obtained in analogy to example 156 step A] from N-(5-chloromethyl-pyridin-2-yl)-2,2-dimethyl-propionamide (0.43 g) and 2,2,2-trifluoro-ethanol (0.41 mL) as a brown liquid (0.56 g) that was used directly in the next step.

Step C]: 5-(2,2,2-Trifluoro-ethoxymethyl)-pyridin-2-ylamine

This material was prepared in analogy to example 86 step B] from 2,2-dimethyl-N-[5-(2,2,2-trifluoro-ethoxymethyl)-pyridin-2-yl]-propionamide (0.56 g) and 3M aqueous NaOH (3.87 mL) as a crystalline white solid (0.123 g). MS (ESI): 207.1 (MH$^+$).

Step D]: N-[5-(2,2,2-Trifluoro-ethoxymethyl)-pyridin-2-yl]-3-trifluoromethyl-benzenesulfonamide This material was prepared in analogy to example 1 from 5-(2,2,2-Trifluoro-ethoxymethyl)-pyridin-2-ylamine (0.06 g) and 3-(trifluoromethyl)-benzenesulfonyl chloride (0.078 g) as an off-white solid (0.056 g). MS (ESI$^-$): 413.1 ([M–H]$^-$).

Example 171

2,4-Dichloro-5-methyl-N-[5-(2,2,2-trifluoro-ethoxymethyl)-pyridin-2-yl]-benzenesulfonamide This material was prepared in analogy to example 1 from 5-(2,2,2-Trifluoro-ethoxymethyl)-pyridin-2-ylamine (0.06 g) and 2,4-dichloro-6-methyl-benzenesulfonyl chloride (0.083 g) as an off-white solid (0.072 g). MS (ESI$^-$): 427.1 ([M–H]$^-$).

Example 172

3-Chloro-2-methyl-N-(3,4,5,6-tetrahydro-2H-[1,3']bipyridinyl-6'-yl)-benzenesulfonamide Step A]: 6'-Nitro-3,4,5,6-tetrahydro-2H-[1,3']bipyridinyl 5-Bromo-2-nitropyridine (3.0 g), tetrabutylammonium iodide (0.273 g), potassium carbonate (2.24 g) and piperidine (1.6 mL) were dissolved in DMSO (25 mL) and heated at 80°

C. for 12 hours. The mixture was diluted with ethyl acetate, filtered and the filtrate was concentrated in vacuo. To the residue was added water (75 mL) and the precipitate was isolated by filtration. The solid was evaporated three times from toluene to remove residual water and the product was further dried in vacuo to give 6'-nitro-3,4,5,6-tetrahydro-2H-[1,3']bipyridinyl (2.87 g) as a yellow powder. MS (EI): 207.2 (M$^+$).

Step B]: 3,4,5,6-Tetrahydro-2H-[1,3']bipyridinyl-6'-ylamine

To 6'-Nitro-3,4,5,6-tetrahydro-2H-[1,3']bipyridinyl (0.25 g) in THF (8 mL) was added iron (0.539 mg) and water (2.5 mL). Then acetic acid (0.35 mL) was added dropwise and the mixture was allowed to stir at 45° C. for 12 hours. TLC analysis confirmed complete consumption of the starting material. The suspension was filtered through celite and the filter cake was washed well with ethyl acetate. The filtrate was concentrated in vacuo prior to addition of 2N NaOH. The aqueous layer was saturated with NaCl and extracted with ethyl acetate. The organic phase was washed with brine, dried over $Na_2SO_4$ and evaporated to give a residue that was purified by flash chromatography on silica gel (gradient of MeOH in DCM containing 0.5% $NH_4OH$). 3,4,5,6-tetrahydro-2H-[1,3']bipyridinyl-6'-ylamine was obtained as a black oil (0.196 g). MS (ESI): 178.1 (MH$^+$).

Step C]: 3-Chloro-2-methyl-N-(3,4,5,6-tetrahydro-2H-[1,3']bipyridinyl-6'-yl)-benzenesulfonamide 3,4,5,6-Tetrahydro-2H-[1,3']bipyridinyl-6'-ylamine (0.19 g) and 3-chloro-2-methylbenzenesulfonyl chloride (0.24 g) were dissolved in pyridine (4 mL) and heated at 50° C. over night. The mixture was concentrated in vacuo, taken up in ethyl acetate and extracted with 1M Cu(II)SO$_4$ solution. The organic layer was washed once again with Cu(II)SO$_4$ solution, dried over $Na_2SO_4$ and evaporated in vacuo. The product was purified by flash chromatography on silica gel (gradient of ethyl acetate in heptane) to give 3-chloro-2-methyl-N-(3,4,5,6-tetrahydro-2H-[1,3']bipyridinyl-6'-yl)-benzenesulfonamide (0.1 g) as a light brown foam. MS (ESI$^-$): 364.0 ([M−H]$^-$).

Example 173

3-Chloro-2-methyl-N-(5-pyrrolidin-1-yl-pyridin-2-yl)-benzenesulfonamide

3-Chloro-2-methyl-N-(5-pyrrolidin-1-yl-pyridin-2-yl)-benzenesulfonamide was obtained in analogy to example 172, steps A] to C] from 5-bromo-2-nitropyridine, pyrrolidine and 3-chloro-2-methylbenzenesulfonyl chloride as a yellow foam. MS (ESI$^-$): 350.2 ([M−H]$^-$).

Example 174

3-Chloro-2-methyl-N-(5-morpholin-4-yl-pyridin-2-yl)-benzenesulfonamide

3-Chloro-2-methyl-N-(5-morpholin-4-yl-pyridin-2-yl)-benzenesulfonamide was obtained in analogy to example 172, steps A] to C] from 5-bromo-2-nitropyridine, morpholine and 3-chloro-2-methylbenzenesulfonyl chloride as a light yellow powder. MS (ESI$^-$): 366.0 ([M−H]$^-$).

Example 175

N-(5-Benzyl-pyridin-2-yl)-3-chloro-2-methyl-benzenesulfonamide

N-(5-Benzyl-pyridin-2-yl)-3-chloro-2-methyl-benzenesulfonamide was made in analogy to example 172, step C] from known 5-benzyl-pyridin-2-ylamine (made according to Kelly et al., J. Am. Chem. Soc. 112 (22), 1990, 8024-8034) and 3-chloro-2-methylbenzenesulfonyl chloride and was obtained as a white powder. MS (ESI$^-$): 371.1 ([M−H]$^-$).

Example 176

3-Chloro-2-methyl-N-(5-phenethyl-pyridin-2-yl)-benzenesulfonamide

Step A]: 5-Phenethyl-pyridin-2-ylamine

5-Phenethyl-pyridin-2-ylamine which has been described in the literature (Kaminski et al., J. Med. Chem. 28 (7), 1985, 876-892) was made from known 5-styryl-pyridin-2-ylamine (Bumagin et al., J. Organomet. Chem. 486 (1-2), 1995, 259-262) by catalytic hydrogenation: 5-Styryl-pyridin-2-ylamine (0.3 g) was dissolved in ethanol (6 mL) and 5% Pd on charcoal (38 mg) was added. A hydrogen atmosphere was introduced by repeated evacuation/hydrogen introduction and the suspension was allowed to stir at RT for 2 hours. The mixture was filtered through celite and the filter cake was washed well with ethanol. The filtrate was evaporated to give 5-phenethyl-pyridin-2-ylamine as a colorless solid (100 mg) that was not further purified. MS (ESI): 199.1 (MH$^+$).

Step B]: 3-Chloro-2-methyl-N-(5-phenethyl-pyridin-2-yl)-benzenesulfonamide

3-Chloro-2-methyl-N-(5-phenethyl-pyridin-2-yl)-benzenesulfonamide was made in analogy to example 172, step C] from 5-phenethyl-pyridin-2-ylamine (117 mg) and 3-chloro-2-methylbenzenesulfonyl chloride (133 mg) to give the desired product as a white powder (129 mg). MS (ESI$^-$): 385.0 ([M−H]$^-$)

Example 177

3-Chloro-2-methyl-N-(6-methyl-5-phenethyl-pyridin-2-yl)-benzenesulfonamide

Step A]: 6-Methyl-5-styryl-pyridin-2-ylamine

5-Bromo-6-methyl-pyridin-2-ylamine (0.5 g), styrene (0.28 g) and potassium formate (0.68 g) were dissolved in DMF (5 mL). Tetrabutylammonium chloride (0.74 g) and palladium(II)acetate (30 mg) were added and the mixture was stirred under argon at 60° C. for 18 hours; a black suspension was obtained. The mixture was poured into saturated $NaHCO_3$ solution (75 mL) and extracted with ethyl acetate. The organic layers were washed with brine, dried over $Na_2SO_4$ and evaporated. The residue was purified by flash chromatography (silica gel, gradient of ethyl acetate in heptane) to give 6-methyl-5-styryl-pyridin-2-ylamine (144 mg) as a 7:3 mixture of (E) and (Z) isomers as a white foam. MS (ESI): 211.3 (MH$^+$). This material was contaminated with trace amounts of 6-methyl-5-phenethyl-pyridin-2-ylamine according to MS analysis.

Step B] 6-Methyl-5-phenethyl-pyridin-2-ylamine

6-Methyl-5-styryl-pyridin-2-ylamine (141 mg) was hydrogenated in analogy to example 176, step A] to give 6-methyl-5-phenethyl-pyridin-2-ylamine (139 mg) as light brown foam. MS (ESI): 213.3 (MH⁺).

Step C] 3-Chloro-2-methyl-N-(6-methyl-5-phenethyl-pyridin-2-yl)-benzenesulfonamide This material was obtained from 6-methyl-5-phenethyl-pyridin-2-ylamine (134 mg) and 3-chloro-2-methylbenzenesulfonyl chloride (142 mg) in analogy to example 172, step C] as white foam (166 mg). MS (ESI⁻): 399.1 ([M–H]⁻).

Example 178

3-Chloro-2-methyl-N-(5-thiomorpholin-4-yl-pyridin-2-yl)-benzenesulfonamide

3-Chloro-2-methyl-N-(5-thiomorpholin-4-yl-pyridin-2-yl)-benzenesulfonamide was obtained in low yield in analogy to example 172, steps A] to C] from 5-bromo-2-nitropyridine, thiomorpholine and 3-chloro-2-methylbenzenesulfonyl chloride as a reddish, viscous oil. MS (ESI⁻): 382.1 ([M–H]⁻).

Example 179

2,4-Dichloro-N-{5-[2-(4-chloro-phenyl)-ethyl]-pyridin-2-yl}-6-methyl-benzenesulfonamide This material was obtained in analogy to example 177, steps A] to C] from 5-iodo-pyridin-2-ylamine, 1-chloro-4-vinyl-benzene and 2,4-dichloro-6-methylbenzenesulfonyl chloride as a light yellow powder. MS (ESI⁻): 353.1 ([M–H]⁻).

Example 180

3-Chloro-N-{5-[2-(4-methoxy-phenyl)-ethyl]-pyridin-2-yl}-2-methyl-benzenesulfonamide This material was obtained in analogy to example 177, steps A] to C] from 5-iodo-pyridin-2-ylamine, 1-methoxy-4-vinyl-benzene and 3-chloro-2-methylbenzenesulfonyl chloride as a light yellow foam. MS (ESI⁻): 415.3 ([M–H]⁻).

Example 181

3-Chloro-N-{5-[2-(3-fluoro-phenyl)-ethyl]-pyridin-2-yl}-2-methyl-benzenesulfonamide This material was obtained in analogy to example 177, steps A] to C] from 5-iodo-pyridin-2-ylamine, 1-fluoro-3-vinyl-benzene and 3-chloro-2-methylbenzenesulfonyl chloride as a light yellow foam. MS (ESI⁻): 403.4 ([M–H]⁻).

Example 182

3-Chloro-2-methyl-N-{5-[2-(2-trifluoromethyl-phenyl)-ethyl]-pyridin-2-yl}-benzenesulfonamide This material was obtained in analogy to example 177, steps A] to C] from 5-iodo-pyridin-2-ylamine, 1-trifluoromethyl-2-vinyl-benzene and 3-chloro-2-methylbenzenesulfonyl chloride as a white foam. MS (ESI⁻): 453.3 ([M–H]⁻).

Example 183

3-Chloro-N-{5-[2-(4-fluoro-phenyl)-ethyl]-pyridin-2-yl}-2-methyl-benzenesulfonamide This material was obtained in analogy to example 177, steps A] to C] from 5-iodo-pyridin-2-ylamine, 1-fluoro-4-vinyl-benzene and 3-chloro-2-methylbenzenesulfonyl chloride as a light yellow foam. MS (ESI⁻): 403.4 ([M–H]⁻).

Example 184

3-Chloro-2-methyl-N-(5-phenoxy-pyridin-2-yl)-benzenesulfonamide

Step A] 2-Nitro-5-phenoxy-pyridine

Phenol (306 mg) was dissolved in dry DMF (5 mL) and subsequently, sodium hydride (60% in mineral oil, 130 mg) was added which resulted in strong hydrogen gas evolution. The mixture was then allowed to stir at RT for 30 minutes. Subsequently, 5-bromo-2-nitro-pyridine (600 mg) was added und the resulting mixture was stirred at 60° C. for 12 hours. The reaction mixture was poured into ice water and the aqueous phase was saturated with NaCl and extracted with ethyl acetate. The organic layer was separated, washed with brine, dried over Na₂SO₄ and evaporated. The residue was purified by flash chromatography (silica gel, gradient of ethyl acetate in heptane) to give 2-nitro-5-phenoxy-pyridine as a light yellow foam (267 mg). MS (EI): 216.1 (M⁺).

Step B] 5-Phenoxy-pyridin-2-ylamine

2-Nitro-5-phenoxy-pyridine (262 mg) was dissolved in dry ethanol (12 mL) and 10% palladium on charcoal (90 mg) was added. A hydrogen atmosphere was introduced by repeated evacuation/hydrogen introduction. The mixture was then allowed to stir for 18 hours. The catalyst was removed by filtration through celite and the filtrate was concentrated in vacuo to give 5-phenoxy-pyridin-2-ylamine (217 mg) as a yellow foam. This material was used without further purification. MS (EI): 186.1 (M⁺).

Step C] 3-Chloro-2-methyl-N-(5-phenoxy-pyridin-2-yl)-benzenesulfonamide

5-Phenoxy-pyridin-2-ylamine (100 mg) was treated with 3-chloro-2-methylbenzenesulfonyl chloride (122 mg) in the presence of pyridine (3 mL) as described in example 172, step C] to give 3-Chloro-2-methyl-N-(5-phenoxy-pyridin-2-yl)-benzenesulfonamide (37 mg) as a white foam. MS (ESI): 375.1 (MH⁺).

Example 185

3-Chloro-N-[5-(2-chloro-phenoxy)-pyridin-2-yl]-2-methyl-benzenesulfonamide

This material was obtained in analogy to example 184, steps A] to C] from 2-chloro-phenol, 5-bromo-2-nitro-pyridine and 3-chloro-2-methylbenzenesulfonyl chloride as a white foam. MS (ESI⁻): 407.1 ([M–H]⁻).

Example 186

3-Chloro-N-[5-(4-fluoro-phenoxy)-pyridin-2-yl]-2-methyl-benzenesulfonamide benzenesulfonamide This material was obtained in analogy to example 184, steps A] to C] from 4-fluoro-phenol, 5-bromo-2-nitro-pyridine and 3-chloro-2-methylbenzenesulfonyl chloride as a white solid. MS (ESI): 392.9 (MH+).

Example 187

2,4-Dichloro-6-methyl-N-(5-phenoxy-pyridin-2-yl)-benzenesulfonamide

This material was obtained in analogy to example 184, steps A] to C] from phenol, 5-bromo-2-nitro-pyridine and 2,4-dichloro-6-methylbenzenesulfonyl chloride as a light brown solid. MS (ESI−): 407.1 ([M−H]−).

Example 188

2,4-Dichloro-N-[5-(2-chloro-phenoxy)-pyridin-2-yl]-6-methyl-benzenesulfonamide

This material was obtained in analogy to example 184, steps A] to C] from 2-chloro-phenol, 5-bromo-2-nitro-pyridine and 2,4-dichloro-6-methylbenzenesulfonyl chloride as a light yellow foam. MS (ESI−): 441.0 ([M−H]−).

Example 189

2,4-Dichloro-N-[5-(4-fluoro-phenoxy)-pyridin-2-yl]-6-methyl-benzenesulfonamide

This material was obtained in analogy to example 184, steps A] to C] from 4-fluoro-phenol, 5-bromo-2-nitro-pyridine and 2,4-dichloro-6-methylbenzenesulfonyl chloride as a light brown solid. MS (ESI−): 425.0 ([M−H]−).

Example 190

3-Chloro-2-methyl-N-[5-(2-quinolin-2-yl-ethyl)-pyridin-2-yl]-benzenesulfonamide

This material was obtained in analogy to example 177, steps A] to C] from 5-iodo-pyridin-2-ylamine, 2-vinyl-quinoline and 3-chloro-2-methylbenzenesulfonyl chloride as a light yellow foam. MS (ESI−): 436.2 ([M−H]−).

Example 191

2,4-Dichloro-6-methyl-N-[5-(2-quinolin-2-yl-ethyl)-pyridin-2-yl]-benzenesulfonamide

This material was obtained in analogy to example 177, steps A] to C] from 5-iodo-pyridin-2-ylamine, 2-vinyl-quinoline and 2,4-dichloro-6-methylbenzenesulfonyl chloride as a light yellow foam. MS (ESI−): 470.0 ([M−H]−).

Example 192

3-Chloro-2-methyl-N-[5-(2-pyridin-2-yl-ethyl)-pyridin-2-yl]-benzenesulfonamide

This material was obtained in analogy to example 177, steps A] to C] from 5-iodo-pyridin-2-ylamine, 2-vinyl-pyridine and 3-chloro-2-methylbenzenesulfonyl chloride as a white powder. MS (ESI−): 386.0 ([M−H]−).

Example 193

A compound of formula I can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 194

A compound of formula I can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 195

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48h after transfection cells were washed twice with ice-cold PBS (Phsophate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated wit a tip sonicator (10% output; 2×30 sec.) and cleared by a low speed centrifugation (10 min×9000 g; 4° C.). The microsomal fraction was collected by a high speed centrifugation (60 min×110,000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 IC$_{50}$ (nM) |
| --- | --- |
| Example 105 | 16 |
| Example 186 | 5 |

It is to be understood that the invention is not limited to the particular embodiments of the invention described above, as variations of the particular embodiments may be made and still fall within the scope of the appended claims.

What is claimed is:

1. A compound of the formula (I):

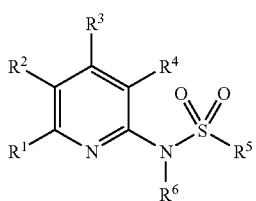

wherein:
R$^1$ is hydrogen, alkyl, cycloalkyl, hydroxy, hydroxyalkyl, alkoxy, alkoxyalkyl, aminoalkyl, aryl, heterocyclyl, alkylsulfonyl, alkylsulfanyl, alkylcarbonylalkyl, alkylcarbonyloxyalkyl, aminocarbonylalkyl, heterocyclylcarbonylalkyl, heterocyclylalkoxyalkyl, alkoxycarbonylalkyl, alkoxyalkylaminocarbonylalkyl, cycloalkylalkoxyalkyl, arylalkyloxyalkyl, aryloxyalkyl, haloalkyl, haloalkoxy or haloalkoxyalkyl;

R$^2$ is hydrogen, alkyl, cycloalkylalkoxyalkyl, alkoxyalkyl, arylalkoxyalkyl, haloalkoxyalkyl, piperidyl, pyrrolidyl, morpholinyl, thiomorpholinyl, arylalkyl, arylalkoxy, aryloxy, heterocyclylalkoxy or heterocyclylalkyl;

R$^3$ is hydrogen or alkyl;

R$^4$ is hydrogen, alkyl or halogen;

R$^5$ is phenyl, naphtyl, thiophenyl, pyridyl, quinolyl, piperidyl, morpholyl, thiomorpholyl or 1,2,3,4-tetrahydro-isoquinolinyl optionally substituted with one or more substituents independently selected from alkyl, cycloalkyl, halogen, hydroxy, hydroxyalkyl, alkoxy, alkoxyalkyl, hydroxyalkoxy, alkoxyalkoxy, cyano, nitro, trifluoromethyl, trifluoromethoxy, trifluoromethylcarbonyl, aryl, arylalkyl, aryloxy, alkoxycarbonylalkoxy and alkylsulfonyl;

R$^6$ is hydrogen or alkyl;

or a pharmaceutically acceptable salt or ester thereof;

with the proviso that N-(6-(1,1-dimethylethyl)-2-pyridinyl)-4-methyl-benzenesulfonamide is excluded, and with the proviso that when R$^1$ is hydrogen or methyl, then R$^2$ is not hydrogen or methyl.

2. The compound according to claim 1, wherein R$^5$ is phenyl, naphtyl, piperidyl or 1,2,3,4-tetrahydro-isoquinolinyl optionally substituted with one to three substituents independently selected from alkyl, halogen, alkoxy, nitro, trifluoromethyl, trifluoromethoxy, trifluoromethylcarbonyl, aryl, aryloxy and alkylsulfonyl.

3. The compound according to claim 1, wherein R$^5$ is phenyl or naphtyl optionally substituted with one to three substituents independently selected from alkyl, halogen, trifluoromethyl, trifluoromethoxy and aryl.

4. The compound according to claim 1, wherein R$^6$ is hydrogen.

5. The compound according to claim 1, wherein R$^1$ is alkyl, cycloalkyl, hydroxyalkyl, alkoxyalkyl, aryl, alkoxyalkylaminocarbonylalkyl, cycloalkylalkoxyalkyl, arylalkyloxyalkyl or trifluoroalkoxyalkyl.

6. The compound according to claim 1, wherein R$^1$ is hydrogen.

7. The compound according to claim 1, wherein R$^2$ is hydrogen, cycloalkylalkoxyalkyl, alkoxyalkyl, piperidyl, pyrrolidyl, morpholinyl, thiomorpholinyl, arylalkyl or aryloxy.

8. The compound according to claim 1, wherein R$^3$ is hydrogen.

9. The compound according to claim 1, wherein R$^4$ is hydrogen or halogen.

10. The compound according to claim 1, wherein R$^4$ is hydrogen.

11. The compound according to claim 1, selected from
3-Chloro-N-(6-ethyl-pyridin-2-yl)-2-methyl-benzenesulfonamide;
Biphenyl-4-sulfonic acid (6-ethyl-pyridin-2-yl)-amide;
Biphenyl-4-sulfonic acid (6-propyl-pyridin-2-yl)-amide;
3-Chloro-2-methyl-N-(6-propyl-pyridin-2-yl)-benzenesulfonamide;
Naphthalene-2-sulfonic acid (6-propyl-pyridin-2-yl)-amide;
3,4-Dichloro-N-(6-propyl-pyridin-2-yl)-benzenesulfonamide;
2,5-Difluoro-N-(6-propyl-pyridin-2-yl)-benzenesulfonamide;
2,4-Dichloro-6-methyl-N-(6-propyl-pyridin-2-yl)-benzenesulfonamide;
5-Chloro-naphthalene-2-sulfonic acid (6-propyl-pyridin-2-yl)-amide;

3,4-Dimethoxy-N-(6-propyl-pyridin-2-yl)-benzenesulfonamide;
4,5-Dichloro-2-fluoro-N-(6-propyl-pyridin-2-yl)-benzenesulfonamide;
2,4-Dichloro-5-methyl-N-(6-propyl-pyridin-2-yl)-benzenesulfonamide;
Piperidine-1-sulfonic acid (6-propyl-pyridin-2-yl)-amide;
3-Chloro-N-(6-isopropyl-pyridin-2-yl)-4-methyl-benzenesulfonamide;
2,5-Difluoro-N-(6-isopropyl-pyridin-2-yl)-benzenesulfonamide;
N-(6-Isopropyl-pyridin-2-yl)-4-(4-trifluoromethyl-phenoxy)-benzenesulfonamide;
2,4-Dichloro-N-(6-isopropyl-pyridin-2-yl)-5-methyl-benzenesulfonamide;
N-(6-Isopropyl-pyridin-2-yl)-4-methanesulfonyl-benzenesulfonamide;
N-(6-Isopropyl-pyridin-2-yl)-4-trifluoromethoxy-benzenesulfonamide;
2-(2,2,2-Trifluoro-acetyl)-1,2,3,4-tetrahydro-isoquinoline-7-sulfonic acid (6-isopropyl-pyridin-2-yl)-amide;
N-(6-Isopropyl-pyridin-2-yl)-3-(4-trifluoromethyl-phenoxy)-benzenesulfonamide;
Naphthalene-2-sulfonic acid (6-isopropyl-pyridin-2-yl)-amide;
N-(6-Isopropyl-pyridin-2-yl)-3-trifluoromethyl-benzenesulfonamide;
N-[6-(2-Chloro-phenyl)-pyridin-2-yl]-5-fluoro-2-methyl-benzenesulfonamide;
3-Chloro-N-[6-(2-chloro-phenyl)-pyridin-2-yl]-2-methyl-benzenesulfonamide;
Biphenyl-4-sulfonic acid [6-(2-chloro-phenyl)-pyridin-2-yl]-amide;
3-Chloro-N-[6-(2,4-difluoro-phenyl)-pyridin-2-yl]-2-methyl-benzenesulfonamide;
3-Chloro-N-[6-(3-fluoro-phenyl)-pyridin-2-yl]-2-methyl-benzenesulfonamide;
3-Chloro-N-[6-(2,3-difluoro-phenyl)-pyridin-2-yl]-2-methyl-benzenesulfonamide;
3-Chloro-N-[6-(2,5-dichloro-phenyl)-pyridin-2-yl]-2-methyl-benzenesulfonamide;
N-[6-(2,5-Dichloro-phenyl)-pyridin-2-yl]-5-fluoro-2-methyl-benzenesulfonamide;
3-Chloro-N-[6-(3-chloro-phenyl)-pyridin-2-yl]-2-methyl-benzenesulfonamide;
N-[6-(3-Chloro-phenyl)-pyridin-2-yl]-5-fluoro-2-methyl-benzenesulfonamide;
3-Chloro-N-[6-(2-fluoro-phenyl)-pyridin-2-yl]-2-methyl-benzenesulfonamide;
5-Fluoro-N-[6-(2-fluoro-phenyl)-pyridin-2-yl]-2-methyl-benzenesulfonamide;
3-Chloro-2-methyl-N-[6-(2-trifluoromethyl-phenyl)-pyridin-2-yl]-benzenesulfonamide;
5-Fluoro-2-methyl-N-[6-(2-trifluoromethyl-phenyl)-pyridin-2-yl]-benzenesulfonamide;
N-[6-(2-Chloro-phenyl)-pyridin-2-yl]-2,5-difluoro-benzenesulfonamide;
N-[6-(2-Chloro-phenyl)-pyridin-2-yl]-2-trifluoromethyl-benzenesulfonamide;
3-Chloro-N-[6-(2-methoxy-phenyl)-pyridin-2-yl]-2-methyl-benzenesulfonamide;
3-Chloro-N-[6-(4-fluoro-2-methyl-phenyl)-pyridin-2-yl]-2-methyl-benzenesulfonamide;
5-Fluoro-N-[6-(4-fluoro-2-methyl-phenyl)-pyridin-2-yl]-2-methyl-benzenesulfonamide;
N-[2,3']Bipyridinyl-6-yl-3-chloro-2-methyl-benzenesulfonamide;
2,5-Difluoro-N-[6-(4-fluoro-2-methyl-phenyl)-pyridin-2-yl]-benzenesulfonamide;
2,4-Dichloro-N-[6-(4-fluoro-2-methyl-phenyl)-pyridin-2-yl]-6-methyl-benzenesulfonamide;
3,4-Dichloro-N-[6-(4-fluoro-2-methyl-phenyl)-pyridin-2-yl]-benzenesulfonamide;
3-Chloro-N-(6-methoxy-pyridin-2-yl)-2-methyl-benzenesulfonamide;
Biphenyl-4-sulfonic acid (6-methoxy-pyridin-2-yl)-amide;
5-Fluoro-N-(6-methoxy-pyridin-2-yl)-2-methyl-benzenesulfonamide;
Naphthalene-2-sulfonic acid (6-methoxy-pyridin-2-yl)-amide;
3-Chloro-N-(6-ethoxy-pyridin-2-yl)-2-methyl-benzenesulfonamide;
Biphenyl-4-sulfonic acid (6-ethoxy-pyridin-2-yl)-amide;
Naphthalene-2-sulfonic acid (6-ethoxy-pyridin-2-yl)-amide;
3-Chloro-N-(6-ethylsulfanyl-pyridin-2-yl)-2-methyl-benzenesulfonamide;
Biphenyl-4-sulfonic acid (6-ethylsulfanyl-pyridin-2-yl)-amide;
Naphthalene-2-sulfonic acid (6-ethylsulfanyl-pyridin-2-yl)-amide;
Naphthalene-2-sulfonic acid (6-ethanesulfonyl-pyridin-2-yl)-amide;
3-Chloro-2-methyl-N-[6-(2-oxo-pentyl)-pyridin-2-yl]-benzenesulfonamide;
2-[6-(Biphenyl-4-sulfonylamino)-pyridin-2-yl]-N,N-diethyl-acetamide;
Biphenyl-4-sulfonic acid [6-(2-morpholin-4-yl-2-oxo-ethyl)-pyridin-2-yl]-amide;
[6-(3-Chloro-2-methyl-benzenesulfonylamino)-pyridin-2-yl]-acetic acid methyl ester;
[6-(5-Fluoro-2-methyl-benzenesulfonylamino)-pyridin-2-yl]-acetic acid methyl ester;
N,N-Diethyl-2-[6-(4'-fluoro-biphenyl-4-sulfonylamino)-pyridin-2-yl]-acetamide;
4-Fluoro-biphenyl-4-sulfonic acid [6-(2-morpholin-4-yl-2-oxo-ethyl)-pyridin-2-yl]-amide;
2-[6-(4-Fluoro-biphenyl-4-sulfonylamino)-pyridin-2-yl]-N-(2-methoxy-ethyl)-acetamide;
2-[6-(3-Chloro-2-methyl-benzenesulfonylamino)-pyridin-2-yl]-N,N-diethyl-acetamide;
2-[6-(3,4-Dichloro-benzenesulfonylamino)-pyridin-2-yl]-N,N-diethyl-acetamide
2-[6-(3-Chloro-2-methyl-benzenesulfonylamino)-3-methyl-pyridin-2-yl]-N,N-diethyl-acetamide;
2-[6-(3,4-Dichloro-benzenesulfonylamino)-3-methyl-pyridin-2-yl]-N,N-diethyl-acetamide;
3-Chloro-N-(6-hydroxymethyl-pyridin-2-yl)-2-methyl-benzenesulfonamide;
3-Chloro-N-(6-methoxymethyl-pyridin-2-yl)-2-methyl-benzenesulfonamide;
2,5-Difluoro-N-(6-methoxymethyl-pyridin-2-yl)-benzenesulfonamide;
3-Chloro-N-(6-methoxymethyl-pyridin-2-yl)-4-methyl-benzenesulfonamide;
N-(6-Cyclopropylmethoxymethyl-pyridin-2-yl)-2,5-difluoro-benzenesulfonamide;
5-Fluoro-N-(6-methoxymethyl-pyridin-2-yl)-2-methyl-benzenesulfonamide;
2,5-Difluoro-N-(6-hydroxymethyl-pyridin-2-yl)-benzenesulfonamide;
Acetic acid 6-(2,5-difluoro-benzenesulfonylamino)-pyridin-2-ylmethyl ester;

Naphthalene-2-sulfonic acid (6-hydroxymethyl-pyridin-2-yl)-amide;
3-Chloro-N-(6-cyclopropylmethoxymethyl-pyridin-2-yl)-4-methyl-benzenesulfonamide;
N-(6-Cyclopropylmethoxymethyl-pyridin-2-yl)-5-fluoro-2-methyl-benzenesulfonamide;
3-Chloro-N-[6-(4-fluoro-benzyloxymethyl)-pyridin-2-yl]-4-methyl-benzenesulfonamide;
3-Chloro-N-[6-(4-fluoro-benzyloxymethyl)-pyridin-2-yl]-2-methyl-benzenesulfonamide;
2,5-Difluoro-N-[6-(4-fluoro-benzyloxymethyl)-pyridin-2-yl]-benzenesulfonamide;
5-Fluoro-N-[6-(4-fluoro-benzyloxymethyl)-pyridin-2-yl]-2-methyl-benzenesulfonamide;
Piperidine-1-sulfonic acid (6-methoxymethyl-pyridin-2-yl)-amide;
Piperidine-1-sulfonic acid (6-cyclopropylmethoxymethyl-pyridin-2-yl)-amide
3-Chloro-4-methyl-N-[6-(4-trifluoromethyl-phenoxymethyl)-pyridin-2-yl]-benzenesulfonamide;
3-Chloro-2-methyl-N-[6-(4-trifluoromethyl-phenoxymethyl)-pyridin-2-yl]-benzenesulfonamide;
2,5-Difluoro-N-[6-(4-trifluoromethyl-phenoxymethyl)-pyridin-2-yl]-benzenesulfonamide;
5-Fluoro-2-methyl-N-[6-(4-trifluoromethyl-phenoxymethyl)-pyridin-2-yl]-benzenesulfonamide;
3-Chloro-N-(6-cyclopropylmethoxymethyl-pyridin-2-yl)-2-methyl-benzenesulfonamide;
3,4-Dichloro-N-(6-cyclopropylmethoxymethyl-pyridin-2-yl)-benzenesulfonamide;
4-Fluoro-N-[6-(4-fluoro-benzyloxymethyl)-pyridin-2-yl]-benzenesulfonamide;
N-[6-(4-Fluoro-benzyloxymethyl)-pyridin-2-yl]-3-trifluoromethyl-benzenesulfonamide;
3-Chloro-N-(5-cyclopropylmethoxymethyl-pyridin-2-yl)-2-methyl-benzenesulfonamide;
N-(5-Cyclopropyl-methoxymethyl-pyridin-2-yl)-2,5-difluoro-benzenesulfonamide 4-Chloro-N-(5-cyclopropylmethoxymethyl-pyridin-2-yl)-3-methyl-benzenesulfonamide;
N-(5-Cyclopropylmethoxymethyl-pyridin-2-yl)-5-fluoro-2-methyl-benzenesulfonamide;
Piperidine-1-sulfonic acid (5-cyclopropyl-methoxymethyl-pyridin-2-yl)-amide;
3-Chloro-N-(5-cyclopropyl methoxymethyl-6-methyl-pyridin-2-yl)-2-methyl-benzenesulfonamide;
N-(5-Cyclopropylmethoxymethyl-6-methyl-pyridin-2-yl)-2,5-difluoro- benzenesulfonamide;
N-(5-Cyclopropylmethoxymethyl-6-methyl-pyridin-2-yl)-5-fluoro-2-methyl-benzenesulfonamide;
N-(5-Methoxymethyl-6-methyl-pyridin-2-yl)-3-trifluoromethyl-benzenesulfonamide;
3-Chloro-N-(5-methoxymethyl-6-methyl-pyridin-2-yl)-2-methyl-benzenesulfonamide;
N-[5-(4-fluoro-benzyloxymethyl)-6-methyl-pyridin-2-yl]-3- trifluoromethylbenzenesulfonamide;
3-Chloro-N-[5-(4-fluoro-benzyloxymethyl)-6-methyl-pyridin-2-yl]-2-methylbenzenesulfonamide;
N-(5-Ethoxymethyl-6-methyl-pyridin-2-yl)-3-trifluoromethylbenzenesulfonamide;
3-Chloro-2-methyl-N-{6-[(methyl-propyl-amino)-methyl]-pyridin2-yl}-benzenesulfonamide;
5-Fluoro-2-methyl-N-{6-[(methyl-propyl-amino)-methyl]-pyridin-2-yl}-benzenesulfonamide;
3-Chloro-N-(5-ethoxymethyl-6-methyl-pyridin-2-yl)-2-methyl-benzenesulfonamide;
3-Chloro-N-(6-cyclopropyl-pyridin-2-yl)-2-methyl-benzenesulfonamide;
Naphthalene-1-sulfonic acid (6-cyclopropyl-pyridin-2-yl)-amide;
4-Chloro-N-(6-cyclopropyl-pyridin-2-yl)-2,5-dimethyl-benzenesulfonamide;
4-Chloro-N-(6-cyclopropyl-pyridin-2-yl)-3-methyl-benzenesulfonamide;
N-(6-Cyclopropyl-pyridin-2-yl)-3-trifluoromethyl-benzenesulfonamide;
2,4-Dichloro-N-(6-cyclopropyl-pyridin-2-yl)-5-methyl-benzenesulfonamide;
Naphthalene-2-sulfonic acid (6-cyclopropyl-pyridin2-yl)-amide;
N-(5-Cyclopropylmethoxymethyl-pyridin-2-yl)-3-trifluoromethyl-benzenesulfonamide;
N-(5-Ethoxymethyl-6-methyl-pyridin-2-yl)-3,5-bis-trifluoromethyl-benzenesulfonamide;
4-Chloro-N-(5-ethoxymethyl-6-methyl-pyridin-2-yl)-3-trifluoromethyl-benzenesulfonamide;
4-Chloro-N-[6-(4-fluoro-benzyloxymethyl)-pyridin-2-yl]-3-trifluoromethyl-benzenesulfonamide;
4-Chloro-N-[6-(4-fluoro-benzyloxymethyl)-pyridin-2-yl]-2,5-dimethyl-benzenesulfonamide;
3-Trifluoromethyl-N-[6-(4-trifluoromethyl-phenoxymethyl)-pyridin-2-yl]-benzenesulfonamide;
N-[5-(2-Fluoro-ethoxymethyl)-6-methyl-pyridin-2-yl]-3-trifluoromethyl-benzenesulfonamide;
3-Chloro-N-(5-cyclopropylmethoxymethyl-pyridin-2-yl)-benzenesulfonamide;
2,4-Dichloro-N-(5-cyclopropylmethoxymethyl-pyridin-2-yl)-6-methyl- benzenesulfonamide;
N-(5-Cyclopropylmethoxymethyl-pyridin-2-yl)-4-fluoro-3-trifluoromethyl-benzenesulfonamide;
3-Chloro-N-(5-cyclopropylmethoxymethyl-6-methyl-pyridin-2-yl)-benzenesulfonamide;
2,4-Dichloro-N-(5-cyclopropylmethoxymethyl-6-methyl-pyridin-2-yl)-6-methyl-benzenesulfonamide;
N-(5-Cyclopropylmethoxymethyl-6-methyl-pyridin-2-yl)-3-trifluoromethyl-benzenesulfonamide;
2,4-Difluoro-N-[6-(3-fluoro-benzyloxymethyl)-pyridin-2-yl]-benzenesulfonamide;
3-Chloro-N-[6-(3-fluoro-benzyloxymethyl)-pyridin-2-yl]-benzenesulfonamide;
2,4-Dichloro-N-[6-(3-fluoro-benzyloxymethyl)-pyridin-2-yl]-6-methyl-benzenesulfonamide;
2,4-Difluoro-N-[6-(4-fluoro-benzyloxymethyl)-pyridin-2-yl]-benzenesulfonamide;
3-Chloro-N-[6-(4-fluoro-benzyloxymethyl)-pyridin-2-yl]-benzenesulfonamide;
2,4-Dichloro-N-[6-(4-fluoro-benzyloxymethyl)-pyridin-2-yl]-6-methyl-benzenesulfonamide;
N-(5-Cyclopropylmethoxymethyl-6-methyl-pyridin-2-yl)-4-fluoro-3-trifluoromethyl-benzenesulfonamide;
4-Fluoro-N-[6-(3-fluoro-benzyloxymethyl)-pyridin-2-yl]-3-trifluoromethyl-benzenesulfonamide;
4-Fluoro-N-[6-(4-fluoro-benzyloxymethyl)-pyridin-2-yl]-3-trifluoromethyl-benzenesulfonamide;
N-[6-(4-Fluoro-benzyloxymethyl)-pyridin-2-yl]-3-trifluoromethoxy-benzenesulfonamide;
N-(6-Methoxymethyl-pyridin-2-yl)-3-trifluoromethyl-benzenesulfonamide;
2,4-Dichloro-N-(6-methoxymethyl-pyridin-2-yl)-6-methyl-benzenesulfonamide;
3-Chloro-N-(6-methoxymethyl-pyridin-2-yl)-benzenesulfonamide;

3-Trifluoromethyl-N-[6-(3,3,3-trifluoro-propoxymethyl)-pyridin-2-yl]-benzenesulfonamide;
2,4-Dichloro-6-methyl-N-[6-(3,3,3-trifluoro-propoxymethyl)-pyridin-2-yl]-benzenesulfonamide;
N-[6-(2,2,2-Trifluoro-ethoxymethyl)-pyridin-2-yl]-3-trifluoromethyl-benzenesulfonamide;
2,4-Dichloro-6-methyl-N-[6-(2,2,2-trifluoro-ethoxymethyl)-pyridin-2-yl]-benzenesulfonamide;
3-Chloro-N-[6-(2-cyclopropyl-ethoxymethyl)-pyridin-2-yl]-benzenesulfonamide;
N-[6-(2-Cyclopropyl-ethoxymethyl)-pyridin-2-yl]-3-trifluoromethyl-benzenesulfonamide;
N-[6-(2-Cyclopropyl-ethoxymethyl)-pyridin-2-yl]-4-fluoro-3-trifluoromethyl-benzenesulfonamide;
2,4-Dichloro-N-[6-(2-cyclopropyl-ethoxymethyl)-pyridin-2-yl]-6-methyl-benzenesulfonamide;
2,4-Dichloro-5-methyl-N-[6-(2,2,2-trifluoro-ethoxymethyl)-pyridin-2-yl]-benzenesulfonamide;
2-Chloro-N-[6-(2,2,2-trifluoro-ethoxymethyl)-pyridin-2-yl]-5-trifluoromethyl-benzenesulfonamide;
2,4-Dichloro-N-[6-(3-chloro-benzyloxymethyl)-pyridin-2-yl]-6-methyl-benzenesulfonamide;
N-[6-(3-Chloro-benzyloxymethyl)-pyridin-2-yl]-4-fluoro-3-trifluoromethyl-benzenesulfonamide;
N-[6-(4-Chloro-benzyloxymethyl)-pyridin-2-yl]-4-fluoro-3-trifluoromethyl-benzenesulfonamide;
2,4-Dichloro-N-[6-(4-chloro-benzyloxymethyl)-pyridin-2-yl]-6-methyl-benzenesulfonamide;
N-[5-(2,2,2-Trifluoro-ethoxymethyl)-pyridin-2-yl]-3-trifluoromethyl-benzenesulfonamide;
2,4-Dichloro-5-methyl-N-[5-(2,2,2-trifluoro-ethoxymethyl)-pyridin-2-yl]-benzenesulfonamide;
3-Chloro-2-methyl-N-(3,4,5,6-tetrahydro-2H-[1,3']bipyridinyl-6'-yl)-benzenesulfonamide;
3-Chloro-2-methyl-N-(5-pyrrolidin-1-yl-pyridin-2-yl)-benzenesulfonamide;
3-Chloro-2-methyl-N-(5-morpholin-4-yl-pyridin-2-yl)-benzenesulfonamide;
N-(5-Benzyl-pyridin-2-yl)-3-chloro-2-methyl-benzenesulfonamide;
3-Chloro-2-methyl-N-(5-phenethyl-pyridin-2-yl)-benzenesulfonamide;
3-Chloro-2-methyl-N-(6-methyl-5-phenethyl-pyridin-2-yl)-benzenesulfonamide;
3-Chloro-2-methyl-N-(5-thiomorpholin-4-yl-pyridin-2-yl)-benzenesulfonamide;
2,4-Dichloro-N-{5-[2-(4-chloro-phenyl)-ethyl]-pyridin-2-yl}-6-methyl-benzenesulfonamide;
3-Chloro-N-{5-[2-(4-methoxy-phenyl)-ethyl]-pyridin-2-yl}-2-methyl-benzenesulfonamide;
3-Chloro-N-{5-[2-(3-fluoro-phenyl)-ethyl]-pyridin-2-yl}-2-methyl-benzenesulfonamide;
3-Chloro-2-methyl-N-{5-[2-(2-trifluoromethyl-phenyl)-ethyl]-pyridin-2-yl}-benzenesulfonamide 3-Chloro-N-{5-[2-(4-fluoro-phenyl)-ethyl]-pyridin-2-yl}-2-methyl-benzenesulfonamide;
3-Chloro-2-methyl-N-(5-phenoxy-pyridin-2-yl)-benzenesulfonamide;
3-Chloro-N-[5-(2-chloro-phenoxy)-pyridin-2-yl]-2-methyl-benzenesulfonamide;
3-Chloro-N-[5-(4-fluoro-phenoxy)-pyridin-2-yl]-2-methyl-benzenesulfonamide;
2,4-Dichloro-6-methyl-N-(5-phenoxy-pyridin-2-yl)-benzenesulfonamide;
2,4-Dichloro-N-[5-(2-chloro-phenoxy)-pyridin-2-yl]-6-methyl-benzenesulfonamide;
2,4-Dichloro-N-[5-(4-fluoro-phenoxy)-pyridin-2-yl]-6-methyl-benzenesulfonamide;
3-Chloro-2-methyl-N-[5-(2-quinolin-2-yl-ethyl)-pyridin-2-yl]-benzenesulfonamide;
2,4-Dichloro-6-methyl-N-[5-(2-quinolin-2-yl-ethyl)-pyridin-2-yl]-benzenesulfonamide; and
3-Chloro-2-methyl-N-[5-(2-pyridin-2-yl-ethyl)-pyridin-2-yl]-benzenesulfonamide.

12. The compound according to claim 1, selected from:
3-Chloro-N-(6-ethyl-pyridin-2-yl)-2-methyl-benzenesulfonamide;
Biphenyl-4-sulfonic acid (6-propyl-pyridin-2-yl)-amide;
3-Chloro-2-methyl-N-(6-propyl-pyridin-2-yl)-benzenesulfonamide;
2,4-Dichloro-6-methyl-N-(6-propyl-pyridin-2-yl)-benzenesulfonamide;
5-Chloro-naphthalene-2-sulfonic acid (6-propyl-pyridin-2-yl)-amide;
3-Chloro-N-(6-isopropyl-pyridin-2-yl)-4-methyl-benzenesulfonamide;
N-(6-Isopropyl-pyridin-2-yl)-3-trifluoromethyl-benzenesulfonamide;
3-Chloro-2-methyl-N-[6-(2-trifluoromethyl-phenyl)-pyridin-2-yl]-benzenesulfonamide;
2,5-Difluoro-N-[6-(4-fluoro-2-methyl-phenyl)-pyridin-2-yl]-benzenesulfonamide;
2,4-Dichloro-N-[6-(4-fluoro-2-methyl-phenyl)-pyridin-2-yl]-6-methyl-benzenesulfonamide;
2-[6-(3-Chloro-2-methyl-benzenesulfonylamino)-pyridin-2-yl]-N,N-diethyl-acetamide;
3-Chloro-N-(6-hydroxymethyl-pyridin-2-yl)-2-methyl-benzenesulfonamide;
3-Chloro-N-(6-methoxymethyl-pyridin-2-yl)-2-methyl-benzenesulfonamide;
3-Chloro-N-(6-cyclopropylmethoxymethyl-pyridin-2-yl)-2-methyl-benzenesulfonamide;
3,4-Dichloro-N-(6-cyclopropylmethoxymethyl-pyridin-2-yl)-benzenesulfonamide;
4-Fluoro-N-[6-(4-fluoro-benzyloxymethyl)-pyridin-2-yl]-benzenesulfonamide;
N-[6-(4-Fluoro-benzyloxymethyl)-pyridin-2-yl]-3-trifluoromethyl-benzenesulfonamide;
3-Chloro-N-(5-cyclopropylmethoxymethyl-pyridin-2-yl)-2-methyl-benzenesulfonamide;
3-Chloro-N-(5-cyclopropyl methoxymethyl-6-methyl-pyridin-2-yl)-2-methyl-benzenesulfonamide;
3-Chloro-N-(5-methoxymethyl-6-methyl-pyridin-2-yl)-2-methyl-benzenesulfonamide;
N-(5-Ethoxymethyl-6-methyl-pyridin-2-yl)-3-trifluoromethylbenzenesulfonamide;
3-Chloro-N-(6-cyclopropyl-pyridin-2-yl)-2-methyl-benzenesulfonamide;
Naphthalene-1-sulfonic acid (6-cyclopropyl-pyridin-2-yl)-amide;
4-Chloro-N-(6-cyclopropyl-pyridin-2-yl)-2,5-dimethyl-benzenesulfonamide;
N-(6-Cyclopropyl-pyridin-2-yl)-3-trifluoromethyl-benzenesulfonamide;
N-(5-Cyclopropylmethoxymethyl-pyridin-2-yl)-3-trifluoromethyl-benzenesulfonamide;
4-Chloro-N-(5-ethoxymethyl-6-methyl-pyridin-2-yl)-3-trifluoromethyl-benzenesulfonamide;
2,4-Dichloro-N-(5-cyclopropylmethoxymethyl-pyridin-2-yl)-6-methyl- benzenesulfonamide;
N-(5-Cyclopropylmethoxymethyl-pyridin-2-yl)-4-fluoro-3-trifluoromethyl-benzenesulfonamide;

2,4-Dichloro-N-(5-cyclopropylmethoxymethyl-6-methyl-pyridin-2-yl)-6-methyl-benzenesulfonamide;
N-(5-Cyclopropylmethoxymethyl-6-methyl-pyridin-2-yl)-3-trifluoromethyl-benzenesulfonamide;
2,4-Dichloro-N-[6-(4-fluoro-benzyloxymethyl)-pyridin-2-yl]-6-methyl-benzenesulfonamide;
4-Fluoro-N-[6-(4-fluoro-benzyloxymethyl)-pyridin-2-yl]-3-trifluoromethyl-benzenesulfonamide;
N-[6-(4-Fluoro-benzyloxymethyl)-pyridin-2-yl]-3-trifluoromethoxy-benzenesulfonamide;
N-(6-Methoxymethyl-pyridin-2-yl)-3-trifluoromethyl-benzenesulfonamide;
3-Trifluoromethyl-N-[6-(3,3,3-trifluoro-propoxymethyl)-pyridin-2-yl]-benzenesulfonamide;
2,4-Dichloro-6-methyl-N-[6-(3,3,3-trifluoro-propoxymethyl)-pyridin-2-yl]-benzenesulfonamide;
2,4-Dichloro-6-methyl-N-[6-(2,2,2-trifluoro-ethoxymethyl)-pyridin-2-yl]-benzenesulfonamide;
2,4-Dichloro-N-[6-(2-cyclopropyl-ethoxymethyl)-pyridin-2-yl]-6-methyl-benzenesulfonamide;
2,4-Dichloro-N-[6-(3-chloro-benzyloxymethyl)-pyridin-2-yl]-6-methyl-benzenesulfonamide;
N-[6-(4-Chloro-benzyloxymethyl)-pyridin-2-yl]-4-fluoro-3-trifluoromethyl-benzenesulfonamide;
2,4-Dichloro-N-[6-(4-chloro-benzyloxymethyl)-pyridin-2-yl]-6-methyl-benzenesulfonamide;
3-Chloro-2-methyl-N-(3,4,5,6-tetrahydro-2H-[1,3']bipyridinyl-6'-yl)-benzenesulfonamide;
3-Chloro-2-methyl-N-(5-pyrrolidin-1-yl-pyridin-2-yl)-benzenesulfonamide;
3-Chloro-2-methyl-N-(5-morpholin-4-yl-pyridin-2-yl)-benzenesulfonamide;
N-(5-Benzyl-pyridin-2-yl)-3-chloro-2-methyl-benzenesulfonamide;
3-Chloro-2-methyl-N-(6-methyl-5-phenethyl-pyridin-2-yl)-benzenesulfonamide;
3-Chloro-2-methyl-N-(5-thiomorpholin-4-yl-pyridin-2-yl)-benzenesulfonamide;
2,4-Dichloro-N-{5-[2-(4-chloro-phenyl)-ethyl]-pyridin-2-yl}-6-methyl-benzenesulfonamide;
3-Chloro-N-{5-[2-(3-fluoro-phenyl)-ethyl]-pyridin-2-yl}-2-methyl-benzenesulfonamide;
3-Chloro-N-{5-[2-(4-fluoro-phenyl)-ethyl]-pyridin-2-yl}-2-methyl-benzenesulfonamide;
3-Chloro-2-methyl-N-(5-phenoxy-pyridin-2-yl)-benzenesulfonamide;
3-Chloro-N-[5-(2-chloro-phenoxy)-pyridin-2-yl]-2-methyl-benzenesulfonamide;
3-Chloro-N-[5-(4-fluoro-phenoxy)-pyridin-2-yl]-2-methyl-benzenesulfonamide;
2,4-Dichloro-6-methyl-N-(5-phenoxy-pyridin-2-yl)-benzenesulfonamide;
2,4-Dichloro-N-[5-(2-chloro-phenoxy)-pyridin-2-yl]-6-methyl-benzenesulfonamide; and
2,4-Dichloro-N-[5-(4-fluoro-phenoxy)-pyridin-2-yl]-6-methyl-benzenesulfonamide.

13. A process for the preparation of a compound according to claim 1, comprising the steps of:
a) reaction of a compound according to formula (II):

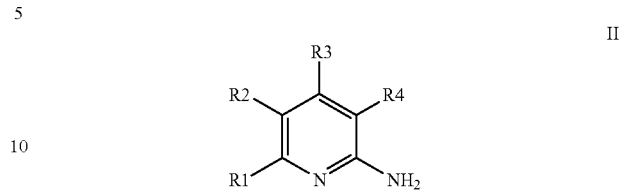

in the presence of a compound according to formula

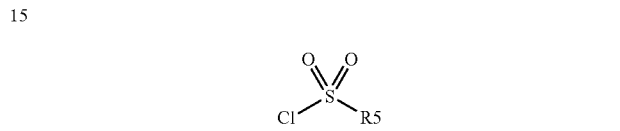

in order to obtain a compound of the formula

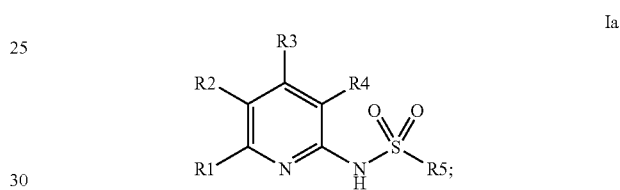

and optionally
b) further reaction in the presence of a compound of the formula $R^6$—X in order to obtain a compound of the formula

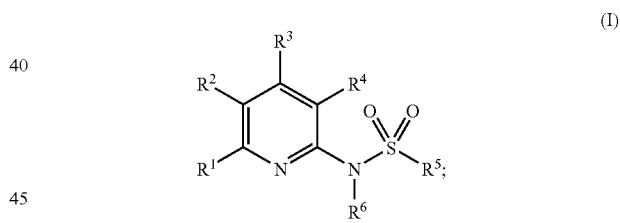

wherein $R^1$ to $R^6$ are defined as in claim 1 and X is Cl, Br or I.

14. A pharmaceutical composition, comprising a therapeutically effective amount of a compound according to claim 1 and a therapeutically inert carrier.

15. A method for the treatment of diabetes and obesity, comprising the step of administering a therapeutically effective amount of a compound according to claim 1 to a patient in need thereof.

16. The method according to claim 15, wherein said diabetes is Type II diabetes.

* * * * *